(12) United States Patent
Kagabu et al.

(10) Patent No.: US 12,156,523 B2
(45) Date of Patent: Dec. 3, 2024

(54) PLANT DISEASE CONTROL AGENT

(71) Applicant: MMAG CO., LTD., Tokyo (JP)

(72) Inventors: Shinzo Kagabu, Gifu (JP); Kentaro Yamamoto, Yokohama (JP); Ikuya Ohno, Yokohama (JP); Hirotaka Nagata, Yokohama (JP); Yukiko Takiguchi, Yokohama (JP); Kenji Umemura, Yokohama (JP); Masaaki Mitomi, Yokohama (JP)

(73) Assignee: MMAG CO., LTD., Tokyo (JP)

( * ) Notice: Subject to any disclaimer, the term of this patent is extended or adjusted under 35 U.S.C. 154(b) by 256 days.

(21) Appl. No.: 16/493,875

(22) PCT Filed: Mar. 16, 2018

(86) PCT No.: PCT/JP2018/010408
§ 371 (c)(1),
(2) Date: Sep. 13, 2019

(87) PCT Pub. No.: WO2018/169038
PCT Pub. Date: Sep. 20, 2018

(65) Prior Publication Data
US 2021/0120817 A1    Apr. 29, 2021

(30) Foreign Application Priority Data

Mar. 17, 2017  (JP) ................................ 2017-052072
Nov. 9, 2017   (JP) ................................ 2017-216236

(51) Int. Cl.
| | | |
|---|---|---|
| *A01N 43/58* | (2006.01) | |
| *A01N 43/40* | (2006.01) | |
| *A01N 43/52* | (2006.01) | |
| *A01N 43/54* | (2006.01) | |
| *A01N 43/60* | (2006.01) | |
| *A01N 43/653* | (2006.01) | |
| *A01N 43/78* | (2006.01) | |
| *A01N 43/80* | (2006.01) | |
| *C07D 213/79* | (2006.01) | |
| *C07D 213/81* | (2006.01) | |
| *C07D 401/12* | (2006.01) | |
| *C07D 405/12* | (2006.01) | |
| *C07D 409/12* | (2006.01) | |
| *C07D 413/12* | (2006.01) | |
| *C07D 417/12* | (2006.01) | |

(52) U.S. Cl.
CPC ............ *A01N 43/58* (2013.01); *A01N 43/40* (2013.01); *A01N 43/52* (2013.01); *A01N 43/54* (2013.01); *A01N 43/60* (2013.01); *A01N 43/653* (2013.01); *A01N 43/78* (2013.01); *A01N 43/80* (2013.01); *C07D 213/79* (2013.01); *C07D 213/81* (2013.01); *C07D 401/12* (2013.01); *C07D 405/12* (2013.01); *C07D 409/12* (2013.01); *C07D 413/12* (2013.01); *C07D 417/12* (2013.01)

(58) Field of Classification Search
CPC ........ A01N 43/58; A01N 43/40; A01N 43/52; A01N 43/54; A01N 43/60; A01N 43/78; A01N 43/80; A01N 43/653; A01N 43/56; A01N 43/84; A01N 43/76; C07D 213/79; C07D 213/81; C07D 401/12; C07D 405/12; C07D 409/12; C07D 413/12; C07D 417/12; C07D 213/61; C07D 413/04; C07D 213/83; C07D 401/06; C07D 417/06; C07D 213/30
See application file for complete search history.

(56) References Cited

U.S. PATENT DOCUMENTS

| | | | | |
|---|---|---|---|---|
| 4,959,096 A * | 9/1990 | Zondler | ............... | C07D 409/12 514/356 |
| 4,966,908 A * | 10/1990 | Eckhardt | ............... | C07D 413/12 514/340 |
| 4,968,344 A * | 11/1990 | Kunz | .................. | C07D 213/83 514/277 |
| 4,980,355 A * | 12/1990 | Zondler | ............... | C07D 401/12 514/256 |
| 5,583,151 A * | 12/1996 | Lunkenheimer | ..... | C07D 213/81 514/354 |

(Continued)

FOREIGN PATENT DOCUMENTS

| | | | |
|---|---|---|---|
| CL | 2019002025 A1 | 12/2019 | |
| CL | 2019002661 A1 | 12/2019 | |

(Continued)

OTHER PUBLICATIONS

Patani, G. et al. "Bioisosterism: A rational approach in drug design" Chem. Rev., 1996, 96(8), 3147-3176. (Year: 1996).*

(Continued)

*Primary Examiner* — Erin E Hirt
(74) *Attorney, Agent, or Firm* — Jon E. Gordon; Haug Partners LLP

(57) ABSTRACT

A plant disease control agent which contains a compound represented by formula (1) as an active ingredient.

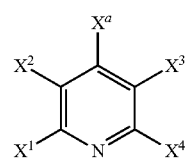

(1)

20 Claims, No Drawings

(56) References Cited

U.S. PATENT DOCUMENTS

| | | | | |
|---|---|---|---|---|
| 5,849,767 | A | * | 12/1998 | Kurahashi ............ C07D 401/06 |
| | | | | 546/274.7 |
| 6,281,231 | B1 | * | 8/2001 | Asada .................... A01N 47/20 |
| | | | | 514/277 |
| 2002/0010185 | A1 | * | 1/2002 | Cai .......................... A61P 1/00 |
| | | | | 514/255.06 |
| 2006/0121126 | A1 | * | 6/2006 | McFadden ............. A01N 65/00 |
| | | | | 514/26 |
| 2010/0137376 | A1 | * | 6/2010 | Komori ................. A01N 43/40 |
| | | | | 514/348 |

FOREIGN PATENT DOCUMENTS

| | | | | |
|---|---|---|---|---|
| CL | 2019002671 | A1 | | 12/2019 |
| CL | 2020000029 | A1 | | 7/2020 |
| CL | 2020000367 | A1 | | 8/2020 |
| CL | 2020000666 | A1 | | 8/2020 |
| CL | 2020001066 | A1 | | 10/2020 |
| CL | 2020001212 | A1 | | 10/2020 |
| EA | 23322 | B1 | | 5/2016 |
| EP | 0 268 775 | A1 | | 6/1988 |
| EP | 0 332 579 | A2 | | 9/1989 |
| EP | 0 334 813 | A2 | | 9/1989 |
| JP | 59135465 | A | * | 8/1984 ............ G03C 7/346 |
| JP | A-59-135465 | | | 8/1984 |
| JP | S63-57570 | | | 3/1988 |
| JP | A-63-093766 | | | 4/1988 |
| JP | A-01-272569 | | | 10/1989 |
| JP | A-01-283270 | | | 11/1989 |
| JP | A-09-136887 | | | 5/1997 |
| JP | A-09-165374 | | | 6/1997 |
| JP | A-10-095772 | | | 4/1998 |
| WO | WO 96/03047 | A1 | | 2/1996 |
| WO | WO-0164644 | A1 | * | 9/2001 ............ A01N 43/40 |
| WO | WO 2005/068430 | A1 | | 7/2005 |
| WO | WO 2008/016522 | A2 | | 2/2008 |
| WO | WO 2008/029084 | A1 | | 3/2008 |
| WO | WO 2008/098928 | A2 | | 8/2008 |
| WO | WO 2009/011305 | A1 | | 1/2009 |
| WO | WO 2010/132999 | A1 | | 11/2010 |
| WO | WO 2012/123416 | A1 | | 9/2012 |
| WO | WO 2014/124988 | A1 | | 8/2014 |
| WO | WO 2016/089990 | | | 6/2016 |
| WO | WO-2016089990 | A1 | * | 6/2016 ........... A61K 31/167 |
| WO | WO 2016/144703 | A1 | | 9/2016 |
| WO | WO-2020050297 | A1 | * | 3/2020 ............ A01N 43/60 |

OTHER PUBLICATIONS

Cambridge Medchem (https://www.cambridgemedchemconsulting.com/resources/bioisoteres/, cached wayback machine Jan. 13, 2013), no pagination. (Year: 2013).*
Koyanagi, T. et al. "Chapter 2: Bioisosterism in Agrochemicals" 1995 From Baker et al. Synthesis and Chemistry of Agrochemicals IV ACS symposium series p. 15-24. (Year: 1995).*
Office Action mailed on Apr. 14, 2021 in corresponding Russian Application No. 2019132420 and its English Translation.
Search Report mailed on Nov. 11, 2020 in corresponding European Application No. 18768098.8.
Office Action mailed on Dec. 14, 2020 in corresponding Chile Application No. 2019-02636 and its English Translation.
R.F. White, Acetylsalicylic acid (aspirin) induces resistance to tobacco mosaic virus in tobacco, Virology, 99, 410 (1979).
Maiden, T. M. M. et al., Synthesis of Functionalized Pyridines via a Regioselective Oxazoline Promoted C—H Amidation Reaction, Organic Letters, 2016, vol. 18, No. 14, p. 3434-3437.
International Search Reportmailed Jun. 12, 2018 in corresponding International Application No. PCT/JP2018/010408 and its English translation.
Office Action mailed on Jan. 4, 2023 in corresponding Japanese Patent Application No. 2022-027255 and its English Translation.
Notice of Reasons for Rejection mailed on Nov. 30, 2021 in corresponding Japanese Application No. 2019-506288.

* cited by examiner

PLANT DISEASE CONTROL AGENT

TECHNICAL FIELD

The present invention relates to a plant disease control agent. More particularly, the present invention relates to a plant disease control agent, a novel compound, and a method for controlling plant disease. The present invention is the National Stage entry under 35 U.S.C. § 371 of International Application No. PCT/JP2018/010408 filed on Mar. 16, 2018, published on Sep. 20, 2018 under Publication Number WO 2018/169038 A1, which claims priority on the basis of Japanese Patent Application No. 2017-052072 filed in Japan on Mar. 17, 2017, and Japanese Patent Application No. 2017-216236 filed in Japan on Nov. 9, 2017, the contents of which are incorporated herein by reference.

BACKGROUND OF THE INVENTION

Plants have evolved and acquired physical and chemical resistance mechanisms against external pathogens. The physical resistance mechanism is, for example, coating, such as a wax layer or cuticle, or a cell wall, which serves as a penetration barrier against pathogens. On the other hand, the chemical resistance mechanism is a system which inhibits the growth of pathogenic bacteria, such as a resistance factor inherently in a plant, or a resistance factor inductively biosynthesized and accumulated therein.

Recently, in order to protect plants from disease, an external agent has been administered to activate a chemical resistance mechanism to improve the tolerance of the plant. Such an agent may be referred to as a resistance inducer, and various inducers have been examined so far. It is known that resistance against tobacco mosaic virus (TMV) is induced by treating tobacco with salicylic acid or acetylsalicylic acid, (see Non-Patent Document 1).

Thus, in terms of cultivating healthy plants and ensuring food, it is very useful that the resistance of plants is induced to protect the plants from infection of plant pathogens or plant pathogenic bacteria.

It has been disclosed that chlorine-substituted isonicotinic acid derivatives have plant disease controlling effects (Patent Documents 1 to 5). However, it is known that such compounds can cause damage or the plant disease control effects thereof are weak. In addition, regarding fluorine-substituted isonicotinic acid derivatives, similar plant disease control agents have been disclosed (Patent Documents 6 to 10), but there is no specific description relating to a plant disease control agent according to the present invention.

DOCUMENTS OF RELATED ART

Patent Documents

Patent Document 1: Japanese Unexamined Patent Application, First Publication No. Sho 63-93766
Patent Document 2: Japanese Unexamined Patent Application, First Publication No. Hei 1-283270
Patent Document 3: Japanese Unexamined Patent Application, First Publication No. Hei 9-165374
Patent Document 4: Japanese Unexamined Patent Application, First Publication No. Hei 10-95772
Patent Document 5: International Patent Application, Publication No. 2005-68430
Patent Document 6: International Patent Application, Publication No. 2008-098928
Patent Document 7: International Patent Application, Publication No. 96-03047
Patent Document 8: Japanese Unexamined Patent Application, First Publication No. Hei 1-272569
Patent Document 9: International Patent Application, Publication No. 2009-11305
Patent Document 10: International Patent Application, Publication No. 2014-124988

Nonpatent Documents

Nonpatent Document 1: R. F. White, Acetylsalicylic acid (aspirin) induces resistance to tobacco mosaic virus in tobacco, Virology, 99, 410 (1979)

SUMMARY OF THE INVENTION

Problems to be Solved by the Invention

The present invention aims to provide a plant disease control agent, a novel compound that reduce plant damage, and a method for controlling plant disease.

Means to Solve the Problems

As a result of intensive studies relating to a fluoro-substituted pyridine compound, the present inventors found that there are compounds which exhibit high resistance-inducing activities while reducing damage without exhibiting direct antimicrobial activities against plant pathogens, and thereby completing the present invention.

The present invention includes the following aspects. [1] A plant disease control agent containing a compound of formula (1) as an active ingredient.

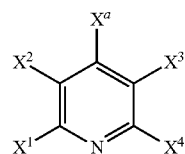

[In the formula (1), $X^1$ and $X^4$ are identical to or different from each other, represent a hydrogen atom, a fluorine atom, a chlorine atom or a trifluoromethyl group, at least one of $X^1$ and $X^4$ represents a fluorine atom or a trifluoromethyl group, $X^2$ and $X^3$ are identical to or different from each other, and represent a hydrogen atom, a fluorine atom, a chlorine atom or a methyl group, and, when one of $X^1$, $X^2$ and $X^4$ represents a fluorine atom, any one of the remaining two thereof does not represent a hydrogen atom,
$X^a$ represents a group of formula (2), (3), (4) or (5),

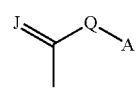

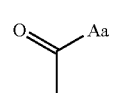

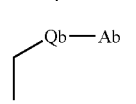

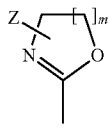

(5)

in the formula (2), J represents an oxygen atom or a sulfur atom,

A represents:
a C1-12 alkyl group which may be substituted with one to three groups selected from the group consisting of groups belonging to Group C, a thiol group, a methoxycarbonyl group, and a N-tert-butoxycarbonylamino group, a C2-8 alkenyl group which may be substituted with one to three groups selected from the groups belonging to Group C, a C2-8 alkynyl group which may be substituted with one to three groups selected from the groups belonging to Group C;

a C1-8 alkylcarbonyl group which may be substituted with one to three groups selected from the groups belonging to Group C, a C1-4 alkyloxy group which may be substituted with one to three groups selected from the groups belonging to Group C, a C1-8 alkylsulfonyl group which may be substituted with one to three groups selected from the groups belonging to Group C, a phenylcarbonyl group which may be substituted with one to four groups selected from the group consisting of groups belonging to Group D, a benzyl group, a phenyl group, and a phenoxy group, a phenylsulfonyl group which may be substituted with one to four groups selected from the groups belonging to Group D, a phenyl group which may be substituted with one to five groups selected from the group consisting of the groups belonging to Group D, a phenoxy group, and a benzyl group, a 5, 6, 7, 8-tetrahydronaphthyl group, a naphthyl group, a hetero ring group which may be substituted with one to four groups selected from the groups belonging to Group D (the hetero ring group being a group selected from Group E mentioned below), or a group of formula (2A) [in the formula (2A), $X^1$, $X^2$, $X^3$ and $X^4$ are the same as defined in the formula (1)],

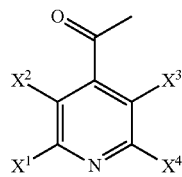

(2A)

wherein, when A represents the group of the formula (2A), Q represents a divalent group of formula: —O—(CH$_2$)$_n$—O—, a divalent group of formula: —NH—(CH$_2$)$_n$—O—, a divalent group of formula: —NH—(CH$_2$)$_n$—NH—, a divalent group of formula: —O—CH$_2$—CH=CH—CH$_2$—O—, a divalent group of formula: —NH—CH$_2$—CH=CH—CH$_2$—O—, a divalent group of formula: —NH—CH$_2$—CH=CH—CH$_2$—NH—, a cyclohexane-1,4-diyldioxy group, a cyclohexane-1,4-diyldiamino group, a divalent group of formula: —NH-(cyclohexane-1,4-diyl)-O—, a 1,3-phenylenediamino group, a 1,4-phenylenediamino group, a 1,4-phenylenedioxy group, a divalent group of formula: —NH-(1,4-phenylene)-O—, or a divalent group of formula (2B) [in the formula (2B), G represents an oxygen atom, a sulfur atom or a divalent group of formula: —SO$_2$-] (in which n represents an integer of 2 to 8), and

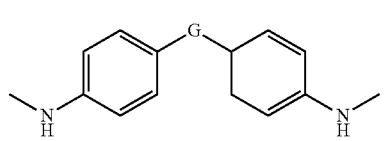

(2B)

when A does not represent the group of the formula (2A), Q represents an oxygen atom, a sulfur atom, a divalent group of formula: —NH—, or a divalent group of formula: —N(CH$_3$)—, in the formula (3), Aa represents a piperidin-1-yl group, a 1-methyl-1-1H-pyrrol-2-yl group, a morpholin-4-yl group, an indolin-1-yl group, a benzoisothiazo-3(2H)-one-1,1-dioxide-2-yl group, a piperazin-1-yl group, an azetidin-1-yl group, a 2,5-dioxopyrrolidin-1-yl group, a 3-oxoisothiazol-2(3H)-yl group, a benzo[d]isothiazol-2(3H)-yl group, a 1,1-dioxo-3-oxobenzo[d]isothiazol-2(3H)-yl group, a 5,6-dihydro-4H-1,3-oxazin-2-yl group, a 1H-pyrrol-2-yl group or an isoindolin-2-yl group, in the formula (4), Qb represents an oxygen atom, a sulfur atom, a divalent group of formula: —NH— or a divalent group of formula: —N(CH$_3$)—, Ab represents:
a C1-10 alkyl group which may be substituted with one to three groups selected from the group consisting of the groups belonging to Group C, a hydrogen atom, a methoxycarbonyl group, and a N-tert-butoxycarbonylamino group;

a C2-8 alkenyl group which may be substituted with one to three groups selected from the groups belonging to Group C, a C2-8 alkynyl group which may be substituted with one to three groups selected from the groups belonging to Group C;

a C1-8 alkylcarbonyl group which may be substituted with one to three groups selected from the groups belonging to Group C, a phenylcarbonyl group, or a hetero ring group which may be substituted with one to four groups selected from the groups belonging to Group D (the hetero ring group being a group selected from Group E mentioned below), in the formula (5), m represents an integer of 1 to 3, Z represents a hydrogen atom, a halogen atom or a methyl group, Group C consists of halogen atoms, a hydroxyl group, an amino group, a 5-methyl-1,3-dioxol-2-one-4-yl group, a phenylcarbonyl group, pyridyl groups which may be substituted with one to three groups selected from the groups belonging to Group D, and phenyl groups which may be substituted with one to four groups selected from the groups belonging to Group D, Group D consists of halogen atoms, a hydroxyl group, an amino group, a methylthio group, C1-4 alkyl groups which may be substituted with one to three halogen atoms, C1-4 alkyloxy groups which may be substituted with one to three halogen atoms, C1-4 alkylcarbonyl groups, a methoxycarbonyl group, an ethoxycarbonyl group, a benzylaminocarbonyl group, an acetoxy group, a nitro group, and a cyano group, and Group E consists of a pyridyl group, a thiazolyl group, a pyrazinyl group, a pyridazinyl group, an isothiazolyl group, an isoxazolyl group, a pyrimidinyl group, a benzimidazolyl group, a thienyl group, a furanyl group, a benzoxanyl group, a 2,3-dihydrobenzo[b][1,4]dioxin-6-yl group, a dihydrothiazolyl group, a benzothiazolyl group, a benzoisothiazolyl group, a benzisothiazole-3(2H)-one-1,1-dioxidyl group, a dibenzofuranyl group, an isothiazolyl group, and a triazolyl group.]

[2] The plant disease control agent according to [1], wherein $X^1$, $X^2$, $X^3$ and $X^4$ in the formula (1) are hydrogen atoms or fluorine atoms.

[3] The plant disease control agent according to [1] or [2], wherein, in the formula (1), $X^1$ and $X^4$ represent fluorine atoms, and $X^2$ or $X^3$ represents a hydrogen atom.

[4] The plant disease control agent according to any one of [1] to [3], wherein, in the formula (1), $X^1$ and $X^4$ represent fluorine atoms, and $X^2$ and $X^3$ represent hydrogen atoms.

[5] The plant disease control agent according to any one of [1] to [4], wherein J in the formula (2) represents an oxygen atom.

[6] The plant disease control agent according to any one of [1] to [5], wherein Q in the formula (2) represents a divalent group of formula: —NH—.

[7] The plant disease control agent according to any one of [1] to [5], wherein Q in the formula (2) represents an oxygen atom.

[8] The plant disease control agent according to any one of [1] to [7], wherein A in the formula (2) represents:

a C1-12 alkyl group which may be substituted with one to three groups selected from Group C;

a C2-8 alkenyl group which may be substituted with one to three groups selected from Group C;

a C2-8 alkynyl group which may be substituted with one to three groups selected from Group C;

a C1-8 alkylcarbonyl group which may be substituted with one to three groups selected from Group C;

a C1-4 alkyloxy group which may be substituted with one to three groups selected from Group C;

a phenylcarbonyl group which may be substituted with one to four groups selected from the group consisting of the groups belonging to Group D, a benzyl group, a phenyl group, and a phenoxy group;

a phenylsulfony group which may be substituted with one to four groups selected from Group D;

a phenyl group which may be substituted with one to five groups selected from the group consisting of the groups belonging to Group D, a phenoxy group and a benzyl group; or a hetero ring group which may be substituted with one to four groups selected from Group D (the hetero ring group being a group selected from Group E).

[9] A compound of formula (1) (excluding a compound of formula (2) wherein J and Q represent oxygen atoms, A represents a methyl group, an ethyl group or a cyclohexyl group, or a compound of the formula (2) wherein J represents an oxygen atom, Q represents a divalent group of formula: —NH—, and A represents a 3-chloro-4-fluorophenyl group),

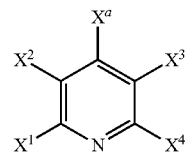

[in the formula (1), $X^1$ and $X^4$ are identical to or different from each other, represent a hydrogen atom, a fluorine atom, a chlorine atom or a trifluoromethyl group, at least one of $X^1$ and $X^4$ represents a fluorine atom or a trifluoromethyl group, $X^2$ and $X^3$ are identical to or different from each other, and represent a hydrogen atom, a fluorine atom, a chlorine atom or a methyl group, and, when one of $X^1$, $X^2$ and $X^4$ represents a fluorine atom, any one of the remaining two thereof does not represent a hydrogen atom, $X^a$ represents a group of formula (2), (3), (4) or (5),

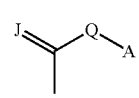

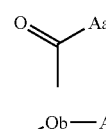

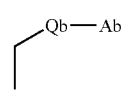

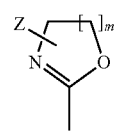

in the formula (2), J represents an oxygen atom or a sulfur atom,

A represents:

a C1-12 alkyl group which may be substituted with one to three groups selected from the group consisting of groups belonging to Group C, a thiol group, a methoxycarbonyl group, and a N-tert-butoxycarbonylamino group;

a C2-8 alkenyl group which may be substituted with one to three groups selected from the groups belonging to Group C, a C2-8 alkynyl group which may be substituted with one to three groups selected from the groups belonging to Group C;

a C1-8 alkylcarbonyl group which may be substituted with one to three groups selected from the groups belonging to Group C, a C1-4 alkyloxy group which may be substituted with one to three groups selected from the groups belonging to Group C, a C1-8 alkylsulfonyl group which may be substituted with one to three groups selected from the groups belonging to Group C, a phenylcarbonyl group which may be substituted with one to four groups selected from the group consisting of the groups belonging to Group D, a benzyl group, a phenyl group, and a phenoxy group, a phenylsulfonyl group which may be substituted with one to four groups selected from the groups belonging to Group D, a phenyl group which may be substituted with one to five groups selected from the group consisting of the groups belonging to Group D, a phenoxy group, and a benzyl group, a 5, 6, 7, 8-tetrahydronaphthyl group, a naphthyl group, a hetero ring group which may be substituted with one to four groups selected from the groups belonging to Group D (the hetero ring group being a group selected from Group E mentioned below), or a group of formula (2A) [in the formula (2A), $X^1$, $X^2$, $X^3$ and $X^4$ are the same as defined in the formula (1)],

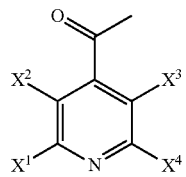

(2A)

wherein, when A represents the group of the formula (2A), Q represents a divalent group of formula: —O—$(CH_2)_n$—O—, a divalent group of formula: —NH—$(CH_2)_n$—O—, a divalent group of formula: —NH—$(CH_2)_n$—NH—, a divalent group of formula: —O—$CH_2$—CH═CH—$CH_2$—O—, a divalent group of formula: —NH—$CH_2$—CH═CH—$CH_2$—O—, a divalent group of formula: —NH—$CH_2$—CH═CH—$CH_2$—NH—, a cyclohexane-1,4-diyldioxy group, a cyclohexane-1,4-diyldiamino group, a divalent group of formula: —NH-(cyclohexane-1,4-diyl)-O—, a 1,3-phenylenediamino group, a 1,4-phenylenediamino group, a 1,4-phenylenedioxy group, a divalent group of formula: —NH-(1,4-phenylene)-O—, or a divalent group of formula (2B) [in the formula (2B), G represents an oxygen atom, a sulfur atom or a divalent group of formula: —$SO_2$-] (in which n represents an integer of 2 to 8),

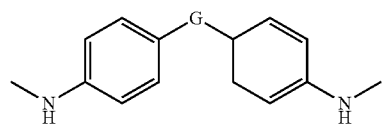

(2B)

when A does not represent the group of the formula (2A), Q represents an oxygen atom, a sulfur atom, a divalent group of formula: —NH—, or a divalent group of formula: —N($CH_3$)—, in the formula (3), Aa represents a piperidin-1-yl group, a morpholin-4-yl group, a piperazin-1-yl group, an azetidin-1-yl group, a 2,5-dioxopyrrolidin-1-yl group, a 3-oxoisothiazol-2(3H)-yl group, a benzo[d]isothiazol-2(3H)-yl group, a 1,1-dioxo-3-oxobenzo[d]isothiazol-2(3H)-yl group, a 5,6-dihydro-4H-1,3-oxazin-2-yl group, a 1H-pyrrol-2-yl group or an isoindolin-2-yl group, in the formula (4), Qb represents an oxygen atom, a sulfur atom, a divalent group of formula: —NH— or a divalent group of formula: —N($CH_3$)—, Ab represents:

a C1-10 alkyl group which may be substituted with one to three groups selected from the group consisting of groups belonging to Group C, a methoxycarbonyl group, and a N-tert-butoxycarbonylamino group;

a C2-8 alkenyl group which may be substituted with one to three groups selected from the groups belonging to Group C, a C2-8 alkynyl group which may be substituted with one to three groups selected from the groups belonging to Group C;

a C1-8 alkylcarbonyl group which may be substituted with one to three groups selected from the groups belonging to Group C, or a hetero ring group which may be substituted with one to four groups selected from the groups belonging to Group D (the hetero ring group being a group selected from Group E mentioned below), in the formula (5), m represents an integer of 1 to 3, Z represents a hydrogen atom, a halogen atom or a methyl group, Group C consists of halogen atoms, a hydroxyl group, an amino group, a 5-methyl-1,3-dioxol-2-one-4-yl group, a phenylcarbonyl group, pyridyl groups which may be substituted with one to three groups selected from the groups belonging to Group D, and phenyl groups which may be substituted with one to four groups selected from the groups belonging to Group D, Group D consists of halogen atoms, a hydroxyl group, an amino group, a methylthio group, C1-4 alkyl groups which may be substituted with one to three halogen atoms, C1-4 alkyloxy groups which may be substituted with one to three halogen atoms, C1-4 alkylcarbonyl groups, a methoxycarbonyl group, an ethoxycarbonyl group, a benzylaminocarbonyl group, an acetoxy group, a nitro group, and a cyano group, and Group E consists of a pyridyl group, a thiazolyl group, a pyrazinyl group, a pyridazinyl group, an isothiazolyl group, an isoxazolyl group, a pyrimidinyl group, a benzimidazolyl group, a thienyl group, a furanyl group, a benzoxanyl group, a 2,3-dihydrobenzo[b][1,4]dioxin-6-yl group, a dihydrothiazolyl group, a benzothiazolyl group, a benzoisothiazolyl group, a benzisothiazole-3(2H)-one-1,1-dioxidyl group, a dibenzofuranyl group, an isothiazolyl group, and a triazolyl group.]

[10] The compound according to [9], wherein $X^1$, $X^2$, $X^3$ and $X^4$ in the formula (1) are hydrogen atoms or fluorine atoms.

[11] The compound according to [9] or [10], wherein, in the formula (1), $X^1$ and $X^4$ represent fluorine atoms, and $X^2$ or $X^3$ represents a hydrogen atom.

[12] The compound according to any one of [9] to [11], wherein, in the formula (1), $X^1$ and $X^4$ represent fluorine atoms, and $X^2$ and $X^3$ represent hydrogen atoms.

[13] The compound according to any one of [9] to [12], wherein J in the formula (2) represents an oxygen atom.

[14] The compound according to any one of [9] to [13], wherein Q in the formula (2) represents a divalent group of formula: —NH—.

[15] The compound according to any one of [9] to [13], wherein Q in the formula (2) represents an oxygen atom.

[16] The compound according to any one of [9] to [15], wherein A in the formula (2) represents:

a C1-12 alkyl group which may be substituted with one to three groups selected from Group C;

a C2-8 alkenyl group which may be substituted with one to three groups selected from Group C;

a C2-8 alkynyl group which may be substituted with one to three groups selected from Group C;
a C1-8 alkylcarbonyl group which may be substituted with one to three groups selected from Group C;
a C1-4 alkyloxy group which may be substituted with one to three groups selected from Group C;
a phenylcarbonyl group which may be substituted with one to four groups selected from the group consisting of the groups belonging to Group D, a benzyl group, a phenyl group, and a phenoxy group;
a phenylsulfony group which may be substituted with one to four groups selected from Group D;
a phenyl group which may be substituted with one to five groups selected from the group consisting of the groups belonging to Group D, a phenoxy group and a benzyl group; or
a hetero ring group which may be substituted with one to four groups selected from Group D (the hetero ring group being a group selected from Group E).

[17] A method for controlling plant disease containing: contacting the plant disease control agent of any one of [1] to [8] or the compound of any one of [9] to [16] with a plant body or a seed, or formulating the plant disease control agent or the compound in a cultivation bed.

The present invention also includes the following embodiments.

[P1] A plant disease control agent containing, as an active ingredient, a fluoro-substituted pyridine compound of formula (P1):

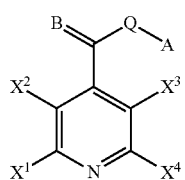

(P1)

[in the formula (P1), A represents:
a C1-10 alkyl group which may be substituted with one to three groups selected from the group consisting of "a thiol group, a methoxycarbonyl group, a N-tert-butoxycarbonylamino group, and groups belonging to Group C";
a C2-8 alkenyl group which may be substituted with one to three groups selected from Group C;
a C2-8 alkynyl group which may be substituted with one to three groups selected from Group C;
a C1-8 alkylcarbonyl group which may be substituted with one to three groups selected from Group C;
a C1-4 alkyloxy group which may be substituted with one to three groups selected from Group C;
a phenylcarbonyl group which may be substituted with one to four groups selected from the group consisting of "groups belonging to Group D, a benzyl group, a phenyl group, and a phenoxy group";
a C1-8 alkylsulfonyl group which may be substituted with one to three groups selected from Group C;
a phenylsulfonyl group which may be substituted with one to four groups selected from Group D;
a phenyl group which may be substituted with one to three groups selected from the group consisting of "the groups belonging to Group D, a phenoxy group, and a benzyl group";

a 5, 6, 7, 8-tetrahydronaphthyl group;
a hetero ring group which may be substituted with one to four groups selected from Group D (the hetero ring group being a group belonging to Group E), or
a group of formula (P2):

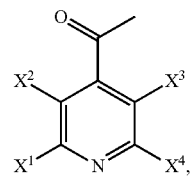

(P2)

Group C consists of halogen atoms, a hydroxyl group, an amino group, a 5-methyl-1,3-dioxol-2-one-4-yl group, and phenyl groups which may be substituted with one to four groups selected from Group D, Group D consists of halogen atoms, C1-4 alkyl groups which may be substituted with one to three halogen atoms, C1-4 alkyloxy groups which may be substituted with one to three halogen atoms, a methoxycarbonyl group, an ethoxycarbonyl group, a benzylaminocarbonyl group, a nitro group, and a cyano group, Group E consists of a pyridyl group, a thiazolyl group, a pyrazinyl group, a pyridazinyl group, an isothiazolyl group, an isoxazolyl group, a pyrimidinyl group, a benzimidazolyl group, a thienyl group, a furanyl group, a benzoxanyl group, a benzoisothiazolyl group, a benzisothiazole-3(2H)-one-1,1-dioxidyl group, a dibenzofuranyl group, and a triazolyl group, B represents an oxygen atom or a sulfur atom, Q represents an oxygen atom, a sulfur atom, a divalent group of formula: —NH—, or a divalent group of formula: —N(CH$_3$)—, when A represents a group of formula (P2), Q represents a divalent group of formula: —O—(CH$_2$)$_n$—O—, a divalent group of formula: —NH—(CH$_2$)$_n$—O—, a divalent group of formula: —NH—(CH$_2$)$_n$—NH—, a divalent group of formula: —O—CH$_2$—CH=CH—CH$_2$—O—, a divalent group of formula: —NH—CH$_2$—CH=CH—CH$_2$—O—, a divalent group of formula: —NH—CH$_2$—CH=CH—CH$_2$—NH—, a cyclohexane-1,4-diyldioxy group, a cyclohexane-1,4-diyldiamino group, a divalent group of formula: —NH-(cyclohexane-1,4-diyl)-O—, a 1,4-phenylenediamino group, a 1,4-phenylenedioxy group, a divalent group of formula: —NH-(1,4-phenylene)-O—, or a divalent group of formula (P3):

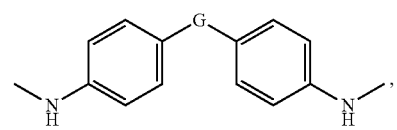

(P3)

wherein G represents an oxygen atom, a sulfur atom or a divalent group of formula: —SO$_2$—, n represents an integer of 2 to 8, $X_1$ and $X_4$ may be the same as or different from each other, and represents a hydrogen atom, a fluorine atom, a chlorine atom or a trifluoromethyl group, provided that any one thereof represents a fluorine atom or a trifluoromethyl group, $X_2$ and $X_3$ may be the same as or different from each other, and represents a hydrogen atom, a chlorine atom, a fluorine atom or a methyl group, provided that, when any one of $X_1$, $X_2$ and $X_4$ represents a fluorine atom, any one of the remaining two thereof does not represents a hydrogen atom], formula (P4):

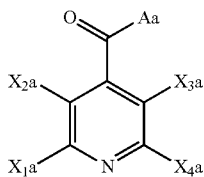

(P4)

[in the formula (P4), Aa represents a piperidin-1-yl group, a morpholin-4-yl group, a piperazin-1-yl group, an azetidin-1-yl group, a 2,5-dioxopyrrolidin-1-yl group, a 3-oxoisothiazol-2(3H)-yl group, a benzo[d]isothiazol-2(3H)-yl group, a 1,1-dioxo-3-oxobenzo[d]isothiazol-2(3H)-yl group, a 5,6-dihydro-4H-1,3-oxazin-2-yl group, a 1H-pyrrol-2-yl group or an isoindolin-2-yl group, $X_{1a}$ and $X_{4a}$ represents a hydrogen atom, a fluorine atom, a chlorine atom or a trifluoromethyl group, provided that any one thereof represents a fluorine atom or a trifluoromethyl group, $X_{2a}$ and $X_{3a}$ represents a hydrogen atom, a chlorine atom, a fluorine atom or a methyl group], formula (P5):

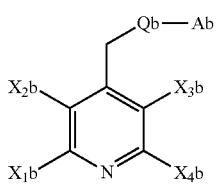

(P5)

[in the formula (P5), Qb represents an oxygen atom, a sulfur atom, a divalent group of formula: —NH— or a divalent group of formula: —N(CH$_3$)—, Ab represents: a hydrogen atom, a C1-10 alkyl group which may be substituted with one to three groups selected from the group consisting of "a methoxycarbonyl group, a N-tert-butoxycarbonylamino group, and the groups belonging to Group C";

a C2-8 alkenyl group which may be substituted with one to three groups selected from Group C;

a C2-8 alkynyl group which may be substituted with one to three groups selected from Group C;

a C1-8 alkylcarbonyl group which may be substituted with one to three groups selected from Group C;

a phenylcarbonyl group; or a hetero ring group selected from Group E, which may be substituted with one to four groups selected from Group D, Group D and Group E are as defined above, $X_1b$ and $X_4b$ represent a hydrogen atom, a fluorine atom, or a chlorine atom, provided that any one thereof represents a fluorine atom, and $X_2b$ and $X_3b$ represent a hydrogen atom, a chlorine atom, a fluorine atom or a methyl group], or, formula (P6):

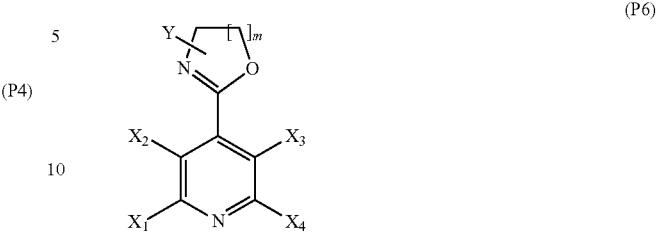

(P6)

[in the formula (P6), $X_1$, $X_2$, $X_3$ and $X_4$ are the same as defined above, m represents an integer of 1 to 3, and Y represents a hydrogen atom, a halogen atom or a methyl group].

[P2] The plant disease control agent according to [P], wherein $X_1$, $X_2$, $X_3$ and $X_4$ in the formula (P1) are hydrogen atoms or fluorine atoms.

[P3] The plant disease control agent according to [P1], wherein, in the formula (P1), $X_1$ and $X_4$ are fluorine atoms, and one of $X_2$ and $X_3$ is a hydrogen atom.

[P4] The plant disease control agent according to [P1], wherein, in the formula (P1), $X_1$ and $X_4$ represent fluorine atoms, and $X_2$ and $X_3$ represent hydrogen atoms.

[P5] The plant disease control agent according to any one of [P1] to [P4], wherein B in the formula (P1) described in [P1] represents an oxygen atom.

[P6] The plant disease control agent according to any one of [P1] to [P5], wherein Q in the formula (P1) described in [P1] represents a divalent group of formula: —NH—.

[P7] A plant disease control agent according to any one of [P1] to [P6], wherein A in the formula (P1) described in [P1] represents:

a C1-10 alkyl group which may be substituted with one to three groups selected from Group C;

a C2-8 alkenyl group which may be substituted with one to three groups selected from Group C;

a C2-8 alkynyl group which may be substituted with one to three groups selected from Group C;

a C1-8 alkylcarbonyl group which may be substituted with one to three groups selected from Group C;

a C1-4 alkyloxy group which may be substituted with one to three groups selected from Group C;

a phenylcarbonyl group which may be substituted with one to four groups selected from the group consisting of "the groups belonging to Group D, a benzyl group, a phenyl group, and a phenoxy group";

a phenylsulfonyl group which may be substituted with one to four groups selected from Group D;

a phenyl group which may be substituted with one to three groups selected from the group consisting of "the groups belonging to Group D, a phenoxy group, and a benzyl group"; or a hetero ring selected from Group E, which may be substituted with one to four groups selected from Group D;

Group D consists of halogen atoms, C1-4 alkyl groups which may be substituted with one to three halogen atoms, C1-4 alkyloxy groups which may be substituted with one to three halogen atoms, a methoxycarbonyl group, an ethoxycarbonyl group, a nitro group, and a cyano group, and Group E consists of a pyridyl group, a thiazolyl group, a pyrazinyl group, a pyridazinyl group, an isothiazolyl group, an isoxazolyl group, a pyrimidinyl group, a benzimidazolyl group, a thienyl group, a furanyl group, a benzoxanyl group, a benzoisothiazolyl group, a benzoisothiazole-3(2H)-one-1,1-dioxidyl group.

[P8] A fluoro-substituted pyridine compound represented by formula (P1):

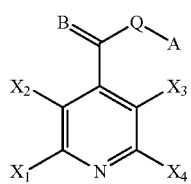

(P1)

[in the formula (P1), A represents:

a C1-10 alkyl group which may be substituted with one to three groups selected from the group consisting of "a thiol group, a methoxycarbonyl group, a N-tert-butoxycarbonylamino group, and groups belonging to Group C";

a C2-8 alkenyl group which may be substituted with one to three groups selected from Group C;

a C2-8 alkynyl group which may be substituted with one to three groups selected from Group C;

a C1-8 alkylcarbonyl group which may be substituted with one to three groups selected from Group C;

a C1-4 alkyloxy group which may be substituted with one to three groups selected from Group C;

a phenylcarbonyl group which may be substituted with one to four groups selected from the group consisting of "the groups belonging to Group D, a benzyl group, a phenyl group, and a phenoxy group";

a C1-8 alkylsulfonyl group which may be substituted with one to three groups selected from Group C;

a phenylsulfonyl group which may be substituted with one to four groups selected from Group D;

a phenyl group which may be substituted with one to three groups selected from the group consisting of "the groups belonging to Group D, a phenoxy group, and a benzyl group";

a 5, 6, 7, 8-tetrahydronaphthyl group;

a hetero ring group which may be substituted with one to four groups selected from Group D (the hetero ring group being a group belonging to Group E), or a group of formula (P2):

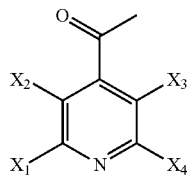

(P2)

Group C consists of halogen atoms, a hydroxyl group, an amino group, a 5-methyl-1,3-dioxol-2-one-4-yl group, and phenyl groups which may be substituted with one to four groups selected from Group D, Group D consists of halogen atoms, C1-4 alkyl groups which may be substituted with one to three halogen atoms, C1-4 alkyloxy groups which may be substituted with one to three halogen atoms, a methoxycarbonyl group, an ethoxycarbonyl group, a benzylaminocarbonyl group, a nitro group, and a cyano group, Group E consists of a pyridyl group, a thiazolyl group, a pyrazinyl group, a pyridazinyl group, an isothiazolyl group, an isoxazolyl group, a pyrimidinyl group, a benzimidazolyl group, a thienyl group, a furanyl group, a benzoxanyl group, a benzoisothiazolyl group, a benzisothiazole-3(2H)-one-1,1-dioxidyl group, a dibenzofuranyl group, and a triazolyl group, B represents an oxygen atom or a sulfur atom, Q represents an oxygen atom, a sulfur atom, a divalent group of formula: —NH—, or a divalent group of formula: —N(CH$_3$)—, provided that, when A represents a group of the formula (P2), Q represents a divalent group of formula: —O—(CH$_2$)$_n$—O—, a divalent group of formula: —NH—(CH$_2$)$_n$—O—, a divalent group of formula: —NH—(CH$_2$)$_n$—NH—, a divalent group of formula: —O—CH$_2$—CH=CH—CH$_2$—O—, a divalent group of formula: —NH—CH$_2$—CH=CH—CH$_2$—O—, a divalent group of formula: —NH—CH$_2$—CH=CH—CH$_2$—NH—, a cyclohexane-1,4-diyldioxy group, a cyclohexane-1,4-diyldiamino group, a divalent group of formula: —NH-(cyclohexane-1,4-diyl)-O—, a 1,4-phenylenediamino group, a 1,4-phenylenedioxy group, a divalent group of formula: —NH-(1,4-phenylene)-O—, or a divalent group of formula (P3):

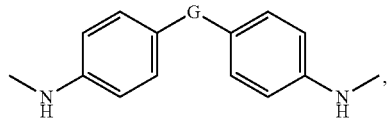

(P3)

wherein G represents an oxygen atom, a sulfur atom or a divalent group of formula: —SO$_2$—, n represents an integer of 2 to 8, X$_1$ and X$_4$ may be the same as or different from each other, and represent a hydrogen atom, a fluorine atom, a chlorine atom or a trifluoromethyl group, provided that any one thereof represents a fluorine atom or a trifluoromethyl group, X$_2$ and X$_3$ may be the same as or different from each other, and represent a hydrogen atom, a chlorine atom, a fluorine atom or a methyl group, provided that, when any one of X$_1$, X$_2$ and X$_4$ represents a fluorine atom, any one of the remaining two thereof does not represents a hydrogen atom], formula (P4):

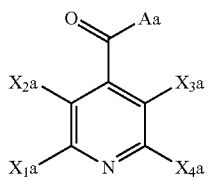

(P4)

[in the formula (P4), Aa represents a piperidin-1-yl group, a morpholin-4-yl group, a piperazin-1-yl group, an azetidin-1-yl group, a 2,5-dioxopyrrolidin-1-yl group, a 3-oxoisothiazol-2(3H)-yl group, a benzo[d]isothiazol-2(3H)-yl group, a 1,1-dioxo-3-oxobenzo[d]isothiazol-2(3H)-yl group, a 5,6-dihydro-4H-1,3-oxazin-2-yl group, a 1H-pyrrol-2-yl group or an isoindolin-2-yl group, X$_{1a}$ and X$_{4a}$ represent a hydrogen atom, a fluorine atom, a chlorine atom or a trifluoromethyl group, provided that any one thereof represents a fluorine atom or a trifluoromethyl group, $X_{2a}$ and $X_{3a}$ represents a hydrogen atom, a chlorine atom, a fluorine atom or a methyl group],
formula (P5):

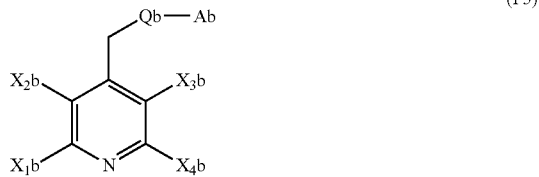

[in the formula (P5), Qb represents an oxygen atom, a sulfur atom, a divalent group of formula: —NH— or a divalent group of formula: —N(CH$_3$)—,
Ab represents:
a C1-10 alkyl group which may be substituted with one to three groups selected from the group consisting of "a methoxycarbonyl group, a N-tert-butoxycarbonylamino group, and the groups belonging to Group C";
a C2-8 alkenyl group which may be substituted with one to three groups selected from Group C;
a C2-8 alkynyl group which may be substituted with one to three groups selected from Group C;
a C1-8 alkylcarbonyl group which may be substituted with one to three groups selected from Group C;
a phenylcarbonyl group; or
a hetero ring group selected from Group E, which may be substituted with one to four groups selected from Group D,
Group D and Group E are the same as defined above,
$X_1b$ and $X_4b$ represents a hydrogen atom, a fluorine atom, or a chlorine atom, provided that any one thereof represents a fluorine atom, and
$X_2b$ and $X_3b$ represents a hydrogen atom, a chlorine atom, a fluorine atom or a methyl group], or
formula (P6):

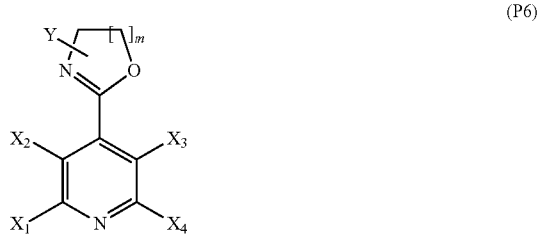

[in the formula (P6), $X_1$, $X_2$, $X_3$ and $X_4$ are the same as defined above,
m represents an integer of 1 to 3, and
Y represents a hydrogen atom, a halogen atom or a methyl group].
[P9] The fluoro-substituted pyridine compound according to [P8], wherein $X_1$, $X_2$, $X_3$ and $X_4$ in the formula (P1) are hydrogen atoms or fluorine atoms.
[P10] The fluoro-substituted pyridine compound according to [P8], wherein, in the formula (P1), $X_1$ and $X_4$ are fluorine atoms and one of $X_2$ and $X_3$ is a hydrogen atom.
[P11] The fluoro-substituted pyridine compound according to [P8], wherein, in the formula (P1), $X_1$ and $X_4$ are fluorine atoms and $X_2$ and $X_3$ are hydrogen atoms.
[P12] The fluoro-substituted pyridine compound according to any one of [P8] to [P11], wherein B in the formula (P1) described in [P8] is an oxygen atom.
[P13] The fluoro-substituted pyridine compound according to any one of [P8] to [P12], wherein Q in the formula (P1) described in [P8] represents a divalent group of formula: —NH—.
[P14] The fluoro-substituted pyridine compound according to any one of [P8] to [P13], wherein A in the formula (P1) described in [P8] represents:
a C1-10 alkyl group which may be substituted with one to three groups selected from Group C;
a C2-8 alkenyl group which may be substituted with one to three groups selected from Group C;
a C2-8 alkynyl group which may be substituted with one to three groups selected from Group C;
a C1-8 alkylcarbonyl group which may be substituted with one to three groups selected from Group C;
a C1-4 alkyloxy group which may be substituted with one to three groups selected from Group C;
a phenylcarbonyl group which may be substituted with one to four groups selected from the group consisting of "the groups belonging to Group D, a benzyl group, a phenyl group, and a phenoxy group";
a phenylsulfonyl group which may be substituted with one to four groups selected from Group D;
a phenyl group which may be substituted with one to three groups selected from the group consisting of "the groups belonging to Group D, a phenoxy group, and a benzyl group"; or
a hetero ring selected from Group E, which may be substituted with one to four groups selected from Group D;
Group D consists of halogen atoms, C1-4 alkyl groups which may be substituted with one to three halogen atoms, C1-4 alkyloxy groups which may be substituted with one to three halogen atoms, a methoxycarbonyl group, an ethoxycarbonyl group, a nitro group, and a cyano group,
Group E consists of a pyridyl group, a thiazolyl group, a pyrazinyl group, a pyridazinyl group, an isothiazolyl group, an isoxazolyl group, a pyrimidinyl group, a benzimidazolyl group, a thienyl group, a furanyl group, a benzoxanyl group, a benzoisothiazolyl group, and a benzoisothiazole-3(2H)-one-1,1-dioxidyl group.
[P15] A method for controlling plant disease, containing applying the plant disease control agent of any one of [P1] to [P7] or a fluoro-substituted pyridine compound of [P8] to [P14] to leaves and stems of plants, soils, the water surface of a rice filed in which rice is to be grown, carriers on which plants are to be grown, water of hydroponic culture (which may contain nutrients), roots of plants, rootstocks thereof, tuberosities thereof, bulbs thereof, germinated plants or seeds.

Effects of the Invention

According to the present invention, a plant disease control agent and a novel compound that can reduce plant damage, and a method for controlling plant disease are provided. The plant disease control agent and the novel compound according to the present invention have excellent resistance-inducing activities and are useful to control plant diseases.

EMBODIMENTS FOR CARRYING OUT THE INVENTION

In an embodiment, the present invention provides a plant disease control agent containing a compound of formula (1) as an active ingredient. In addition, in an embodiment, the present invention provides a compound of formula (1).

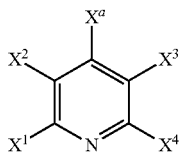

(1)

In the formula (1), $X^1$ and $X^4$ may be identical to or different from each other, and represent a hydrogen atom, a fluorine atom, a chlorine atom or a trifluoromethyl group, provided that any one of $X^1$ and $X^4$ represents a fluorine atom or a trifluoromethyl group. $X^2$ and $X^3$ may be identical to or different from each other, and represent a hydrogen atom, a fluorine atom, a chlorine atom or a methyl group, provided that, in the formula (1), when any one of $X^1$, $X^2$ and $X^4$ represents a fluorine atom, any one of the remaining two thereof does not represent a hydrogen atom.

It is preferable in the formula (1) that $X^1$ and $X^4$ be fluorine atoms, and $X^2$ and $X^3$ be hydrogen atoms or fluorine atoms.

In the formula (1), $X^a$ represents a group of formula (2), (3), (4) or (5).

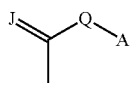

(2)

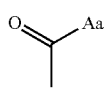

(3)

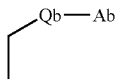

(4)

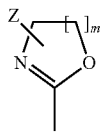

(5)

In the formula (2), J represents an oxygen atom or a sulfur atom. In addition, in the formula (2), A represents: a C1-12 alkyl group which may be substituted with one to three groups selected from the group consisting of groups belonging to Group C mentioned below, a thiol group, a methoxycarbonyl group, and a N-tert-butoxycarbonylamino group, a C2-8 alkenyl group which may be substituted with one to three groups selected from the groups belonging to Group C; a C2-8 alkynyl group which may be substituted with one to three groups selected from the groups belonging to Group C; a C1-8 alkylcarbonyl group which may be substituted with one to three groups selected from the groups belonging to Group C; a C1-4 alkyloxy group which may be substituted with one to three groups selected from the groups belonging to Group C; a C1-8 alkylsulfonyl group which may be substituted with one to three groups selected from the groups belonging to Group C; a phenylcarbonyl group which may be substituted with one to four groups selected from the group consisting of the groups belonging to Group D, a benzyl group, a phenyl group, and a phenoxy group; a phenylsulfonyl group which may be substituted with one to four groups selected from the groups belonging to Group D; a phenyl group which may be substituted with one to five groups selected from the group consisting of the groups belonging to Group D, a phenoxy group, and a benzyl group; a 5, 6, 7, 8-tetrahydronaphthyl group; a naphthyl group; a hetero ring group which may be substituted with one to four groups selected from the groups belonging to Group D (the hetero ring group being a group selected from Group E mentioned below); or a group of formula (2A) [in the formula (2A), $X^1$, $X^2$, $X^3$ and $X^4$ are the same as defined in the formula (1)].

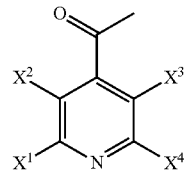

(2A)

in the formula (2), when A represents the group of the formula (2A), Q represents a divalent group of formula: —O—$(CH_2)_n$—O—, a divalent group of formula: —NH—$(CH_2)_n$—O—, a divalent group of formula: —NH—$(CH_2)_n$—NH—, a divalent group of formula: —O—$CH_2$—CH=CH—$CH_2$—O—, a divalent group of formula: —NH—$CH_2$—CH=CH—$CH_2$—O—, a divalent group of formula: —NH—$CH_2$—CH=CH—$CH_2$—NH—, a cyclohexane-1,4-diyldioxy group, a cyclohexane-1,4-diyldiamino group, a divalent group of formula: —NH-(cyclohexane-1,4-diyl)-O—, a 1,3-phenylenediamino group, a 1,4-phenylenediamino group, a 1,4-phenylenedioxy group, a divalent group of formula: —NH-(1,4-phenylene)-O—, or a divalent group of formula (2B) [in the formula (2B), G represents an oxygen atom, a sulfur atom or a divalent group of formula: —$SO_2$—] (in which n represents an integer of 2 to 8).

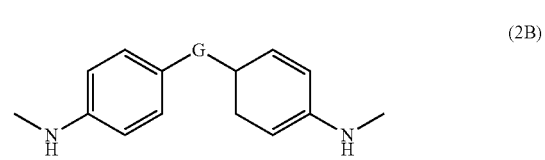

(2B)

In the formula (2), when A does not represent the group of the formula (2A), Q represents an oxygen atom, a sulfur atom, a divalent group of formula: —NH—, or a divalent group of formula: —N($CH_3$)—.

In the formula (3), Aa represents a piperidin-1-yl group, a 1-methyl-1-1H-pyrrol-2-yl group, a morpholin-4-yl group, an indolin-1-yl group, a benzoisothiazol-3(2H)-one-1,1-dioxide-2-yl group, a piperazin-1-yl group, an azetidin-1-yl group, a 2,5-dioxopyrrolidin-1-yl group, a 3-oxoisothiazol-2(3H)-yl group, a benzo[d]isothiazol-2(3H)-yl group, a 1,1-dioxo-3-oxobenzo[d]isothiazol-2(3H)-yl group, a 5,6-dihydro-4H-1,3-oxazin-2-yl group, a 1H-pyrrol-2-yl group or an isoindolin-2-yl group.

In an embodiment, Aa in the formula (3) may be a group excepting, from Aa mentioned above, a 1-methyl-1-1H-pyrrol-2-yl group, an indolin-1-yl group, and a benzoisothiazol-3(2H)-one-1,1-dioxide-2-yl group.

In the formula (4), Qb represents an oxygen atom, a sulfur atom, a divalent group of formula: —NH— or a divalent group of formula: —N($CH_3$)—. In the formula (4), Ab represents: a C1-10 alkyl group which may be substituted with one to three groups selected from the group consisting of the groups belonging to Group C, a hydrogen atom, a methoxycarbonyl group, and a N-tert-butoxycarbonylamino group; a C2-8 alkenyl group which may be substituted with one to three groups selected from the groups belonging to Group C; a C2-8 alkynyl group which may be substituted with one to three groups selected from the groups belonging to Group C; a C1-8 alkylcarbonyl group which may be substituted with one to three groups selected from the groups belonging to Group C; a phenylcarbonyl group; or a hetero ring group which may be substituted with one to four groups selected from the groups belonging to Group D (the hetero ring group being a group selected from Group E mentioned below).

In an embodiment, Ab in the formula (4) may be any of groups formed by removing a hydrogen atom from Ab mentioned above.

In the formula (5), m represents an integer of 1 to 3, and Z represents a hydrogen atom, a halogen atom or a methyl group.

Group C consists of halogen atoms, a hydroxyl group, an amino group, a 5-methyl-1,3-dioxol-2-one-4-yl group, a phenylcarbonyl group, pyridyl groups which may be substituted with one to three groups selected from the groups belonging to Group D, and phenyl groups which may be substituted with one to four groups selected from the groups belonging to Group D.

Group D consists of halogen atoms, a hydroxyl group, an amino group, a methylthio group, C1-4 alkyl groups which may be substituted with one to three halogen atoms, C1-4 alkyloxy groups which may be substituted with one to three halogen atoms, C1-4 alkylcarbonyl groups, a methoxycarbonyl group, an ethoxycarbonyl group, a benzylaminocarbonyl group, an acetoxy group, a nitro group, and a cyano group.

Group E consists of a pyridyl group, a thiazolyl group, a pyrazinyl group, a pyridazinyl group, an isothiazolyl group, an isoxazolyl group, a pyrimidinyl group, a benzimidazolyl group, a thienyl group, a furanyl group, a benzoxanyl group, a 2,3-dihydrobenzo[b][1,4]dioxin-6-yl group, a dihydrothiazolyl group, a benzothiazolyl group, a benzoisothiazolyl group, a benzisothiazole-3(2H)-one-1,1-dioxidyl group, a dibenzofuranyl group, an isothiazolyl group, and a triazolyl group.

In an embodiment, the compound may be a compound excepting, from the compounds of formula (1), compounds in which J and Q are oxygen atoms, A is a methyl group, an ethyl group or a cyclohexyl group and compounds in which J is an oxygen atom, Q is a group represented by the formula: —NH—, and A is a 3-chloro-4-fluorophenyl group.

In the present embodiment, the term "C1-12 alkyl group" means a C1-12 linear, branched, or cyclic alkyl group. Examples of the C1-12 alkyl group include a methyl group, an ethyl group, a n-propyl group, an isopropyl group, a n-butyl group, a sec-butyl group, an isobutyl group, a tert-butyl group, a n-octyl group, a cyclopropyl group, a cyclobutyl group, a cyclopentyl group, and a cyclohexyl group, and preferable examples thereof include a methyl group, an ethyl group, a n-propyl group, an isopropyl group, an isobutyl group, a tert-butyl group, a cyclopropyl group, a cyclohexyl group, and a n-octyl group.

The term "C2-8 alkenyl group" means a linear, branched, or cyclic alkenyl group having at least one double bond at an arbitrary position of a C2-8 alkyl group. Examples of the C2-8 alkenyl group include an ethenyl group, a 1-propenyl group, a 2-propenyl group, a 2-butenyl group, an isopropenyl group, a 3-butenyl group, a 4-pentenyl group, a 5-hexenyl group, and a 1-cyclohexenyl group, and the C2-8 alkenyl group is preferably a 2-propenyl group.

The term "C2-8 alkynyl group" means a linear, branched, or cyclic alkynyl group having at least one triple bond at an arbitrary position of a C2-8 alkyl group. Examples of the C2-8 alkynyl group include an ethynyl group, a 1-propynyl group, a 2-propynyl group, a 3-butynyl group, and a cyclopropylethynyl group, and the C2-8 alkynyl group is preferably a 2-propynyl group.

The term "C1-4 alkyloxy group" means an oxygen atom substituted with a C1-4 linear, branched, or cyclic alkyl group. Examples of the C1-4 alkyloxy group include a methoxy group, an ethoxy group, a n-propoxy group, an iso-propyloxy group, a n-butoxy group, a sec-butoxy group, an isobutoxy group, a tert-butoxy group, a cyclopropyloxy group, and a cyclobutyloxy group, and the C1-4 alkyloxy group is preferably a methoxy group.

The term "C1-8 alkylcarbonyl group" means a carbonyl group substituted with a C1-8 linear, branched, or cyclic alkyl group. Examples of the C1-8 alkylcarbonyl group include an ethylcarbonyl group, a n-propylcarbonyl group, an iso-propylcarbonyl group, a n-butylcarbonyl group, a sec-butylcarbonyl group, an isobutylcarbonyl group, a tert-butylcarbonyl group, a n-octylcarbonyl group, a cyclopropylcarbonyl group, a cyclobutylcarbonyl group, a cyclopentylcarbonyl group, and a cyclohexylcarbonyl group.

The term "C1-8 alkylsulfonyl group" means a sulfonyl group substituted with a C1-8 linear, branched, or cyclic alkyl group. Examples of the C1-8 alkylsulfonyl group include a methylsulfonyl group, an ethylsulfonyl group, a n-propylsulfonyl group, an iso-propylsulfonyl group, a n-butylsulfonyl group, a sec-butylsulfonyl group, an isobutylsulfonyl group, a tert-butylsulfonyl group, a n-octylsulfonyl group, a cyclopropylsulfonyl group, a cyclobutylsulfonyl group, a cyclopentylsulfonyl group, and a cyclohexylsulfonyl group.

Examples of the 5, 6, 7, 8-tetrahydronaphthyl group include a 5,6,7,8-tetrahydronaphthalen-1-yl group, and a 5,6,7,8-tetrahydronaphthalen-2-yl group.

Examples of the halogen atom include a fluorine atom, a chlorine atom, a bromine atom and an iodine atom.

The divalent group of formula: —NH-(cyclohexane-1,4-diyl)-O— is a divalent group in which a group represented by formula: —NH— and an oxygen atom are bonded at the first position and the fourth position of a cyclohexane ring, respectively.

The divalent group of formula: —NH-(1,4-phenylene)-O— is a divalent group in which a group represented by formula: —NH— and an oxygen atom are bonded at the first position and the fourth position of a benzene ring, respectively.

In the present specification, the symbol "-" which bonds atoms and/or groups in the formulae represents a single bond, and the symbol "=" represents a double bond, unless otherwise indicated. For example, in the formula (1), the symbol "-" represents a single bond, and the symbol "=" represents a double bond. For example, in the case where Q in the formula (2) represents a divalent group of formula: —O—(CH$_2$)$_n$—O—, a divalent group of formula: —NH—(CH$_2$)$_n$—O—, a divalent group of formula: —NH—(CH$_2$)—NH—, a divalent group of formula: —O—CH$_2$—CH=CH—CH$_2$—O—, a divalent group of formula: —NH—CH$_2$—CH=CH—CH$_2$—O—, a divalent group of formula: —NH—CH$_2$—CH=CH—CH$_2$—NH—, a cyclohexane-1,4-diyldioxy group, a cyclohexane-1,4-diyldiamino group, a divalent group of formula: —NH-(cyclohexane-1, 4-diyl)-O—, a 1,3-phenylenediamino group, a 1,4-phenylenediamino group, a 1,4-phenylenedioxy group, a divalent group of formula: —NH-(1,4-phenylene)-O—, or a divalent group of formula (2B), the symbol "-" in these groups represents a single bond, and the symbol "=" represents a double bond.

In Group D, examples of the C1-4 alkyl group which may be substituted with one to three halogen atoms include a methyl group, an ethyl group, a n-propyl group, an isopropyl group, a n-butyl group, a sec-butyl group, an isobutyl group, a tert-butyl group, a trifluoromethyl group, a chloromethyl group, a methoxy group, and an ethoxy group.

In Group D, examples of the C1-4 alkyloxy group which may be substituted with one to three halogen atoms include a methoxy group, an ethoxy group, a n-propyloxy group, an iso-propyloxy group, a n-butyloxy group, a sec-butyloxy group, an isobutyloxy group, a tert-butyloxy group, a trifluoromethyloxy group, and a chloromethyloxy group.

A in the formula (2) preferably represents: a C1-4 alkyl group which may be substituted with one to three groups selected from the groups belonging to Group C; a C2-3 alkenyl group which may be substituted with one to three groups selected from the groups belonging to Group C; a C2-3 alkynyl group which may be substituted with one to three groups selected from the groups belonging to Group C, or a phenyl group which may be substituted with one to three groups selected from the groups belonging to Group D.

In the formula (2), J more preferably represents an oxygen atom.

In the formula (2), Q more preferably represents an oxygen atom or a divalent group of formula: —NH—.

There is a case where the compound of formula (1) exists as a hydrate or an arbitrary solvate, and the hydrate or the solvate is encompassed in the present embodiment. In addition, there is a case where the compound of formula (1) has an asymmetric carbon, the asymmetric carbon may be in an arbitrary configuration. Stereoisomers such as optical isomers in pure form based on the asymmetric carbon or diastereoisomers, mixtures of any stereoisomers, racemates, and the like are included in the present embodiment. The compound of the formula (1) may have at least one double bond, and geometric isomers derived from the double bond or a ring structure may present. Mixtures of any of the geometric isomers or any geometrical isomers in pure form are also encompassed by the present embodiment.

Next, the methods for preparing the compound according to the present embodiment will be explained. Although the compound according to the present embodiment may be prepared by the below-mentioned methods A to K, for example, the preparation method of the compound according to the present embodiment is not intended to be limited to these.

[Method A]

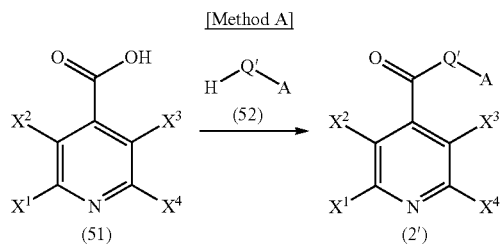

Among the compounds of the formula (1), a compound of formula (2') is prepared by reacting a compound of formula (51) (in the formula (51), $X^1$, $X^2$, $X^3$ and $X^4$ are the same as defined in the formula (1)) and a compound of formula (52) (in the formula (52), A is the same as defined in the formula (2), Q' is an oxygen atom, a sulfur atom, a divalent group of formula: —NH—, or a divalent group of formula: —N(CH$_3$)—) in the presence or absence of a base and in the presence of a condensing agent.

As the compound of the formula (51), which is a starting material, a commercially available reagent may be used or a synthesize compound may be used. The compound of the formula (51) may be synthesized by the method described in Japanese Unexamined Patent Application, First Publication No. Sho 63-93766, Japanese Unexamined Patent Application, First Publication No. Hei 1-283270, R. E. Banks, et al., Heterocyclic polyfluoro-compounds. Part XII. Synthesis and some reactions of 2,3,5,6-tetrafluoro-4-iodopyridine, J. Chem. Soc. (C), 2091-2095 (1967), or the like.

Examples of a solvent to be used in the reaction include dichloromethane, chloroform, acetonitrile, ethyl acetate, toluene, tetrahydrofuran, N,N-dimethylformamide, N-methylpyrrolidone and dimethyl sulfoxide.

Examples of the condensing agent to be used in the reaction include 1-ethyl-3-(3-dimethylaminopropyl)carbodiimide hydrochloride and 1,3-dicyclohexylcarbodiimide.

Examples of the base to be used in the reaction include 4-dimethylaminopyridine. The amount of the base to be used is within a range of 0.01 equivalents to 1.2 equivalents based on the carboxylic acid (51).

The amount of the condensing agent to be used is within a range of 1.0 equivalent to 1.2 equivalents based on the carboxylic acid (51). The amount of the compound of the formula (52) to be used is within a range of 1.0 equivalent to 1.2 equivalents based on the carboxylic acid (51).

The reaction temperature is selected within a range of 0° C. to 60° C., and preferably 10° C. to 40° C. The reaction time is, for example, within a range of 10 minutes to 24 hours, and preferably 30 minutes to 4 hours.

[Method B]

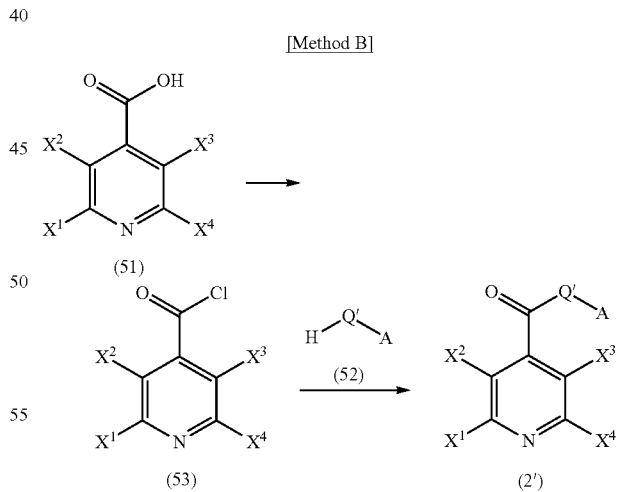

Among the compounds of formula (1), the compound of the formula (2') may also be prepared by the below-mentioned method in which the compound of the formula (2') is prepared from the compound of the formula (51) (in the formula (51), $X^1$, $X^2$, $X^3$ and $X_4$ are the same as defined in the formula (1)) via a compound of formula (53) (in the formula (53), $X^1$, $X^2$, $X^3$ and $X^4$ are the same as defined in the formula (1)).

In the first step, the compound of the formula (53) is prepared by chlorinating the compound of the formula (51).

Although tetrahydrofuran, toluene, ethyl acetate, dichloromethane, chloroform, or acetonitrile may be used in the reaction as a solvent, the reaction may be conducted in the absence of any solvents.

Examples of a chlorinating agent to be used in the reaction include thionyl chloride and oxalyl chloride. The amount of the chlorinating agent to be used is within a range of 1 equivalent to 5 equivalents based on the compound of the formula (51). The reaction temperature is, for example, −20° C. to 100° C., and more preferably 10° C. to 80° C. The reaction time is within a range of 10 minutes to 6 hours, and preferably 30 minutes to 2 hours.

Next, in the second step, the compound of the formula (2') may be prepared by reacting the compound of the formula (53) and the compound of the formula (52) in the presence of a base.

Examples of a solvent to be used in the reaction include tetrahydrofuran, toluene, ethyl acetate, acetonitrile, dichloromethane, chloroform, N,N-dimethylformamide, N-methylpyrrolidone, dimethyl sulfoxide and mixtures thereof.

Examples of the base to be used in the reaction include triethylamine, N,N-diisopropylethylamine, pyridine, 4-dimethylaminopyridine, sodium carbonate, and potassium carbonate. The amount of the base to be used is 1 equivalent to 10 equivalents based on the carboxylic acid chloride (53).

The amount of the compound of the formula (52) to be used is within a range of 1 equivalent to 2 equivalents based on the carboxylic acid chloride (53). The reaction temperature is, for example, within a range of −20° C. to 100° C., and preferably 10° C. to 50° C. The reaction time is within a range of 10 minutes to 6 hours, and preferably 30 minutes to 3 hours.

The compound of the formula (2') may also be prepared by adding a solvent, a chlorinating agent, the compound of the formula (52), and a base to the compound of the formula (51) to allow the reaction to proceed in the same container without isolating the compound of the formula (53).

[Method C]

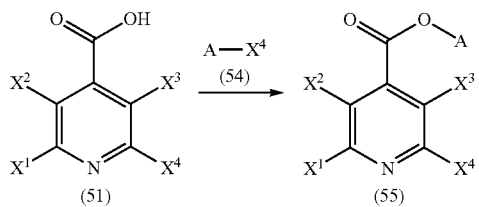

Among the compounds of the formula (1), a compound of formula (55) may be prepared by reacting the compound of the formula (51) (in the formula (51), $X^1$, $X^2$, $X^3$ and $X^4$ are the same as defined in the formula (1)) and a compound of formula (54) (in the formula (54), A is the same as defined in the formula (2), and $X^5$ is a halogen atom) in the presence of a base.

Examples of a solvent to be used in the reaction include tetrahydrofuran, toluene, ethyl acetate, acetonitrile, dichloromethane, chloroform, N,N-dimethylformamide, N-methylpyrrolidone, and dimethyl sulfoxide.

Examples of the base to be used in the reaction include sodium hydrogen carbonate, sodium carbonate, potassium carbonate, sodium hydroxide, and potassium hydroxide. The amount of the base to be used is within a range of 1.0 equivalent to 1.5 equivalents based on the carboxylic acid (51).

The amount of the compound of the formula (54) to be used is within a range of 1 equivalent to 2 equivalents based on the carboxylic acid (51). The reaction temperature is, for example, −20° C. to 120° C., and preferably 10° C. to 80° C. The reaction time is within a range of 10 minutes to 8 hours, and preferably 30 minutes to 6 hours.

[Method D]

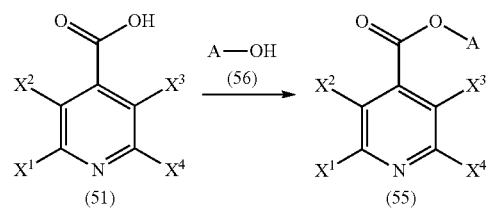

Among the compounds of formula (1), the compound of the formula (55) may also be prepared by reacting the compound of the formula (51) (in the formula (51), $X^1$, $X^2$, $X^3$ and $X^4$ are the same as defined in the formula (1)) and a compound of formula (56) (in the formula (56), A is the same as defined in the formula (2)) in the presence of an acid.

Although tetrahydrofuran, toluene, ethyl acetate, acetonitrile, dichloromethane, chloroform, N,N-dimethylformamide, N-methylpyrrolidone, or dimethyl sulfoxide may be used as a solvent in the reaction, the reaction may be conducted in the absence of any solvents.

The amount of the compound of the formula (56) to be used is within a range of 1 equivalent to 10 equivalents based on the carboxylic acid (51). Examples of the acid to be used in the reaction include sulfuric acid and hydrogen chloride. The amount of the acid to be used is within a range of 0.01 equivalents to 3 equivalents based on the carboxylic acid (51). The reaction temperature is, for example, −20° C. to 120° C., and preferably 10° C. to 90° C. The reaction time is within a range of 10 minutes to 8 hours, and preferably 30 minutes to 6 hours.

[Method E]

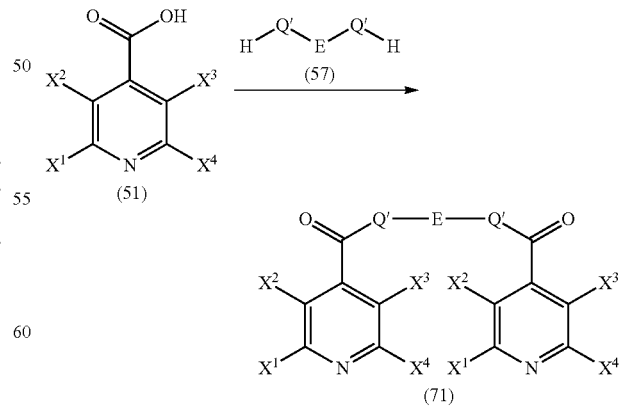

Among the compounds of formula (1), a compound of formula (71) may be prepared by reacting the compound of the formula (51) (in the formula (51), $X^1$, $X^2$, $X^3$ and $X^4$ are the same as defined in the formula (1)) and a compound of formula (57) (in the formula (57), Q' is an oxygen atom, a sulfur atom, a divalent group of formula: —NH— or a divalent group of formula: —N(CH₃)—, E is a divalent group of formula: —(CH₂)ₙ— (wherein n represents an integer of 2 to 4), a divalent group of formula: —CH₂—CH=CH—CH₂—, a cyclohexane-1,4-diyl group, a 1,4-phenylene group, or a divalent group of the below-mentioned formula (2B') (in the formula (2B'), G is an oxygen atom, a sulfur atom or a divalent group of formula: —SO₂—)) in the presence or absence of a base, and in the presence of a condensing agent.

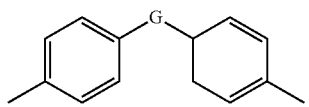

(2B')

Examples of a solvent to be used in the reaction include dichloromethane, chloroform, acetonitrile, ethyl acetate, toluene, tetrahydrofuran, N,N-dimethylformamide, N-methylpyrrolidone, and dimethyl sulfoxide.

Examples of the condensing agent to be used in the reaction include 1-ethyl-3-(3-dimethylaminopropyl)carbodiimide hydrochloride and 1,3-dicyclohexylcarbodiimide.

Examples of the base to be used in the reaction include 4-dimethylaminopyridine. The amount of the base to be used is within a range of 0.01 equivalents to 1.2 equivalents based on the carboxylic acid (51).

The amount of the condensing agent to be used is within a range of 1.0 equivalent to 1.2 equivalents based on the carboxylic acid (51). The amount of the compound of the formula (57) to be used is within a range of 0.5 equivalents to 0.6 equivalents based on the carboxylic acid (51). The reaction temperature is, for example, 0° C. to 60° C., and preferably 10° C. to 40° C. The reaction time is within a range of 10 minutes to 24 hours, and preferably 30 minutes to 18 hours.

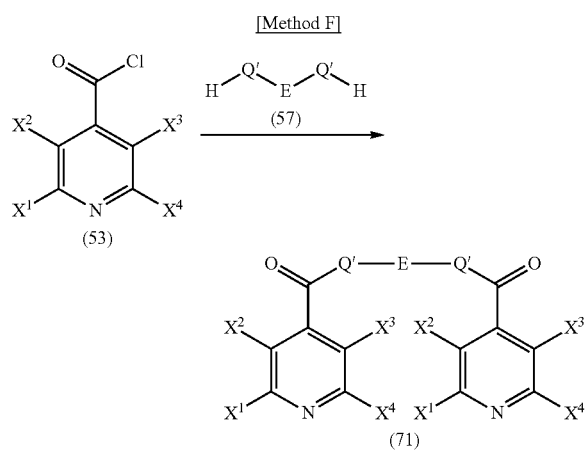

Among the compounds of the formula (1), the compound of the formula (71) may also be prepared by reacting the compound of the formula (53) (in the formula (53), X¹, X², X³ and X⁴ are the same as defined in the formula (1)) and the compound of the formula (57) (in the formula, Q' and E are the same as defined in the formula (57) described in the method E) in the presence of a base.

Examples of the solvent to be used in the reaction include tetrahydrofuran, toluene, ethyl acetate, acetonitrile, dichloromethane, chloroform, N,N-dimethylformamide, N-methylpyrrolidone, dimethyl sulfoxide and mixtures thereof.

Examples of the base to be used in the reaction include triethylamine, N,N-diisopropylethylamine, pyridine, 4-dimethylaminopyridine, sodium carbonate, and potassium carbonate. The amount of the base to be used is within a range of 1 equivalent to 10 equivalents based on the carboxylic acid chloride (53).

The amount of the compound of the formula (57) to be used is within a range of 0.5 equivalents to 0.6 equivalents based on the carboxylic acid chloride (53). The reaction temperature is, for example, within a range of −20° C. to 100° C., and preferably 10° C. to 50° C. The reaction time is within a range of 10 minutes to 6 hours, and preferably 30 minus to 4 hours.

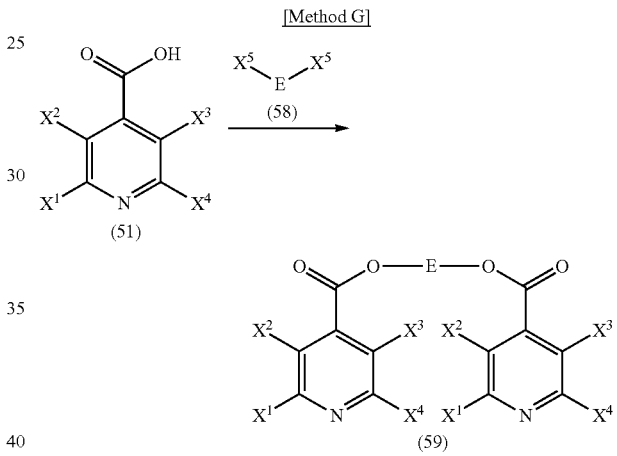

Among the compounds of formula (1), a compound of formula (59) may be prepared by reacting the compound of the formula (51) (in the formula (51), X¹, X², X³ and X⁴ are the same as defined in the formula (1)) and a compound of formula (58) (in the formula (58), X⁵ is a halogen atom, and E is the same as defined in the formula (57) as described in the method E) in the presence of a base.

Examples of a solvent to be used in the reaction include tetrahydrofuran, toluene, ethyl acetate, acetonitrile, dichloromethane, chloroform, N,N-dimethylformamide, N-methylpyrrolidone, and dimethyl sulfoxide.

Examples of the base to be used in the reaction include sodium hydrogen carbonate, sodium carbonate, potassium carbonate, sodium hydroxide, and potassium hydroxide. The amount of the base to be used is within a range of 1.0 equivalent to 1.1 equivalents based on the carboxylic acid (51).

The amount of the compound of the formula (58) to be used is within a range of 0.5 equivalents to 0.6 equivalents based on the carboxylic acid (51). The reaction temperature is within a range of −20° C. to 120° C., and preferably 10° C. to 80° C. The reaction time is within a range of 10 minutes to 8 hours, and preferably 30 minutes to 6 hours.

[Method H]

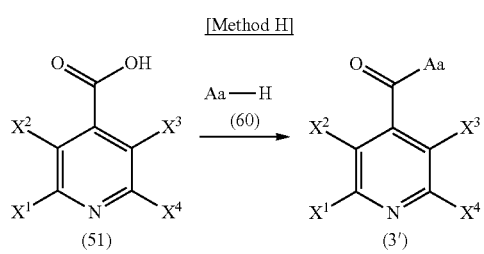

Among the compounds of formula (1), a compound of formula (3') may be prepared by reacting the compound of the formula (51) (in the formula (51), $X^1$, $X^2$, $X^3$ and $X^4$ are the same as defined in the formula (1)) and a compound of formula (60) (in the formula (60), Aa is the same as defined in the formula (3)) in the presence or absence of a base, and in the presence of a condensing agent.

Examples of a solvent to be used in the reaction include dichloromethane, chloroform, acetonitrile, ethyl acetate, toluene, tetrahydrofuran, N,N-dimethylformamide, N-methylpyrrolidone, and dimethyl sulfoxide.

Examples of the condensing agent to be used in the reaction include 1-ethyl-3-(3-dimethylaminopropyl)carbodiimide hydrochloride, and 1,3-dicyclohexylcarbodiimide.

Examples of the base to be used in the reaction include 4-dimethylaminopyridine. The amount of the base to be used is within a range of 0.01 equivalents to 1.2 equivalents based on the carboxylic acid (51).

The amount of the condensing agent to be used is within a range of 1.0 equivalent to 1.2 equivalents based on the carboxylic acid (51). The amount of the compound of the formula (60) to be used is within a range of 1.0 equivalent to 1.2 equivalents based on the carboxylic acid (51). The reaction temperature is within a range of 0° C. to 60° C., and preferably 10° C. to 40° C. The reaction time is within a range of 10 minutes to 6 hours, and preferably 30 minutes to 3 hours.

[Method I]

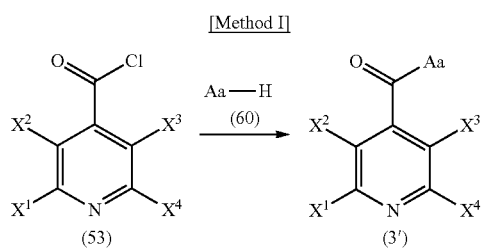

Among the compounds of formula (1), the compound of the formula (3') may also be prepared by reacting the compound of the formula (53) (in the formula (53), $X^1$, $X^2$, $X^3$ and $X^4$ are the same as defined in the formula (1)) and the compound of the formula (60) (in the formula (60), Aa is the same as defined in the formula (3)) in the presence of a base.

Examples of a solvent to be used in the reaction include tetrahydrofuran, toluene, ethyl acetate, acetonitrile, dichloromethane, chloroform, N,N-dimethylformamide, N-methylpyrrolidone, dimethyl sulfoxide and mixtures thereof.

Examples of the base to be used in the reaction include triethylamine, N,N-diisopropylethylamine, pyridine, 4-dimethylaminopyridine, sodium carbonate, and potassium carbonate. The amount of the base to be used is within a range of 1 equivalent to 10 equivalents based on the carboxylic acid chloride (53).

The amount of the compound of the formula (60) to be used is within a range of 1 equivalent to 2 equivalents based on the carboxylic acid chloride (53). The reaction temperature is within a range of −20° C. to 100° C., and preferably 10° C. to 50° C. The reaction time is within a range of 10 minutes to 6 hours, and preferably 30 minutes to 4 hours.

[Method J]

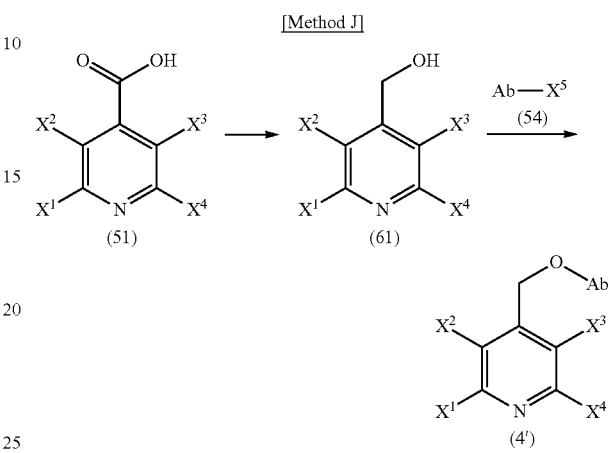

Among the compounds of formula (1), a compound of formula (4') may be prepared by the below-mentioned method from the compound of the formula (51) (in the formula (51), $X^1$, $X^2$, $X^3$ and $X^4$ are the same as defined in the formula (1)) via a compound of formula (61) (in the formula (61), $X^1$, $X^2$, $X^3$ and $X^4$ are the same as defined in the formula (1)).

In the first step, the compound of the formula (61) may be prepared by reducing the compound of the formula (51).

Examples of a solvent to be used in the reaction include tetrahydrofuran, dimethoxyethane, 1,4-dioxane, dichloromethane, chloroform, and toluene.

Examples of a reducing agent to be used in the reaction include a borane-tetrahydrofuran complex, and a borane-dimethyl sulfide complex. The amount of the reducing agent to be used is within a range of 3 equivalents to 6 equivalents based on the compound of the formula (51).

The reaction temperature is within a range of −20° C. to 80° C., and preferably 0° C. to 40° C. The reaction time is within a range of 10 minutes to 8 hours, and preferably 30 minutes to 6 hours.

Next, in the second step, the compound of the formula (61) and the compound of the formula (54) (in the formula (54), Ab is the same as defined in the formula (4), and $X^5$ is a halogen atom) are reacted in the presence of a base to obtain the compound of the formula (4').

Examples of a solvent to be used in the reaction include tetrahydrofuran, toluene, ethyl acetate, acetonitrile, dichloromethane, chloroform, N,N-dimethylformamide, N-methylpyrrolidone, dimethyl sulfoxide and mixtures thereof.

Examples of the base to be used in the reaction include triethylamine, N,N-diisopropylethylamine, pyridine, 4-dimethylaminopyridine, sodium carbonate, and potassium carbonate. The amount of the base to be used is within a range of 1 equivalent to 10 equivalents based on the compound of the formula (61).

The amount of the compound of the formula (54) to be used is within a range of 1 equivalent to 2 equivalents based on the compound of the formula (61). The reaction temperature is within a range of −20° C. to 100° C., and

[Method K]

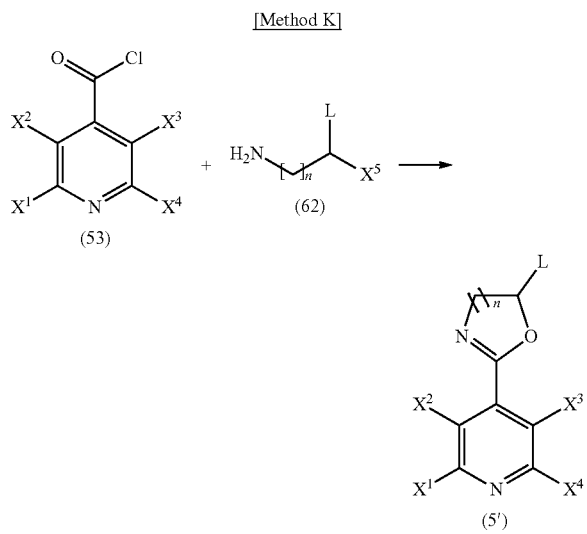

Among the compounds of formula (1), a compound of formula (5') may be prepared by reacting the compound of the formula (53) (in the formula (53), $X^1$, $X^2$, $X^3$ and $X^4$ are the same as defined in the formula (1)) and a compound of formula (62) (in the formula (62), $X^5$ is a halogen atom, and L is a hydrogen atom or a C1-4 alkyl group) in the presence of a base.

Examples of a solvent to be used in the reaction include tetrahydrofuran, toluene, ethyl acetate, acetonitrile, dichloromethane, chloroform, N,N-dimethylformamide, N-methylpyrrolidone, dimethyl sulfoxide and mixtures thereof.

Examples of the base to be used in the reaction include triethylamine, N,N-diisopropylethylamine, pyridine, 4-dimethylaminopyridine, sodium carbonate, and potassium carbonate. The amount of the base to be used is within a range of 1 equivalent to 10 equivalents based on the carboxylic acid chloride (53).

The amount of the compound of the formula (62) to be used is within a range of 1 equivalent to 2 equivalents based on the carboxylic acid chloride (53). The reaction temperature is within a range of −20° C. to 100° C., and preferably 10° C. to 90° C. The reaction time is within a range of 10 minutes to 10 hours, and preferably 30 minutes to 8 hours.

[Method L]

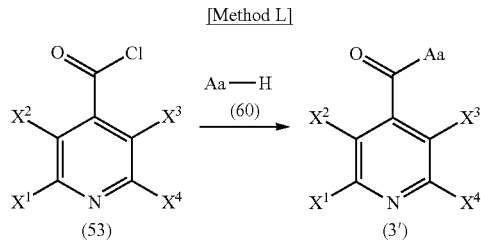

Among the compounds of formula (1), the compound of the formula (3') may also be prepared by reacting the compound of the formula (53) (in the formula (53), $X^1$, $X^2$, $X^3$ and $X^4$ are the same as defined in the formula (1)) and the compound of the formula (60) (in the formula (60), Aa is the same as defined in the formula (3)) in the presence or absence of an acid.

Although toluene, dichloromethane, chloroform, dichloroethane, N,N-dimethylformamide, N-methylpyrrolidone, dimethyl sulfoxide, nitromethane, nitrobenzene or a mixture thereof may be used as a solvent in the reaction, the reaction may be conducted in the absence of any solvents, Examples of the acid to be used in the reaction include aluminum trichloride, aluminum tribromide, lanthanoid triflate, zeolite, sulfuric acid, phosphoric acid, acetic acid, trifluoroacetic acid, hydrochloric acid, p-toluenesulfonic acid, ferric chloride, zinc dichloride, polyphosphoric acid, titanium tetrachloride, titanium tetrabromide, tin chloride, and zinc trifluoromethanesulfonate. The amount of the acid to be used is within a range of 0.01 equivalents to 10 equivalents based on the carboxylic acid chloride (53).

The amount of the compound of the formula (60) to be used is within a range of 0.5 equivalents to 2 equivalents based on the carboxylic acid chloride (53). The reaction temperature is within a range of −20° C. to 250° C., and preferably 10° C. to 100° C. The reaction time is within a range of 10 minutes to 48 hours, and preferably 30 minutes to 16 hours.

Specific Examples of a Compound of Formula (2″)

Among the compounds of formula (1), specific examples of a compound of formula (2″) are shown in the below-mentioned Tables 1 to 8.

In the specific compounds represented by the formula (2″), $X^1$, $X^2$, $X^3$ and $X^4$ represent the combination of substituents shown in the below-mentioned Table 1, and Q and A represent the combination of substituents shown in Table 2 to Table 8. J represents an oxygen atom or a sulfur atom.

In the present specification, the below-mentioned abbreviated words may be used.

n: normal sec: secondary tert: tertiary

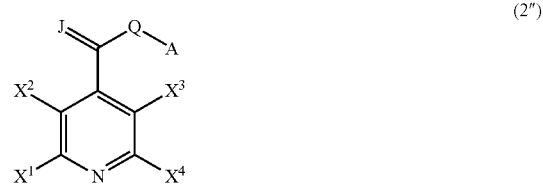

TABLE 1

| $X^1$ | $X^2$ | $X^3$ | $X^4$ | Q, A |
|---|---|---|---|---|
| F | H | H | F | Combinations shown in Tables 2 to 8. |
| F | F | H | F | Combinations shown in Tables 2 to 8. |
| F | H | H | Cl | Combinations shown in Tables 2 to 8. |
| F | F | H | Cl | Combinations shown in Tables 2 to 8. |
| F | F | F | F | Combinations shown in Tables 2 to 8. |
| F | Cl | F | F | Combinations shown in Tables 2 to 8. |

TABLE 2

| Q | A |
|---|---|
| O | H |
| O | methyl |
| O | ethyl |
| O | 2,2,2-trifluoroethyl |
| O | n-propyl |
| O | 3,3,3-trifluoropropyl |
| O | n-octyl |
| O | isobutyl |
| O | 1,1,1-trifluoropropan-2-yl |
| O | isopropyl |
| O | propargyl |
| O | 3,3-dichloroallyl |
| O | ethoxycarbonylmethyl |
| NH | tert-butyl |
| NH | 2-aminoethyl |
| NH | methyl |
| NH | cyanomethyl |
| NH | ethyl |
| NH | isopropyl |
| NH | 2-bromoethyl |
| NH | n-propyl |
| NH | allyl |
| NH | cyclohexyl |
| NH | cyclopropyl |
| NH | n-octyl |
| NH | 2-(N-tert-butoxycarbonyl)aminoethyl |
| O | allyl |
| NH | 2-methoxyethyl |
| NH | 2-hydroxyethyl |
| NH | 2-mercaptoethyl |
| NH | methoxycarbonylmethyl |
| NH | methoxy |
| O | benzyl |

TABLE 3

| Q | A |
|---|---|
| O | 2-chlorobenzyl |
| O | 3-chlorobenzyl |
| O | 4-chlorobenzyl |
| O | 4-methoxybenzyl |
| O | 4-methylbenzyl |
| O | 2-(methoxycarbonyl)benzyl |
| NH | benzyl |
| NH | benzoyl |
| O | 3,4-dichloroisothiazol-5-yl |
| O | (5-methyl-2-oxo-1,3-dioxol-4-yl)methyl |
| NH | 5,6,7,8-tetrahydronaphthalen-2-yl |
| NH | 2-benzimidazolyl |
| NH | 2,3-dihydrobenzo[b][1,4]dioxin-6-yl |
| NH | 4,5-dihydrothiazol-2-yl |
| NH | 2-methoxycarbonylthiophen-3-yl |
| NH | 2-pyrazinyl |
| NH | 2-pyridyl |
| NH | 2-pyrimidinyl |
| NH | 2-thiazolyl |
| NH | 3-cyano-4-methyl-thiophen-2-yl |
| NH | 3-cyanothiophen-2-yl |
| NH | 3-methoxycarbonylthiofen-2-yl |
| NH | dibenzo[b,d]furan-3-yl |
| NH | 3-pyridazinyl |
| NH | 3-pyridyl |
| NH | 3-triazolyl |
| NH | 4-methoxypyridin-2-yl |
| NH | 4-pyridyl |
| NH | 5-methylisoxazol-3-yl |
| NH | 5-methylthiazol-2-yl |
| O | 2-cyanophenyl |
| O | 2-methoxyphenyl |
| O | 4-chlorophenyl |

TABLE 4

| Q | A |
|---|---|
| O | 4-cyanophenyl |
| O | 4-methylphenyl |
| O | 4-nitrophenyl |
| O | cinnamyl |
| O | phenyl |
| NH | phenyl |
| NCH3 | 3-isopropyloxyphenyl |
| NCH3 | phenyl |
| NH | 2-fluorophenyl |
| NH | 3-fluorophenyl |
| NH | 4-fluorophenyl |
| NH | 2-bromophenyl |
| NH | 3-bromophenyl |
| NH | 4-bromophenyl |
| NH | 2-iodophenyl |
| NH | 3-iodophenyl |
| NH | 4-iodophenyl |
| NH | 2-ethylphenyl |
| NH | 3-ethylphenyl |
| NH | 4-ethylphenyl |
| NH | 2-n-propylphenyl |
| NH | 3-n-propylphenyl |
| NH | 4-n-propylphenyl |
| NH | 2-n-butylphenyl |
| NH | 3-n-butylphenyl |
| NH | 4-n-butylphenyl |
| NH | 2-sec-butylphenyl |
| NH | 3-sec-butylphenyl |
| NH | 4-sec-butylphenyl |
| NH | 2-isobutylphenyl |
| NH | 3-isobutylphenyl |
| NH | 4-isobutylphenyl |
| NH | 2,3,5,6-tetrofluoro-4-trifluoromethylphenyl |

TABLE 5

| Q | A |
|---|---|
| NH | 2,3-dichlorophenyl |
| NH | 2,4,6-trimethylphenyl |
| NH | 2,6-dimethylphenyl |
| NH | 2-chlorophenyl |
| NH | 2-cyano-4-nitrophenyl |
| NH | 2-methylphenyl |
| NH | 3,4,5-trichlorophenyl |
| NH | 3,4,5-trimethoxyphenyl |
| NH | 3,4-difluorophenyl |
| NH | 3,4-dimethoxyphenyl |
| NH | 3,4-dimethylphenyl |
| NH | 3,5-dichlorophenyl |
| NH | 3,5-dimethoxyphenyl |
| NH | 3,5-dimethylphenyl |
| NH | 3-benzylphenyl |
| NH | 3-bromo-4-methylphenyl |
| NH | 3-chloro-4-fluorophenyl |
| NH | 3-chloro-4-methlphenyl |
| NH | 3-chloro-4-trifluoromethylphenyl |
| NH | 3-chlorophenyl |
| NH | 3-cyanophenyl |
| NH | 3-ethoxycarbonylphenyl |
| NH | 2-ethoxyphenyl |
| NH | 3-ethoxyphenyl |
| NH | 3-fluoro-4-methylphenyl |
| NH | 3-iodo-4-methylphenyl |
| NH | 2-n-propyloxyphenyl |
| NH | 3-n-propyloxyphenyl |
| NH | 4-n-propyloxyphenyl |
| NH | 2-n-butyloxyphenyl |
| NH | 3-n-butyloxyphenyl |
| NH | 4-n-butyloxyphenyl |
| NH | 2-sec-butyloxyphenyl |

TABLE 6

| Q | A |
|---|---|
| NH | 3-sec-butyloxyphenyl |
| NH | 4-sec-butyloxyphenyl |
| NH | 2-isobutyloxyphenyl |
| NH | 3-isobutyloxyphenyl |
| NH | 4-isobutyloxyphenyl |
| NH | 2-tert-butyloxyphenyl |
| NH | 3-tert-butyloxyphenyl |
| NH | 4-tert-butyloxyphenyl |
| NH | 2-trifluoromethoxyphenyl |
| NH | 2-cyanophenyl |
| NH | 4-chloro-3-benzylaminocarbonylphenyl |
| NH | 2-trichloromethyloxyphenyl |
| NH | 3-trichloromethyloxyphenyl |
| NH | 4-trichloromethyloxyphenyl |
| NH | 2-isopropyloxyphenyl |
| NH | 3-isopropyloxyphenyl |
| NH | 3-isopropylphenyl |
| NH | 2-methoxyphenyl |
| NH | 3-methoxyphenyl |
| NH | 3-methylphenyl |
| NH | 3-phenoxyphenyl |
| NH | 3-tert-butoxyphenyl |
| NH | 3-trifluoromethoxyphenyl |
| NH | 3-trifluoromethylphenyl |
| NH | 4-chloro-3-fluorophenyl |
| NH | 4-chlorophenyl |
| NH | 4-cyanophenyl |
| NH | 4-ethoxycarbonylphenyl |
| NH | 4-ethoxyphenyl |
| NH | 4-fluoro-3-methylphenyl |
| NH | 4-isopropyloxyphenyl |
| NH | 2-isopropylphenyl |
| NH | 3-isopropylphenyl |

TABLE 7

| Q | A |
|---|---|
| NH | 4-isopropylphenyl |
| NH | 4-methoxyphenyl |
| NH | 4-methyl-3-methoxyphenyl |
| NH | 4-methyl-3-nitrophenyl |
| NH | 4-methyl-3-trifluoromethylphenyl |
| NH | 4-methylphenyl |
| NH | 4-nitrophenyl |
| NH | 4-phenoxyphenyl |
| NH | 4-tert-butoxyphenyl |
| NH | 2-tert-butylphenyl |
| NH | 3-tert-butylphenyl |
| NH | 4-tert-butylphenyl |
| NH | 4-trifluoromethoxyphenyl |
| NH | 2-hydroxy-1-phenylethyl |
| NH | 1-(2,4-dichlorophenyl)ethyl |
| NH | 1-(4-chlorophenyl)ethyl |
| NH | 1-phenylethyl |
| NH | phenylsulfonyl |
| NH | H |
| O | 4-ethylphenyl |
| O | 3-methoxyphenyl |
| O | 2-ethoxy-2-oxoethyl |
| NH | 4-trifluoromethylphenyl |
| NH | 2-phenylethyl |
| NH | 3,4-dichlorophenyl |
| NH | 4-tert-butyl-2-fluorophenyl |
| NH | propargyl |
| NH | phenylcarbonylmethyl |
| NH | 2-nitrophenyl |
| NH | (6-chloropyridin-3-yl)methyl |
| NH | 3-nitrophenyl |
| NH | 4-n-hexylphenyl |
| O | propargyl |

TABLE 8

| Q | A |
|---|---|
| NH | 3-acetylphenyl |
| NH | 3-(methylthio)phenyl |
| NH | 3-hydroxyphenyl |
| NH | benzo[d]thiazol-2-yl |
| NH | (3-(2,6-difluoropyridin-4-ylcarbonylamino)phenyl)amino |
| NH | 3-aminophenyl |
| NH | 4-chloro-3-nitrophenyl |
| O | 4-methoxyphenyl |
| O | 4-fluorophenyl |
| O | naphthalen-1-yl |
| O | cyclohexyl |
| O | 3-methylphenyl |
| O | 3-fluorophenyl |
| O | 2-methylphenyl |
| O | 2-chlorolphenyl |
| O | 2-fluorophenyl |
| O | 3-chlorophenyl |
| O | n-hexyl |
| O | n-dodecyl |
| O | phenethyl |
| O | 4-isopropylphenyl |

Among the compounds of the formula (2″), in specific examples of a compound in which A is a group of formula (2A), $X^1$, $X^2$, $X^3$ and $X^4$ represent the combination of substituents shown in the below-mentioned Table 9, Q represents a divalent group of formula: —O—$(CH_2)$n-O—, a divalent group of formula: —NH$(CH)_n$—O—, a divalent group of formula: —NH—$(CH_2)_n$—NH—, a divalent group of formula: —O—$CH_2$—CH=CH—$CH_2$—O—, a divalent group of formula: —NH—$CH_2$—CH=CH—$CH_2$—O—, a divalent group of formula: —NH—$CH_2$—CH=CH—$CH_2$—NH—, a cyclohexane-1,4-diyldioxy group, a cyclohexane-1,4-diyldiamino group, a divalent group of formula: —NH-(cyclohexane-1,4-diyl)-O—, a 1,3-phenylenediamino group, a 1,4-phenylenediamino group, a 1,4-phenylenedioxy group, a divalent group of formula: —NH-(1,4-phenylene)-O—, or a divalent group of formula (2B).

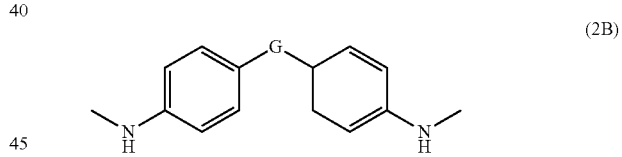

(2B)

TABLE 9

| $X^1$ | $X^2$ | $X^3$ | $X^4$ |
|---|---|---|---|
| F | F | H | F |
| F | H | H | Cl |
| F | Cl | H | F |
| F | F | H | Cl |
| F | F | F | F |
| F | Cl | F | F |

Specific Examples of a Compound of Formula (3′)

Among the compounds of formula (1), specific examples of a compound of formula (3′) are shown in the below-mentioned Table 10.

In the specific compounds represented by the formula (3′), $X^1$, $X^2$, $X^3$ and $X^4$ represent the combination of substituents shown in the below-mentioned Table 10, and Aa represents a piperidin-1-yl group, a 1-methyl-1-1H-pyrrol-2-yl group, a morpholin-4-yl group, an indolin-1-yl group, a benzoisothiazol-3(2H)-one-1,1-dioxide-2-yl group, a piperazin-1-yl group, an azetidin-1-yl group, a 2,5-dioxopyrrolidin-1-yl group, a 3-oxoisothiazol-2(3H)-yl group, a benzo[d]isothiazol-2(3H)-yl group, a 1,1-dioxo-3-oxobenzo[d]isothiazol-2(3H)-yl group, a 5,6-dihydro-4H-1,3-oxazin-2-yl group, a 1H-pyrrol-2-yl group or an isoindolin-2-yl group.

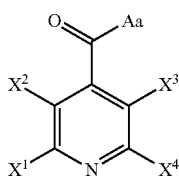

(3')

TABLE 10

| $X^1$ | $X^2$ | $X^3$ | $X^4$ |
|---|---|---|---|
| F | H | H | Cl |
| F | Cl | H | F |
| F | F | H | Cl |
| F | F | F | F |
| F | Cl | F | F |

Specific Examples of a Compound of Formula (5')

Among the compounds of formula (1), specific examples of a compound of formula (5') are shown in the below-mentioned Tables 11 and 12.

In the specific compounds represented by the formula (5'), $X^1$, $X^2$, $X^3$ and $X^4$ represent the combination of substituents shown in the below-mentioned Table 11, and the combinations of substituents as Z, substitution positions thereof, and m are shown in the below-mentioned Table 12.

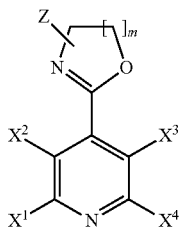

(5')

TABLE 11

| $X^1$ | $X^2$ | $X^3$ | $X^4$ | Z, m |
|---|---|---|---|---|
| F | F | H | F | Combinations shown in Table 12. |
| F | H | H | Cl | Combinations shown in Table 12. |
| F | Cl | H | F | Combinations shown in Table 12. |
| F | F | H | Cl | Combinations shown in Table 12. |
| F | F | F | F | Combinations shown in Table 12. |
| F | Cl | F | F | Combinations shown in Table 12. |

TABLE 12

| Z | m |
|---|---|
| 4-methyl | 1 |
| 5-methyl | 1 |
| 4-chloro | 1 |

TABLE 12-continued

| Z | m |
|---|---|
| 5-chloro | 1 |
| 4-fluoro | 1 |
| 5-fluoro | 1 |
| 4-methyl | 2 |
| 5-methyl | 2 |
| 4-chloro | 2 |
| 5-chloro | 2 |
| 4-fluoro | 2 |
| 5-fluoro | 2 |
| 4-methyl | 3 |
| 5-methyl | 3 |
| 6-methyl | 3 |
| 4-chloro | 3 |
| 5-chloro | 3 |
| 6-chloro | 3 |
| 4-fluoro | 3 |
| 5-fluoro | 3 |
| 6-fluoro | 3 |

[Plant pathogen]

Although the plant pathogen to be controlled by the plant disease control agent according to the present embodiment is not particularly limited, examples there ofinclude fungi, bacteria, and viruses.

Examples of the plant pathogenic fungi include *Alternaria alternata, Alternaria kikutiana, Botrytis cinerea, Cochliobolus miyabeanus, Colletotrichum atramentarium, Colletotrichum lagenarium, Fusarium oxysporum* f. sp. *cucumerium, Fusarium oxysporum* f. sp. *lycopersici, Gibberella fujikuroi, Glomerella cingulata, Pyricularia oryzae, Rhizoctonia solani, Sclerotinia minor, Verticillium albo-atrum, Puccinia recondita, Erysiphe graminis, Phytophthora infestans, Pseudoperonospora cubensis, Sphaerotheca fuliginea, Alternaria solani, Sclerotinia sclerotiorum, Venturia inaequalis, Monilinia fructicola, Colletotrichum gloeosporioides, Cercospora kikuchii, Cercospora beticola, Leptosphaeria nodorum,* and *Blumeria graminis*. Preferable examples of the plant pathogenic fungi include *Pyricularia oryzae, Blumeria graminis, Puccinia recondita,* and *Erysiphe graminis*.

Examples of the plant pathogenic bacteria include *Pseudomonas* sp., *Erwinia* sp., *Pectobacterium* sp., *Xanthomonas* sp., *Burkholderia* sp., *Streptomyces* sp., *Ralstonia* sp., *Clavibacter* sp., *Rhizomonas* sp., *Agrobacterium* sp., *Bacillus* sp., *Clostridium* sp., *Curtobacterium* sp., *Pantoea* sp., *Acidovorax* sp., *Arthrobacter* sp., and *Rhodococcus* sp. Preferable examples of the plant pathogenic bacteria include *Xanthomonas* sp., and *Xanthomonas oryzae* pv. *Orizae* is preferable among the *Xanthomonas* sp.

Examples of the plant pathogenic viruses include Soil-borne wheatmosaic virus, Soybean mosaic virus, Alfalfa mosaic virus, Potato leaf roll virus, Cucumber mosaic virus, and Tobacco mosaic virus.

The plant disease control agent according to the present embodiment contains the compound of formula (1), as an active ingredient thereof. In the present specification, the phrase "contains the compound of formula (1), as an active ingredient thereof" means that the compound of formula (1) is contained in an approximate amount such that plant disease controlling effects are exhibited, and the amount thereof is not particularly limited, provided that the compound of formula (1) is contained as an active ingredient in the form of free body, hydrate, arbitrary solvate, or salt.

In the case where the plant disease control agent according to the present embodiment is used as an active ingredient of an agricultural and horticultural disease control agent, the above-mentioned compound may be used directly, or may be used in the form of a plant disease controlling composition (preparation) having an arbitrary dosage form, such as emulsion, solution, suspension, wettable powder, powder, granule, tablet, oil solution, aerosol, or flowable agent, prepared by conventionally mixing the compound with an agriculturally and horticulturally acceptable carrier, such as a solid carrier, a liquid carrier, a gaseous carrier, a surfactant, or a dispersing agent. The plant disease controlling composition may further contain additional formulation auxiliaries.

Examples of the available carrier include liquid carriers, solid carriers, gaseous carriers, surfactants, and dispersing agents. Examples of the formulation auxiliaries include ones conventionally formulated in plant disease controlling compositions.

Examples of the solid carriers include: fine powders or granules of clays (such as kaolin clay, diatomaceous earth, bentonite, and acid clay), synthetic hydrated silicon oxide, talc, ceramic, or additional inorganic minerals (such as selenite, quartz, sulfur, active carbon, calcium carbonate, and hydrated silica); starch; lactose; and synthesized polymers such as vinyl chloride polymers, and polyurethane.

Examples of the liquid carriers include: alcohols (such as methanol, ethanol, isopropanol, polyethylene glycol, propylene glycol, dipropylene glycol, tripropylene glycol, and glycerin); ketones (such as acetone and methyl ethyl ketone); aromatic hydrocarbons (such as benzyl alcohol, benzene, toluene, xylene, ethylbenzene, and methylnaphthalen); aliphatic hydrocarbons (such as paraffin, n-hexane, cyclohexane, kerosene, and lamp oil); ethers (such as diethylene glycol monoethyl ether, diethylene glycol monomethyl ether, diisopropyl ether, diethyl ether, dioxane, and tetrahydrofuran); esters (such as propylene carbonate, ethyl acetate, butyl acetate, benzyl benzoate, isopropyl myristate, and fatty acid esters of propylene glycol); nitriles (such as acetonitrile and isobutyronitrile); amides (such as dimethylformamide, dimethylacetamide, and N-methylpyrrolidone); halogenated hydrocarbons (such as dichloromethane, trichloroethane, and carbon tetrachloride); animal or vegetable oils such as soybean oil, and cottonseed oil; dimethyl sulfoxide, silicone oil, higher fatty acid, glycerol formal, and water.

Examples of the gaseous carriers include LPG, air, nitrogen, carbon dioxide, and dimethyl ether.

Examples of the surfactant or the dispersing agent, which is used to conduct emulsification, dispersion, or spreading, include alkylsulfuates, alkyl (aryl) sulfonic acid salts, polyoxyalkylene alkyl (aryl) ethers, polyhydric alcohol esters, and lignin sulfonate. Examples of the auxiliaries used to improve the properties of preparations include carboxymethyl cellulose, gum arabic, polyethylene glycol, and calcium stearate.

The above-mentioned carriers, surfactants, dispersing agents, and auxiliaries may each be used alone, or in combination thereof, as needed.

The amount of the plant disease control agent (the compound of formula (1)) in the plant disease controlling composition is not particularly limited, and the amount is usually, for example, 1% by mass to 50% by mass in the case of an emulsion, 1% by mass to 50% by mass in the case of a wettable powder, 0.1% by mass to 30% by mass in the case of a powder formulation, 0.1% by mass to 15% by mass in the case of a granule, 0.1% by mass to 10% by mass in the case of an oil solution, and 0.1% by mass to 10% by mass in the case of an aerosol.

The plant disease control agent or the plant disease controlling composition according to the present embodiment may be used directly, or may be diluted to be used, as needed.

The plant disease control agent or the plant disease controlling composition may be used with other pest control agents, and, for example, may be mixed with a resistance inducer or other pest control agents to be sprayed, or may be sprayed therewith separately at different times or simultaneously.

Examples of other pest control agents include pesticides, fungicides, miticides, herbicides, plant growth regulators, and fertilizers, and specific examples thereof include ones described in Pesticide Manual (The Pesticide Manual, the $13^{th}$ edition, issued by The British Crop Protection Council) or SHIBUYA INDEX (SHIBUYA INDEX, the $13^{th}$ edition, 2008, issued by SHIBUYA INDEX RESEARCH GROUP).

Examples of the pesticide include acephate, dichlorvos, EPN, fenitrothion, fenamifos, prothiofos, profenofos, pyraclofos, chlorpyrifos-methyl, chlorfenvinphos, demeton, ethion, malathion, coumaphos, isoxathion, fenthion, diazinon, thiodicarb, aldicarb, oxamyl, propoxur, carbaryl, fenobucarb, ethiofencarb, fenothiocarb, pirimicarb, carbofuran, carbosulfan, furathiocarb, hyquincarb, alanycarb, methomyl, benfurcarb, cartap, thiocyclam, bensultap, dicofol, tetradifon, acrinathrin, bifenthrin, cycloprothrin, cyfluthrin, dimefluthrin, empenthrin, fenfluthrin, fenpropathrin, imiprothrin, metofluthrin, permethrin, phenothrin, resmethrin, tefluthrin, tetramethrin, tralomethrin, transfluthrin, cypermethrin, deltamethrin, cyhalothrin, fenvalerate, fluvalinate, ethofenprox, flufenprox, halfenprox, silafluofen, cyromazine, diflubenzuron, teflubenzuron, flucycloxuron, flufenoxuron, hexaflumuron, lufenuron, novaluron, penfluron, triflumuron, chlorfluazuron, diafenthiuron, methoprene, fenoxycarb, pyriproxyfen, halofenozide, tebufenozide, methoxyfenozide, chromafenozide, dicyclanil, buprofezin, hexythiazox, amitraz, chlordimeform, pyridaben, fenpyroximate, flufenerim, pyrimidifen, tebufenpyrad, tolfenpyrad, fluacrypyrim, acequinocyl, cyflumetofen, flubendiamide, ethiprole, fipronil, ethoxazole, imidacloprid, nitempyram, clothinidin, acetamiprid, dinotefuran, thiacloprid, thiamethoxam, pymetrozine, bifenazate, spirodiclofen, spiromesifen, flonicamid, chlorfenapyr, pyriproxyfene, indoxacarb, pyridalyl, spinosad, avermectin, milbemycin, azadirachtin, nicotine, rotenone, BT agents, insect pathogenic viral agents, emamectin benzoate, spinetoram, pyrifluquinazon, chlorantraniliprole, cyantraniliprole, cyenopyrafen, spirotetramat, lepimectin, metaflumizone, pyrafluprole, pyriprole, dimefluthrin, fenazaflor, hydramethylnon, triazamate, afidopyropen, and flupyrimin.

Examples of the fungicide include: strobilurin-based compounds, such as azoxystrobin, kresoxym-methyl, trifloxystrobin, orysastrobin, picoxystrobin, and fluoxastrobin; anilino pyrimidine-based compounds such as mepanipyrim, pyrimethanil, and cyprodinil; azole-based compounds such as triadimefon, bitertanol, triflumizole, etaconazole, propiconazole, penconazole, flusilazole, myclobutanil, cyproconazole, tebuconazole, hexaconazole, prochloraz, and simeconazole; quinoxaline-based compounds such as quinomethionate; dithiocarbamate-bsed compounds such as maneb, zineb, mancozeb, polycarbamate, and propineb; phenylcarbamate-based compounds such as diethofencarb; organic chlorine-based compounds such as chlorothalonil and quintozene; benzimidazole-based compounds such as benomyl, thiophanate-methyl, and carbendazim; phenylamide-based compounds such as metalaxyl, oxadixyl, ofurase, benalaxyl, furalaxyl, and cyprofuram; sulfenic acid-based compounds such as dichlofluanid; copper-based compounds such as copper hydroxide and oxine-copper; isoxazole-based compounds such as hydroxyisoxazole; organic phosphorus-based compounds such as fosetyl-aluminium and tolclofos-methyl; N-halogenothioalkyl-based compounds such as captan, captafol, and folpet; dicarboximide-based compounds such as procymidone, iprodione, and vinchlozolin; benzanilide-based compounds such as flutolanil and mepronil; morpholine-based compounds such as fenpropimorph and dimethomorph; organic tin-based compounds such as fentin hydroxide and fentin acetate; cyanopyrrole-based compounds such as fludioxonil and fenpiclonil; others such as fthalide, probenazole, acibenzolar-S-methyl, tiadinil, isotianil, carpropamid, diclocymet, fenoxanil, tricyclazole, pyroquilon, ferimzone, fluazinam, cymoxanil, triforine, pyrifenox, fenarimol, fenpropidin, pencycuron, cyazofamid, cyflufenamid, boscalid, penthiopyrad, proquinazid, quinoxyfen, famoxadone, fenamidone, iprovalicarb, benthiavalicarb-isopropyl, fluopicolide, pyribencarb, flutianil, isopyrazam, fenpicoxamid, kasugamycin, and validamycin.

Examples of the miticide include bromopropylate, tetradifon, propargite, amitraz, fenothiocarb, hexythiazox, fenbutatin oxide, dienochlor, fenpyroximate, tebufenpyrad, pyridaben, pyrimidifen, clofentezine, etoxazole, halfenprox, milbemectin, acequinocyl, bifenazate, fluacryprim, spirodiclofen, spiromesifen, chlorfenapyr, avermectin, cyenopyrafen, and cyflumetofen.

Examples of the herbicide include: phenoxy acid-based compounds such as cyhalofop-butyl, and 2,4-D; carbamate-based compounds such as esprocarb and desmedipham; acid amide-based compounds such as alachlor and metolachlor; urea-based compounds such as diuron and tebuthiuron; sulfonylurea-based compounds such as halosulfuron-methyl and flazasulfuron; pyrimidyloxy benzoic acid-based compounds such as pyriminobac-methyl; and amino acid-based compounds such as glyphosate, bialafos, and glufosinate (glufosinate-ammonium).

Examples of the plant growth regulator include: ethylene preparations such as ethephon; auxins such as indolebutyric acid and ethychlozate; cytokinins; gibberellins; auxin antagonists; plant growth suppressors; and transpiration suppressors.

Examples of the fertilizer include: nitrogen fertilizers such as urea, ammonium nitrate, magnesium ammonium nitrate, and ammonium chloride; phosphoric acid fertilizers such as calcium superphosphate, ammonium phosphate, magnesium superphosphate, and magnesium phosphate; potassium fertilizers such as potassium chloride, potassium bicarbonate, magnesium-potassium nitrate, potassium nitrate, and potassium sodium nitrate; manganese fertilizers such as manganese sulfate and magnesium manganese nitrate; and boron fertilizers such as boric acid and salts of boric acid.

In an embodiment, the present invention provides a method for controlling plant disease in which the plant disease control agent or the compound is brought into contact with a plant body or a seed, or is contained in a cultivation bed. The plant disease control agent or the compound may be used in the form of a plant disease controlling composition.

In the case where the plant disease control agent or the compound are brought into contact with plant bodies, the plant disease control agent or the compound may be brought into contact with leaves, stems, roots, rootstocks, tuberosities, or bulbs, of plants, germinated buds, or the like. Alternatively, the plant disease control agent or the compound may be brought into contact with plant seeds. Examples of the cultivation bed include soils, water surfaces of rice fields where rice is grown, carriers on which plants are grown, and water of hydroponic culture. The water of hydroponic culture may contain nutrients.

The method for bringing the above-mentioned plant disease control agent or the above-mentioned compound into contact with plant bodies or seeds, or the method for making the above-mentioned plant disease control agent or the above-mentioned compound to be contained in cultivation beds is not particularly limited, provided that the method is usually used in agriculture and horticulture, and examples thereof include foliar application, submerged application, soil treatment, nursery box application, seed treatment, immersion treatment, fertilizer mix, and irrigation water mixing.

The application amount of the plant disease control agent according to the present embodiment may be determined depending on the type of target disease, the infection degree, the kind of target crop, and the target site, while taking into account the application mode, such as aerial application or ultramicro inspersion, in addition to the application method.

For example, in the case of spraying the plant disease control agent to leaves and stems of plants, 1 to 1000 g of the plant disease control agent may be diluted with 50 to 1000 L of water per 10 ares to be used in the form of emulsion, wettable powder or flowable formulation, or 1 to 10 kg of the plant disease control agent may be used per 10 ares in the powder form.

In the case where the plant disease control agent is applied in the soil, approximately 1 to 10 kg of the plant disease control agent may be used per 10 ares in the granule form, for example.

EXAMPLES

Hereinafter, the present invention will be explained further specifically by illustrating examples; however, the scope of the present invention is not limited to these examples.

Hereinafter, the below-mentioned abbreviated words may be used in the examples.

ESI: Electrospray ionization
MS: Mass spectrum
IR: Infrared absorption spectrum
n: normal
tert: tertiary Example 1

2,3,6-trifluoroisonicotinic acid (1.76 g) was dissolved in N,N-dimethylformamide (10 mL), followed by adding bromoethane (1.08 g) and potassium carbonate (1.38 g) to the solution, and then conducting stirring at 80° C. for 2 hours. Then, the reaction mixture was cooled to room temperature, ethyl acetate was added thereto, the mixture was subjected to extraction with water, an organic layer was dried with anhydrous magnesium sulfate, and then the solvent was distilled off. The residue was purified by silica gel chromatography to obtain a compound of Example 1-117 (yield 1.44 g).

Example 2

2,3,6-trifluoroisonicotinic acid (5.28 g) was dissolved in thionyl chloride (30 mL), followed by heating the mixture to reflux for 1 hour. The resultant was concentrated, the concentrate was dissolved in acetonitrile (30 mL), and then 3-chloro-4-methylaniline (5.64 g) and pyridine (3.20 g) was added to the solution, followed by heating the mixture to reflux for 1 hour. Then, the reaction mixture was cooled to room temperature, ethyl acetate was added thereto, the mixture was washed sequentially with 1N hydrochloric acid and 1N sodium hydroxide, an organic layer was dried with anhydrous magnesium sulfate, and then the solvent was distilled off. The residue was purified by silica gel chromatography to obtain a compound of Example 1-30 (yield 7.70 g).

Example 3

2,3,6-trifluoro-4-pyridinemethanol (106 mg) was dissolved in dichloromethane (8 mL), acetyl chloride (65 mg) was added to the solution, the mixture was cooled to 0° C., N,N-diisopropylethylamine (130 mg) was added thereto, and then the mixture was stirred at room temperature overnight. Then, the solvent was distilled off, the resultant was dissolved in diethyl ether, the solution was washed sequentially with saturated sodium carbonate, 2% hydrochloric acid, and saturated brine, and the resultant organic layer was dried with anhydrous magnesium sulfate. The solvent was distilled off using an evaporator, and then the residue was purified by silica gel chromatography to obtain a compound of Example 3-1 (yield 63.2 mg).

Example 4

2,6-difluoroisonicotinic acid (50 mg) was dissolved in chloroform (3.1 mL), and then aniline (29 μL), 1-ethyl-3-(3-dimethylaminopropyl)carbodiimide hydrochloride (65 mg), and 4-dimethylaminopyridine (catalytic amount) were added to the solution, followed by stirring the mixture at room temperature for 3 hours. Then, water was added to the reaction mixture, and then the mixture was subjected to extraction with ethyl acetate, followed by conducting washing sequentially with saturated ammonium chloride and saturated sodium hydrogen carbonate. The resultant organic layer was dried with anhydrous sodium sulfate, and then the solvent was distilled off. The residue was purified by silica gel chromatography to obtain a compound of Example 1-143 (yield 66.3 mg).

Example 5

2,3,6-trifluoroisonicotinic acid (30 mg) was dissolved in chloroform (3.1 mL), and then ethylene diamine (6.0 μL), 1-ethyl-3-(3-dimethylaminopropyl)carbodiimide hydrochloride (38 mg), 1-hydroxybenzotriazole (27 mg), and triethylamine (30 μL) were added to the solution, followed by stirring the mixture at room temperature overnight. 1-ethyl-3-(3-dimethylaminopropyl)carbodiimide hydrochloride (38 mg) and 1-hydroxybenzotriazole (27 mg) were added to the resultant again, and then the mixture was stirred at room temperature for 3 hours. Then, water was added to the reaction mixture, and then the resultant was subjected to extraction with ethyl acetate, followed by conducting washing sequentially with saturated ammonium chloride and saturated sodium hydrogen carbonate. The resultant organic layer was dried with anhydrous sodium sulfate, and then the solvent was distilled off. The residue was purified by silica gel chromatography to obtain a compound of Example 1-150 (yield 20.1 mg).

Example 6

2,3,6-trifluoroisonicotinic acid (100 mg) was dissolved in N,N-dimethylformamide (5.6 mL), and then 2-chloroethylamine hydrochloride (79 mg), 1-ethyl-3-(3-dimethylaminopropyl)carbodiimide hydrochloride (128 mg), 1-hydroxybenzotriazole (92 mg), and triethylamine (101 L) were added to the solution, followed by stirring the mixture at room temperature for 3 hours. Then, water was added to the reaction mixture, and the resultant was subjected to extraction with ethyl acetate, followed by conducting washing sequentially with saturated ammonium chloride and saturated sodium hydrogen carbonate. The resultant organic layer was dried with anhydrous sodium sulfate, the solvent was distilled off, and then the residue was purified by silica gel chromatography to obtain N-(2-chloroethyl)-2,3,6-trifluoroisonicotinamide (yield 100 mg).

The obtained N-(2-chloroethyl)-2,3,6-trifluoroisonicotinamide (20 mg) was dissolved in tetrahydrofuran (8.4 mL), and then 55% sodium hydride (3.8 mg) was added to the solution under ice-cooling, followed by stirring the mixture for 3 hours. Then, water was added to the reaction mixture, subjected to extraction with ethyl acetate, the resultant organic layer was dried with anhydrous sodium sulfate, and then the solvent was distilled off. The residue was purified by silica gel chromatography to obtain a compound of Example 4-2 (yield 16 mg).

Example 7

2,6-difluoroisonicotinic acid (80 mg) was dissolved in acetonitrile (1 mL), and then cyclohexyl alcohol (50 mg), 1-ethyl-3-(3-dimethylaminopropyl)carbodiimide hydrochloride (96 mg), and 4-dimethylaminopyridine (61 mg) were added to the solution, followed by stirring the mixture at room temperature for 24 hours. Then, water was added to the reaction mixture, and then the resultant was subjected to extraction with ethyl acetate, followed by conducting washing sequentially with saturated sodium hydrogen carbonate aqueous solution and saturated sodium chloride aqueous solution. The resultant organic layer was dried with anhydrous sodium sulfate, and then the solvent was distilled off. The residue was purified by preparative TLC to obtain a compound of Example 1-205 (yield 42 mg).

Example 8

2,3,6-trifluoroisonicotinic acid (177 mg, 1.0 mmol) was dissolved in dichloroethane, and then thionyl chloride (1 mL) was added to the solution, followed by heating the mixture to reflux for 2 hours while conducting stirring. The solvent was distilled off using an evaporator, and then nitromethane (3 mL), 1-methylpyrrole (54 mg, 0.67 mmol), and zinc trifluoromethanesulfonate (II) (24 mg, 0.066 mmol) were added to the resultant, followed by stirring the mixture at room temperature overnight. Sodium hydrogen carbonate was added to the reaction mixture, and then water was added to the mixture to conduct extraction with chloroform. The resultant organic layer was dried with anhydrous sodium sulfate, and the solvent was distilled off using an evaporator, followed by purifying the residue by silica gel chromatography (mobile phase:hexane/ethyl acetate=1/1 (volume ratio)), and then conducting washing with hexane to obtain compound 2-2 (yield 44 mg, 0.18 mmol, 27% yield).

In accordance with the method of Examples 1 to 8, compounds of Examples 1-1 to 1-218, represented by formula (2") and shown in the below-mentioned Tables 13 to 34, were prepared. In addition, compounds of Examples 2-1 to 2-5, represented by formula (3') and shown in the below-mentioned Table 35, were prepared. In addition, compounds of Examples 3-1 and 3-2, represented by formula (4') and shown in the below-mentioned Table 36, were prepared. In addition, compounds of Examples 4-1 to 4-4, represented by formula (5') and shown in the below-mentioned Table 37, were prepared.

Data of MS, IR, and H-NMR of each compounds of formula (2"), (3'), (4') or (5'), as well as those of the compounds obtained in Examples 1 to 8, are shown in Tables 13 to 37. Deuterated acetone was used as a solvent to conduct H-NMR measurement (400 MHz, 500 MHz or 600 MHz) of compounds of Examples 1-8, 1-69, 1-175, 1-176 and 4-2, a mixture of deuterated chloroform and deuterated methanol at a ratio of 1:1 was used as a solvent to conduct $^1$H-NMR measurement of a compound of Example 1-93, and deuterated chloroform was used as a solvent to conduct $^1$H-NMR measurement of compounds of other examples. MS was measured by ESI-MS method. IR was measured by the KBr method.

The compounds of Examples 1-1 to 1-218, represented by the formula (2"), are shown in Tables 13 to 34.

(2")

TABLE 13

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-1 | | 1.27 (d, 6H), 3.47 (s, 3H), 4.41-4.47 (m, 1H), 6.63-6.65 (m, 2H), 6.68-6.69 (m, 1H), 6.76-6.79 (m, 1H), 7.13-7.15 (m, 1H) | m/z = 325 (M + H) |
| 1-2 | | 3.50 (3H, s), 6.70 (1H, m), 7.11 (2H, m), 7.30 (3H, m) | IR 1653, 1471, 1440, 1395, 1025, 701 |
| 1-3 | | 1.80 (4H, m), 2.76 (4H, m), 7.07 (1H, d), 7.28 (1H, d), 7.33 (1H, m), 7.45 (1H, m), 8.17 (1H, br) | |
| 1-4 | | 1.60 (1H, br), 7.79 (1H, s) | m/z = 393 (M + H) |
| 1-5 | | 7.36 (2H, m), 7.56 (1H, m), 8.49 (1H, dd) | m/z = 321 (M + H) |

TABLE 13-continued

| Example | Formula | ¹H-NMR (measured at 400 MHz, 500 MHz, or 600 MHz) δ ppm | ESI MS (m/z) or IR (KBr) cm$^{-1}$ |
|---|---|---|---|
| 1-6 | | 2.24 (6H, s), 2.31 (3H, s), 6.97 (2H, s), 7.49 (1H, m), 7.72 (1H, br) | IR 1655, 1541, 1471, 1432, 1377, 1032 |
| 1-7 | | 2.28 (6H, s), 7.17 (3H, m), 7.46 (1H, m), 7.80 (1H, br) | IR 1659, 1541, 1473, 1380, 1033 |
| 1-8 | | 7.20 (2H, m), 7.32 (1H, m), 7.47 (2H, m) | m/z = 293 (M + H) |
| 1-9 | | 4.29 (4H, m), 6.88 (1H, d), 7.01 (1H, dd), 7.28 (1H, d), 7.51 (1H, m), 8.10 (1H, br) | m/z = 311 (M + H) |
| 1-10 | | 7.17 (1H, dt), 7.37 (1H, t), 7.47 (1H, dd), 7.55 (1H, m), 8.51 (1H, d), 8.99 (1H, br) | m/z = 224 (M + H) |

TABLE 14

| Example | Formula | ¹H-NMR (measured at 400 MHz, 500 MHz, or 600 MHz) δ ppm | ESI MS (m/z) or IR (KBr) cm$^{-1}$ |
|---|---|---|---|
| 1-11 | | 7.55 (1H, m), 8.55 (2H, m), 8.89 (1H, d), 9.19 (1H, br) | m/z = 323 (M + H) |

TABLE 14-continued

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-12 | | 3.94 (2H, t), 3.40 (2H, t), 7.32 (1H, m) | m/z = 262 (M + H) |
| 1-13 | | 3.95 (3H, s), 7.49 (1H, m), 7.57 (1H, d), 8.23 (1H, d), 11.37 (1H, br) | m/z = 317 (M + H) |
| 1-14 | | 2.36 (3H, s), 7.19 (1H, t), 7.30 (2H, m), 7.56 (1H, m), 8.01 (1H, d) | IR 1655, 1546, 1459, 1370, 1033 |
| 1-15 | | 7.53 (1H, m), 8.36 (1H, t), 8.49 (1H, d), 8.02 (1H, br), 9.65 (1H, d) | m/z = 255 (M + H) |
| 1-16 | | 7.17 (1H, dd), 7.49 (1H, m), 7.81 (1H, dt), 8.30 (1H, d), 8.37 (1H, d) | m/z = 254 (M + H) |
| 1-17 | | 7.15 (1H, t), 7.42 (1H, m), 8.68 (1H, d), 8.85 (1H, br) | m/z = 255 (M + H) |
| 1-18 | | 7.14 (1H, d), 7.50 (1H, d), 7.53 (1H, m) | m/z = 260 (M + H) |

TABLE 14-continued

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-19 | (2,6-difluoro-3-fluoropyridine-4-carboxamide with 3,4,5-trichlorophenyl) | 7.50 (1H, m), 7.78 (2H, s), 8.21 (1H, br) | m/z = 355 (M + H) |
| 1-20 | (2,3,6-trifluoropyridine-4-carboxamide with 3,4,5-trimethoxyphenyl) | 3.85 (s, 3H), 3.90 (s, 6H), 6.93 (s, 2H), 7.49-7.50 (m, 1H), 8.19-8.22 (m, 1H) | m/z = 343 (M + H) |

TABLE 15

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-21 | (2,3,6-trifluoropyridine-4-carboxamide with 3,4-difluorophenyl) | 7.21 (2H, m), 7.50 (1H, m), 7.74 (1H, m) | m/z = 289 (M + H) |
| 1-22 | (2,3,6-trifluoropyridine-4-carboxamide with 3,4-dimethoxyphenyl) | 3.91 (3H, s), 3.93 (3H, s), 6.88 (1H, d), 7.05 (1H, dd), 7.39 (1H, d), 7.51 (1H, m), 8.19 (1H, br) | m/z = 313 (M + H) |
| 1-23 | (2,3,6-trifluoropyridine-4-carboxamide with 3,4-dimethylphenyl) | 2.27 (3H, s), 2.29 (3H, s), 7.16 (1H, d), 7.36 (1H, dd), 7.40 (1H, d), 7.51 (1H, m), 8.13 (1H, br) | m/z = 281 (M + H) |

TABLE 15-continued

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-24 | 2,3,6-trifluoro-N-(3,5-dichlorophenyl)pyridine-4-carboxamide | 7.23 (1H, s), 7.49 (1H, m), 7.60 (1H, s), 8.20 (1H, br) | m/z = 321 (M + H) |
| 1-25 | 2,3,6-trifluoro-N-(3,5-dimethoxyphenyl)pyridine-4-carboxamide | 3.82 (6H, s), 6.35 (1H, t), 6.85 (2H, d), 7.49 (1H, m), 8.16 (1H, br) | m/z = 313 (M + H) |
| 1-26 | 2,3,6-trifluoro-N-(3,5-dimethylphenyl)pyridine-4-carboxamide | 2.35 (6H, s), 6.89 (1H, s), 7.26 (2H, s), 7.51 (1H, m), 8.13 (1H, br) | m/z = 281 (M + H) |
| 1-27 | 2,3,6-trifluoro-N-(3-benzylphenyl)pyridine-4-carboxamide | 4.01 (2H, s), 7.08 (1H, d), 7.20 (2H, d), 7.24-7.35 (4H, m), 7.43 (1H, s), 7.51 (2H, m) | m/z = 343 (M + H) |
| 1-28 | 2,3,6-trifluoro-N-(3-bromo-4-methylphenyl)pyridine-4-carboxamide | 2.41 (3H, s), 7.26 (1H, m), 7.46 (1H, dd), 7.51 (1H, m), 7.91 (1H, d), 8.17 (1H, br) | m/z = 345 (M + H) |
| 1-29 | 2,3,6-trifluoro-N-(3-chloro-4-fluorophenyl)pyridine-4-carboxamide | 7.19 (1H, t), 7.45 (1H, m), 7.51 (1H, m), 7.85 (1H, dd), 8.21 (1H, br) | m/z = 305 (M + H) |

TABLE 15-continued

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-30 | (2,6-difluoro-3-fluoropyridine-4-carboxamide with N-(3-chloro-4-methylphenyl)) | 2.40 (3H, s), 7.27 (1H, d), 7.40 (1H, dd), 7.53 (1H, m), 7.77 (1H, d) | m/z = 301 (M + H) |

TABLE 16

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-31 | (2,6-difluoro-3-fluoropyridine-4-carboxamide with N-(3-chloro-4-trifluoromethylphenyl)) | 7.51 (1H, m), 7.61 (1H, d), 7.73 (1H, d), 7.95 (1H, s), 8.34 (1H, br) | m/z = 355 (M + H) |
| 1-32 | (2,6-difluoro-3-fluoropyridine-4-carboxamide with N-(3-chlorophenyl)) | 7.24 (1H, dt), 7.34 (1H, t), 7.46 (1H, dd), 7.51 (1H, m), 7.78 (1H, dd), 8.21 (1H, br) | m/z = 287 (M + H) |
| 1-33 | (2,6-difluoro-3-fluoropyridine-4-carboxamide with N-(3-cyano-4-methylthiophen-2-yl)) | 2.36 (3H, s), 6.67 (1H, s), 7.54 (1H, m), 9.46 (1H, br) | m/z = 284 (M + H) |
| 1-34 | (2,6-difluoro-3-fluoropyridine-4-carboxamide with N-(3-cyanophenyl)) | 7.53 (3H, m), 7.79 (1H, m), 8.10 (1H, s), 8.29 (1H, br) | m/z = 278 (M + H) |
| 1-35 | (2,6-difluoro-3-fluoropyridine-4-carboxamide with N-(2-cyanophenyl)) | 7.33 (1H, t), 7.47 (1H, m), 7.71 (2H, m), 8.51 (1H, d), 8.86 (1H, br) | m/z = 278 (M + H) |

TABLE 16-continued
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-36 | 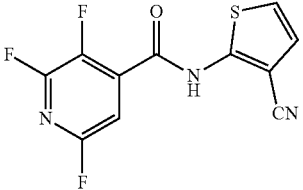 [SMILES: N#Cc1ccsc1NC(=O)c1cc(F)nc(F)c1F] | 7.06 (1H, d), 7.10 (1H, d), 7.54 (1H, m), 9.54 (1H, br) | m/z = 283 (M + H) |
| 1-37 | 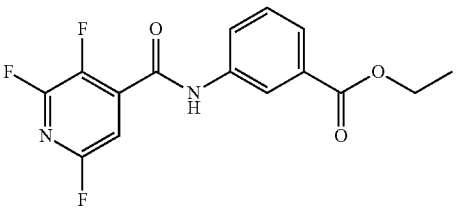 [SMILES: CCOC(=O)c1cccc(NC(=O)c2cc(F)nc(F)c2F)c1] | 1.42 (3H, t), 4.41 (2H, q), 7.51 (2H, m), 7.92 (1H, d), 8.01 (1H, d), 8.14 (1H, s), 8.31 (1H, br) | m/z = 325 (M + H) |
| 1-38 | 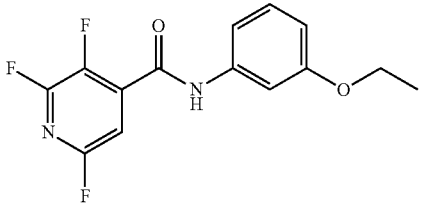 [SMILES: CCOc1cccc(NC(=O)c2cc(F)nc(F)c2F)c1] | 1.44 (3H, t), 4.07 (2H, q), 6.77 (1H, dd), 7.10 (1H, dd), 7.30 (1H, t), 7.36 (1H, t), 7.51 (1H, m), 8.20 (1H, br) | m/z = 297 (M + H) |
| 1-39 | 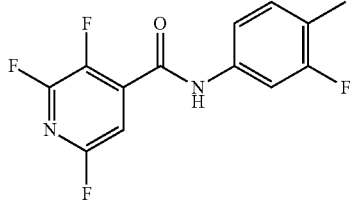 [SMILES: Cc1ccc(NC(=O)c2cc(F)nc(F)c2F)cc1F] | 2.28 (3H, s), 7.17 (1H, dd), 7.20 (1H, t), 7.51 (1H, m), 7.55 (1H, dd), 8.20 (1H, br) | m/z = 285 (M + H) |
| 1-40 | 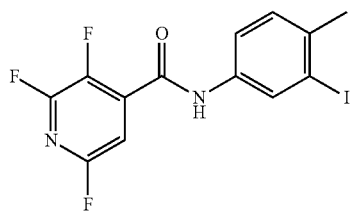 [SMILES: Cc1ccc(NC(=O)c2cc(F)nc(F)c2F)cc1I] | 2.44 (3H, s), 7.26 (1H, m), 7.50 (1H, m), 7.53 (1H, dd), 8.11 (1H, d), 8.14 (1H, br) | m/z = 393 (M + H) |
TABLE 17
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-41 | 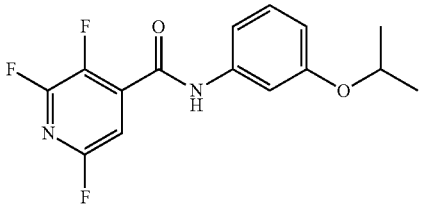 [SMILES: CC(C)Oc1cccc(NC(=O)c2cc(F)nc(F)c2F)c1] | 1.37 (6H, d), 4.59 (1H, sep), 6.76 (1H, dd), 7.08 (1H, dd), 7.28 (1H, t), 7.34 (1H, dd), 7.50 (1H, m), 8.19 (1H, br) | m/z = 311 (M + H) |

TABLE 17-continued
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-42 | 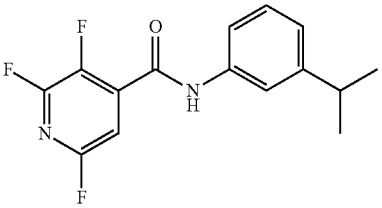 | 1.28 (6H, d), 2.95 (1H, sep), 7.12 (1H, d), 7.34 (1H, t), 7.48 (2H, m), 7.51 (1H, m) | m/z = 295 (M + H) |
| 1-43 | 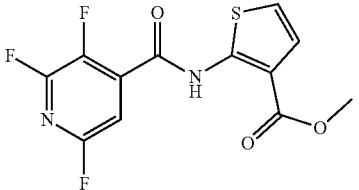 [SMILES: COC(=O)c1ccsc1NC(=O)c1cc(F)nc(F)c1F] | 3.96 (3H, s), 6.92 (1H, d), 7.32 (1H, d), 7.56 (1H, m) | m/z = 317 (M + H) |
| 1-44 | 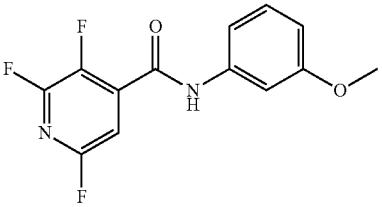 | 3.85 (3H, s), 6.79 (1H, m), 7.11 (1H, d), 7.29 (1H, t), 7.38 (1H, m), 7.51 (1H, m) | m/z = 283 (M + H) |
| 1-45 | 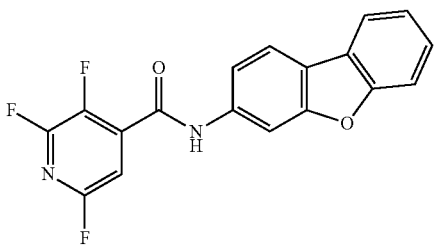 [SMILES: O=C(Nc1ccc2c(c1)oc1ccccc12)c1cc(F)nc(F)c1F] | 7.35 (1H, t), 7.39 (1H, dd), 7.46 (1H, t), 7.54 (1H, m), 7.58 (1H, d), 7.93 (2H, m), 8.20 (1H, d), 8.50 (1H, br) | m/z = 313 (M + H) |
| 1-46 | 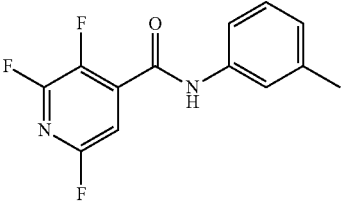 [SMILES: Cc1cccc(NC(=O)c2cc(F)nc(F)c2F)c1] | 2.40 (3H, s), 7.06 (1H, d), 7.30 (1H, t), 7.42 (1H, d), 7.47 (1H, m), 7.51 (1H, s) | m/z = 267 (M + H) |
| 1-47 | 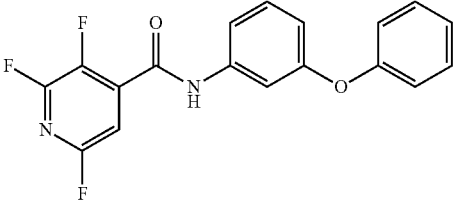 [SMILES: O=C(Nc1cccc(Oc2ccccc2)c1)c1cc(F)nc(F)c1F] | 6.88 (1H, m), 7.05 (2H, m), 7.15 (1H, m), 7.36 (5H, m), 7.49 (1H, m), 8.20 (1H, br) | m/z = 345 (M + H) |
| 1-48 | 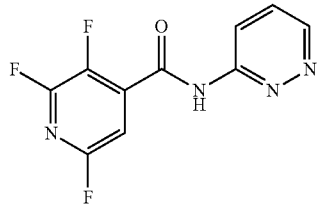 [SMILES: O=C(Nc1cccnn1)c1cc(F)nc(F)c1F] | 7.47 (1H, m), 7.61 (1H, dd), 8.58 (1H, d), 9.04 (1H, d) | m/z = 255 (M + H) |

TABLE 17-continued

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-49 | (structure) | 7.43 (1H, dd), 7.52 (1H, m), 8.28 (1H, dd), 8.35 (1H, br), 8.50 (1H, m), 8.78 (1H, m) | m/z = 254 (M + H) |
| 1-50 | (structure) | 1.39 (9H, s), 6.89 (1H, m), 7.30 (2H, m), 7.39 (1H, m), 7.52 (1H, m) | m/z = 325 (M + H) |

TABLE 18

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-51 | (structure) | 7.25-7.27 (m, 1H), 7.49 (m, 1H), 7.84 (m, 1H) | m/z = 244 (M + H) |
| 1-52 | (structure) | 7.11 (1H, d), 7.41-7.51 (3H, m), 7.71 (1H, s), 8.34 (1H br) | m/z = 337 (M + H) |
| 1-53 | (structure) | 7.23 (1H, m), 7.42 (1H, m), 7.50 (1H, m), 7.75 (1H, m), 8.27 (1H, br) | m/z = 305 (M + H) |
| 1-54 | (structure) | 7.38 (2H, d), 7.50 (1H, m), 7.60 (1H, d), 8.21 (1H, br) | m/z = 287 (M + H) |

TABLE 18-continued
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-55 | 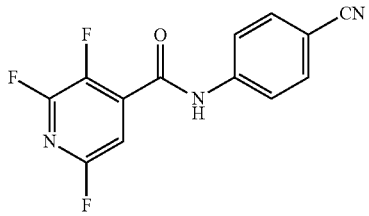 [SMILES: N#Cc1ccc(NC(=O)c2cc(F)nc(F)c2F)cc1] | 7.52 (1H, m), 7.72 (2H, d), 7.80 (2H, d), 8.37 (1H, br) | m/z = 278 (M + H) |
| 1-56 | 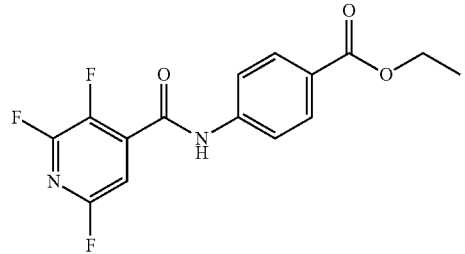 [SMILES: CCOC(=O)c1ccc(NC(=O)c2cc(F)nc(F)c2F)cc1] | 1.41 (3H, t), 4.40 (2H, q), 7.52 (1H, m), 7.73 (2H, d), 8.10 (2H, d), 8.35 (1H, br) | m/z = 325 (M + H) |
| 1-57 | 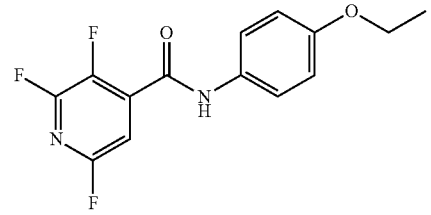 | 1.43 (3H, t), 4.05 (2H, q), 6.92 (2H, m), 7.52 (3H, m) | m/z = 297 (M + H) |
| 1-58 | 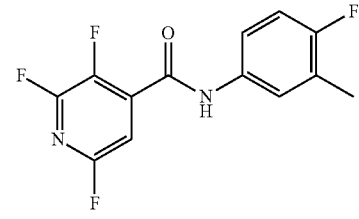 [SMILES: Cc1cc(NC(=O)c2cc(F)nc(F)c2F)ccc1F] | 2.31 (3H, s), 7.04 (1H, m), 7.39 (1H, m), 7.49 (2H, m), 8.16 (1H, br) | m/z = 285 (M + H) |
| 1-59 | 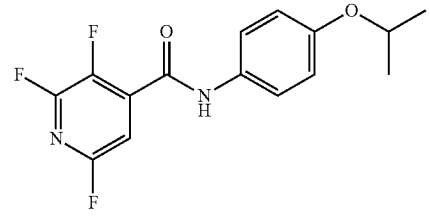 [SMILES: CC(C)Oc1ccc(NC(=O)c2cc(F)nc(F)c2F)cc1] | 1.34 (6H, d), 4.55 (1H, sep), 6.92 (2H, d), 7.53 (3H, m), 8.14 (1H, br) | m/z = 311 (M + H) |
| 1-60 | 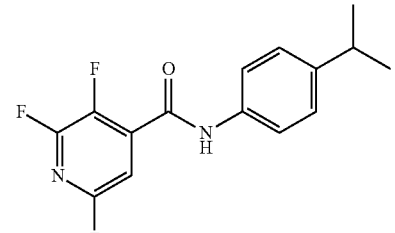 | 1.26 (6H, d), 2.93 (1H, sep), 7.28 (2H, d), 7.54 (3H, m) | m/z = 295 (M + H) |

TABLE 19

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-61 | | 3.83 (3H, s), 6.94 (2H, d), 7.51 (1H, m), 7.54 (2H, d) | m/z = 283 (M + H) |
| 1-62 | | 3.93 (3H, s), 6.70 (1H, m), 7.45 (1H, m), 7.91 (1H, s), 8.14 (1H, d), 8.86 (1H, br) | m/z = 284 (M + H) |
| 1-63 | | 2.21 (1H, s), 3.88 (1H, s), 6.93 (1H, d), 7.13 (1H, d), 7.38 (1H, s), 7.51 (1H, m), 8.19 (1H, br) | m/z = 297 (M + H) |
| 1-64 | | 2.62 (3H, s), 7.40 (1H, d), 7.52 (1H, m), 7.81 (1H, dd), 8.32 (1H, d), 8.35 (1H, br) | m/z = 312 (M + H) |
| 1-65 | | 2.49 (3H, s), 7.34 (1H, d), 7.52 (1H, m), 7.75 (1H, dd), 7.85 (1H, d), 8.26 (1H, br) | m/z = 335 (M + H) |
| 1-66 | | 2.37 (3H, s), 7.21 (2H, d), 7.51 (3H, m), 8.17 (1H, br) | m/z = 267 (M + H) |
| 1-67 | | 7.53 (1H, m), 7.85 (2H, d), 8.31 (2H, d), 8.48 (1H, br) | m/z = 298 (M + H) |

TABLE 19-continued

| Example | Formula | ¹H-NMR (measured at 400 MHz, 500 MHz, or 600 MHz) δ ppm | ESI MS (m/z) or IR (KBr) cm$^{-1}$ |
|---|---|---|---|
| 1-68 | | 7.04 (4H, m), 7.13 (1H, m), 7.35 (2H, m), 7.52 (1H, m), 7.60 (2H, m) | m/z = 345 (M + H) |
| 1-69 | | 7.44 (1H, m), 7.70 (2H, d), 8.53 (2H, d), 10.36 (1H, br) | m/z = 254 (M + H) |
| 1-70 | | 1.36 (9H, s), 7.04 (2H, d), 7.53 (3H, m) | m/z = 325 (M + H) |

TABLE 20

| Example | Formula | ¹H-NMR (measured at 400 MHz, 500 MHz, or 600 MHz) δ ppm | ESI MS (m/z) or IR (KBr) cm$^{-1}$ |
|---|---|---|---|
| 1-71 | | 1.33 (s, 9H), 7.42-7.56 (m, 5H), 8.15-8.23 (m, 1H) | m/z = 309 (M + H) |
| 1-72 | | 7.27 (2H, m), 7.51 (1H, m), 7.68 (2H, m), 8.26 (1H, br) | m/z = 337 (M + H) |
| 1-73 | | 2.47 (3H, s), 6.79 (1H, s), 7.46 (1H, m) | m/z = 258 (M + H) |

TABLE 20-continued

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-74 | | 2.46 (3H, s), 7.12 (1H, s), 7.48 (1H, m) | m/z = 274 (M + H) |
| 1-75 | | 4.68 (2H, d), 7.32-7.40 (5H, m), 7.46 (1H, m) | m/z = 267 (M + H) |
| 1-76 | | 1.48 (s, 9H), 6.39 (br s, 1H), 7.37 (t, J = 2.9 Hz, 1H) | |
| 1-77 | | 3.65-3.68 (m, 2H), 3.85-3.86 (m, 2H), 4.04 (s, 3H), 7.01 (t, J = 2.8 Hz, 1H), 7.09 (br s, 1H) | |
| 1-78 | | 1.92 (1H, br), 3.69 (2H, m), 3.87 (2H, br), 7.43 (1H, m) | m/z = 221 (M + H) |
| 1-79 | | 1.64 (bs, 1H), 2.79-2.84 (m, 2H), 3.67-3.72 (M, 2H), 7.05 (br s, 1H), 7.42-7.44 (m, 1H) | |
| 1-80 | | 4.68 (2H, d), 7.32-7.40 (5H, m), 7.46 (1H, m) | m/z = 267 (M + H) |

TABLE 21

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-81 | | 4.00 (2H, m), 5.30 (1H, m), 7.33-7.43 (6H, m) | IR 1654, 1542, 1466, 1437, 1383, 1053, 1030, 754 |
| 1-82 | | 1.29 (6H, d), 4.30 (1H, dsep), 6.40 (1H, br), 7.42 (1H, m) | |
| 1-83 | | 1.62 (3H, d), 5.53 (1H, m), 7.02 (1H, br), 7.27 (1H, dd), 7.30 (1H, d), 7.39 (1H, m), 7.42 (1H, d) | m/z = 349 (M + H) |
| 1-84 | | 1.63 (3H, d), 5.30 (1H, m), 6.81 (1H, br), 7.32 (2H, m), 7.37 (2H, m), 7.42 (1H, m) | m/z = 315 (M + H) |
| 1-85 | | 1.65 (3H, d), 5.34 (1H, m), 6.84 (1H, br), 7.31-7.44 (6H, m) | m/z = 281 (M + H) |
| 1-86 | | 3.81 (3H, s), 4.28 (2H, d), 7.42 (1H, m) | IR 1747, 1655, 1553, 1466, 1428, 1383, 1218, 1032, 771 |
| 1-87 | | 3.60 (2H, m), 3.92 (2H, m), 7.12 (1H, br), 7.40 (1H, m) | IR 3295, 1742, 1663, 1636, 1543, 1470, 1429, 1375, 1359, 1032, 1013 |

TABLE 21-continued
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-88 | 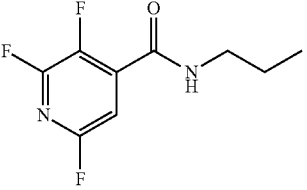 | 1.00 (3H, t), 1.68 (2H, sext), 3.48 (2H, m), 7.43 (1H, m) | m/z = 219 (M + H) |
| 1-89 | 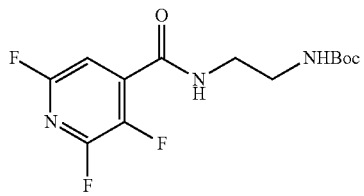 [SMILES: CC(C)(C)OC(=O)NCCNC(=O)c1cc(F)nc(F)c1F] | 1.43 (9H, s), 3.41 (2H, dd), 3.60 (2H, dd), 4.91 (1H, br), 7.36 (1H, s), 7.52 (1H, br) | m/z = 320 (M + H) |
| 1-90 | 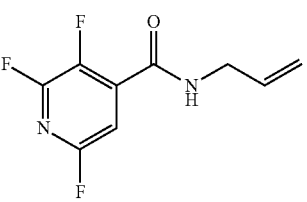 | 4.14 (2H, m), 5.25-5.32 (2H, m), 5.93 (1H, m), 6.67 (1H, br), 7.44 (1H, m) | m/z = 217 (M + H) |
TABLE 22
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-91 | 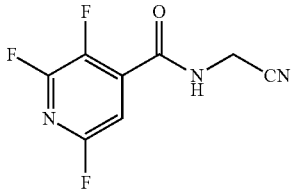 [SMILES: N#CCNC(=O)c1cc(F)nc(F)c1F] | 4.43 (2H, d), 6.99 (1H, br), 7.48 (1H, s) | |
| 1-92 | 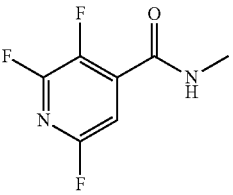 | 3.08 (3H, d), 6.65 (1H, br), 7.45 (1H, m) | m/z = 191 (M + H) |
| 1-93 | 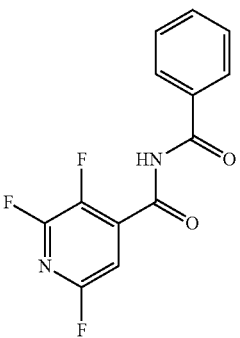 [SMILES: O=C(NC(=O)c1cc(F)nc(F)c1F)c1ccccc1] | 7.06 (1H, m), 7.61 (2H, m), 7.70 (1H, m), 8.10 (2H, m) | IR 1712, 1634, 1465, 1453, 1375, 1197, 1167, 851, 541 |

TABLE 22-continued

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-94 | | 1.26 (3H, m), 1.43 (2H, m), 1.65 (1H, m), 1.77 (2H, m), 2.02 (2H, m), 4.00 (1H, m), 6.44 (1H, br), 7.42 (1H, m) | m/z = 259 (M + H) |
| 1-95 | | 0.68 (2H, m), 0.95 (2H, m), 2.95 (1H, m), 6.69 (1H, br), 7.44 (1H, m) | m/z = 217 (M + H) |
| 1-96 | | 0.88 (3H, t), 1.27-1.38 (10H, m), 1.64 (2H, m), 3.48 (2H, m), 6.95 (1H, br), 7.43 (1H, m) | m/z = 289 (M + H) |
| 1-97 | | 3.87 (3H, s), 7.40 (1H, m), 9.12 (1H, br) | m/z = 207 (M + H) |
| 1-98 | | 7.25 (1H, m), 7.42 (2H, m), 7.52 (1H, m), 7.64 (2H, d), 8.23 (1H br) | m/z = 253 (M + H) |
| 1-99 | | 4.57 (2H, s), 7.31 (4H, m), 7.39 (1H, s), 7.41 (1H, s), 7.48 (1H, d), 7.76 (1H, m), 7.85 (1H, s) | m/z = 420 (M + H) |

TABLE 22-continued

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-100 | | 5.53 (2H, s), 7.33 (3H, m), 7.44 (1H, d), 7.51 (1H, d) | m/z = 302 (M + H) |

TABLE 23

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-101 | | 7.47-7.51 (3H, m), 7.74 (1H, dt), 7.77 (1H, dd) | m/z = 279 (M + H) |
| 1-102 | | 2.34 (s, 3H), 5.40 (s, 2H), 7.15 (d, J = 8.3 Hz, 1H), 7.25-7.26 (m, 1H), 7.28-7.31 (m, 1H), 7.42-7.44 (m, 1H), 7.53-7.54 (m, 1H) | |
| 1-103 | | 3.85 (3H, s), 7.02 (2H, m), 7.16 (1H, dd), 7.29 (1H, m), 7.45 (1H, m) | m/z = 283 (M + H) |
| 1-104 | | 5.61 (2H, s), 7.32 (1H, m) | m/z = 341 (M + H) |
| 1-105 | | 5.39 (2H, s), 7.29-7.37 (4H, m), 7.43 (1H, s) | m/z = 302 (M + H) |

TABLE 23-continued
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-106 | 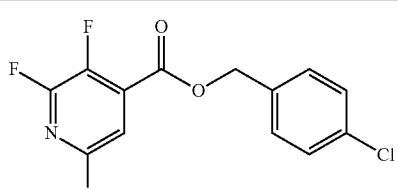 | 5.39 (2H, s), 7.28 (1H, m), 7.39 (4H, m) | m/z = 302 (M + H) |
| 1-107 | 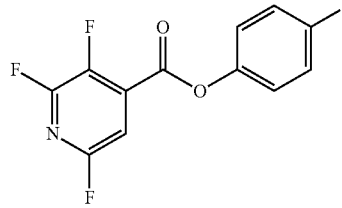 | 7.19 (2H, m), 7.44 (3H, m) | m/z = 288 (M + H) |
| 1-108 | 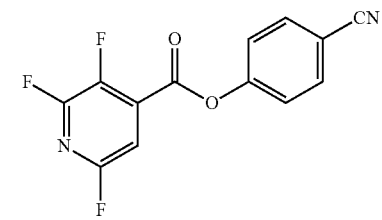 [SMILES: N#Cc1ccc(OC(=O)c2cc(F)nc(F)c2F)cc1] | 7.43 (3H, m), 7.79 (2H, dd) | m/z = 279 (M + H) |
| 1-109 | 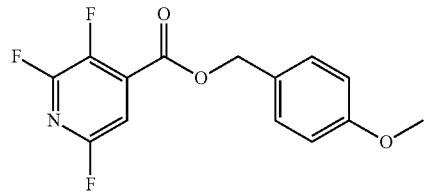 [SMILES: COc1ccc(COC(=O)c2cc(F)nc(F)c2F)cc1] | 3.82 (3H, s), 5.36 (2H, s), 6.93 (2H, d), 7.26 (1H, m), 7.38 (2H, d) | m/z = 298 (M + H) |
| 1-110 | 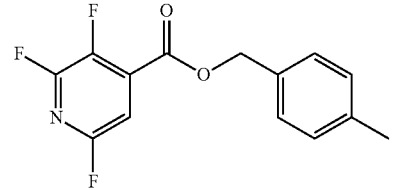 [SMILES: Cc1ccc(COC(=O)c2cc(F)nc(F)c2F)cc1] | 2.36 (3H, s), 5.38 (2H, s), 7.21 (2H, d), 7.26 (1H, m), 7.33 (2H, d) | m/z = 282 (M + H) |
TABLE 24
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-111 | 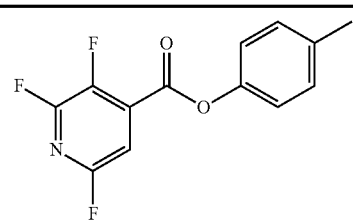 | 2.39 (3H, s), 7.11 (2H, dd), 7.25 (2H, dd), 7.42 (1H, m) | m/z = 268 (M + H) |

TABLE 24-continued
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-112 | 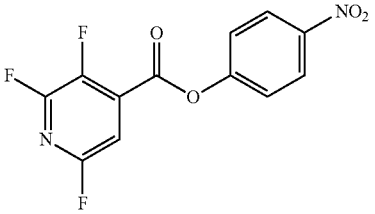 [SMILES: O=C(Oc1ccc([N+](=O)[O-])cc1)c1cc(F)nc(F)c1F] | 7.46 (3H, m), 8.37 (2H, m) | m/z = 299 (M + H) |
| 1-113 | 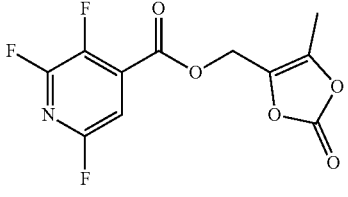 [SMILES: Cc1oc(=O)oc1COC(=O)c1cc(F)nc(F)c1F] | 2.24 (3H, s), 5.14 (2H, s), 7.29 (1H, m) | IR 1825, 1746, 1634, 1474, 1365, 1230, 1031, 770 |
| 1-114 | 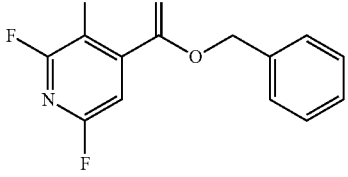 | 5.41 (2H, s), 7.28 (1H, m), 7.37-7.46 (5H, m) | m/z = 268 (M + H) |
| 1-115 | 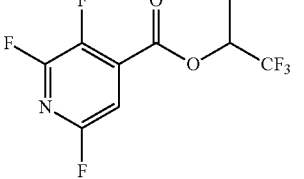 | 1.57 (d, J = 6.9 Hz, 3H), 5.53-5.58 (m, 1H), 7.29-7.30 (m, 1H) | |
| 1-116 | 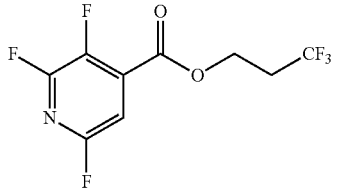 [SMILES: O=C(OCCC(F)(F)F)c1cc(F)nc(F)c1F] | 2.60-2.68 (m, 2H), 4.63 (t, J = 6.3 Hz, 2H), 7.27 (t, J = 2.8 Hz, 1H) | |
| 1-117 | 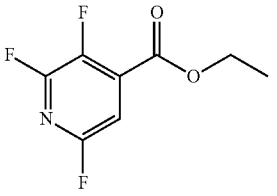 | 1.43 (3H, t), 4.47 (2H, q), 7.27 (1H, m) | m/z = 206 (M + H) |
| 1-118 | 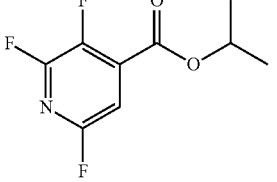 | 1.40 (6H, d), 5.30 (1H, sep), 7.25 (1H, m) | m/z = 220 (M + H) |

TABLE 24-continued
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-119 | 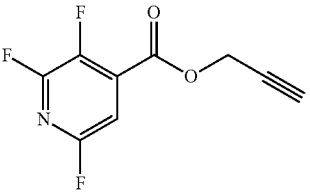 | 2.59 (1H, t), 4.99 (2H, d), 7.33 (1H, m) | m/z = 216 (M + H) |
| 1-120 | 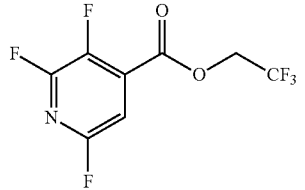 [SMILES: O=C(OCC(F)(F)F)c1cc(F)nc(F)c1F] | 4.76-4.79 (m, 2H), 7.31-7.32 (m, 1H) | |
TABLE 25
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-121 | 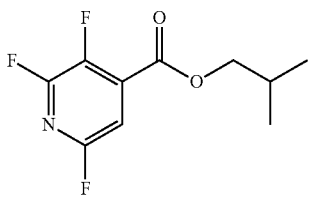 [SMILES: CC(C)COC(=O)c1cc(F)nc(F)c1F] | 1.03 (6H, d), 2.09 (1H, m), 4.19 (2H, d), 7.28 (1H, m) | IR 1732, 1472, 1439, 1384, 1366, 1276, 1256, 1034, 992, 758 |
| 1-122 | 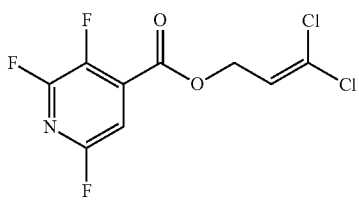 [SMILES: O=C(OCC=C(Cl)Cl)c1cc(F)nc(F)c1F] | 4.99 (2H, d), 6.18 (1H, t), 7.29 (1H, m) | IR 1740, 1437, 1439, 1387, 1361, 1250, 1207, 1035, 878 |
| 1-123 | 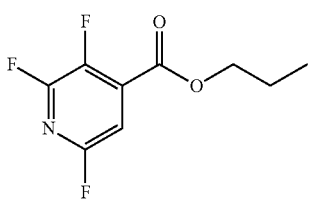 | 1.03 (3H, t), 1.81 (2H, sext), 4.37 (2H, t), 7.28 (1H, m) | m/z = 220 (M + H) |
| 1-124 | 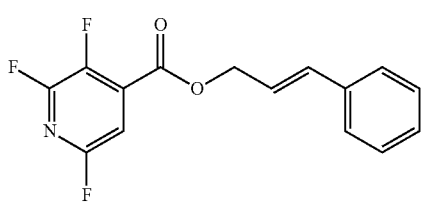 [SMILES: O=C(OC/C=C/c1ccccc1)c1cc(F)nc(F)c1F] | 5.06 (2H, d), 6.36 (1H, dt), 6.79 (1H, d), 7.29-7.34 (4H, m), 7.42 (2H, m) | m/z = 294 (M + H) |

TABLE 25-continued

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-125 | | 1.32 (3H, t), 4.28 (2H, q), 4.91 (2H, s), 7.35 (1H, m) | m/z = 264 (M + H) |
| 1-126 | | 4.01 (3H, s), 7.29 (1H, m), | m/z = 192 (M + H) |
| 1-127 | | 0.88 (3H, m), 1.27-1.39 (8H, m), 1.66 (2H, m), 1.77 (2H, m), 4.39 (2H, t), 7.28 (1H, m) | m/z = 290 (M + H) |
| 1-128 | | 4.90 (2H, d), 5.37 (1H, dd), 5.43 (1H, dd), 6.01 (1H, m), 7.30 (1H, m) | m/z = 218 (M + H) |
| 1-129 | | 7.24 (2H, d), 7.34 (1H, t), 7.43-7.48 (3H, m) | m/z = 254 (M + H) |
| 1-130 | | 7.22 (1H, m), 7.52 (5H, m) | m/z = 270 (M + H) |

TABLE 26
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-131 | 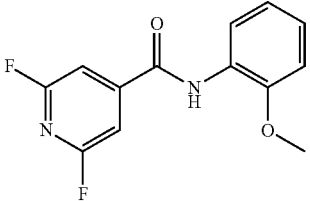 [SMILES: COc1ccccc1NC(=O)c1cc(F)nc(F)c1] | 3.96 (3H, s), 6.95 (1H, dd), 7.04 (1H, td), 7.15 (1H, td), 8.46 (2H, m) | m/z = 265 (M + H) |
| 1-132 | 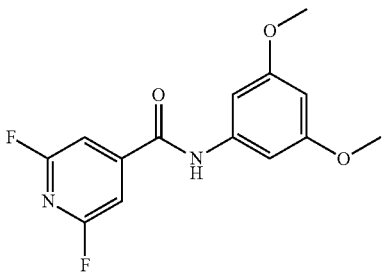 [SMILES: COc1cc(NC(=O)c2cc(F)nc(F)c2)cc(OC)c1] | 3.81 (6H, S), 6.34 (1H, t), 6.84 (2H, s), 7.24 (2H, s), 7.67 (1H, br) | m/z = 295 (M + H) |
| 1-133 | 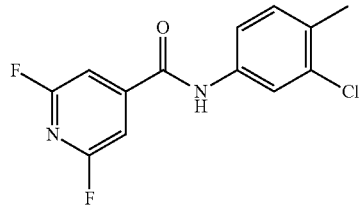 [SMILES: Cc1ccc(NC(=O)c2cc(F)nc(F)c2)cc1Cl] | 2.37 (3H, s), 7.24 (2H, s), 7.37 (1H, m), 7.71 (2H, m) | m/z = 283 (M + H) |
| 1-134 | 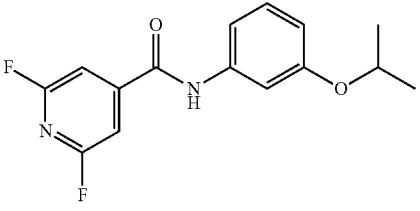 [SMILES: CC(C)Oc1cccc(NC(=O)c2cc(F)nc(F)c2)c1] | 1.36 (6H, d), 4.58 (1H, tt), 6.76 (1H, m), 7.05 (1H, m), 7.27 (3H, m), 7.33 (1H, s), 7.74 (1H, br) | m/z = 293 (M + H) |
| 1-135 | 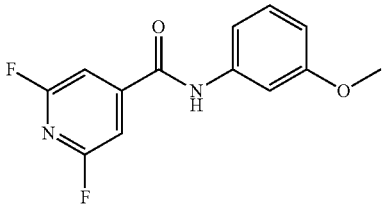 [SMILES: COc1cccc(NC(=O)c2cc(F)nc(F)c2)c1] | 3.84 (3H, s), 6.77 (1H, m), 7.10 (1H, m), 7.25 (2H, s), 7.30 (1H, t), 7.35 (1H, br), 7.77 (1H, br) | m/z = 265 (M + H) |
| 1-136 | 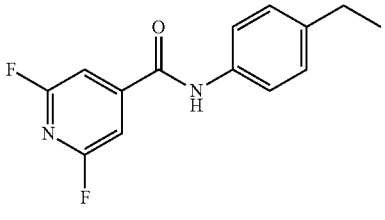 [SMILES: CCc1ccc(NC(=O)c2cc(F)nc(F)c2)cc1] | 1.25 (3H, t), 2.66 (2H, q), 7.22 (2H, s), 7.25 (2H, s), 7.51 (2H, d), 7.69 (1H, br) | m/z = 263 (M + H) |

TABLE 26-continued

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-137 | 2,6-difluoro-N-(4-isopropoxyphenyl)pyridine-4-carboxamide | 1.34 (6H, d), 4.54 (1H, m), 6.91 (2H, m), 7.24 (2H, s), 7.49 (2H, d), 7.66 (1H, s) | m/z = 293 (M + H) |
| 1-138 | 2,6-difluoro-N-(4-methoxyphenyl)pyridine-4-carboxamide | 3.83 (3H, s), 6.93 (2H, m), 7.25 (2H, d), 7.51 (2H, d), 7.69 (1H, br) | m/z = 265 (M + H) |
| 1-139 | 2,6-difluoro-N-(4-trifluoromethylphenyl)pyridine-4-carboxamide | 7.27 (2H, s), 7.53 (2H, m), 7.85 (1H, d), 7.93 (2H, m) | m/z = 303 (M + H) |
| 1-140 | N-benzyl-2,6-difluoropyridine-4-carboxamide | 4.64 (2H, d), 6.36 (1H, br), 7.16 (2H, s), 7.28 (5H, m) | m/z = 249 (M + H) |

TABLE 27

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-141 | N-[1-(4-chlorophenyl)ethyl]-2,6-difluoropyridine-4-carboxamide | 1.61 (3H, d), 5.27 (1H, m), 6.26 (1H, br) 7.13 (2H, s), 7.33 (4H, m) | m/z = 297 (M + H) |
| 1-142 | 2,6-difluoro-N-propylpyridine-4-carboxamide | 1.00 (3H, t), 1.67 (2H, td), 3.44 (2H, q), 6.11 (1H, br), 7.14 (2H, s) | m/z = 201 (M + H) |

TABLE 27-continued

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-143 | | 7.21 (3H, m), 7.41 (2H, m), 7.61 (2H, d) | m/z = 234 (M + H) |
| 1-144 | | 2.95 (2H, t), 3.74 (2H, dd), 6.07 (1H, br), 7.03 (2H, s), 7.26 (3H, m), 7.37 (2H, m) | m/z = 263 (M + H) |
| 1-145 | | 2.32 (s, 3H), 5.38 (s, 2H), 7.15 (d, J = 8.2 Hz, 1H), 7.26-7.37 (m, 3H), 7.44 (t, J = 7.7 Hz, 1H), 7.51 (d, J = 7.4 Hz, 1H) | |
| 1-146 | | 7.21-7.26 (m, 1H), 7.39-7.43 (m, 2H), 7.62-7.64 (m, 2H), 7.91-7.95 (m, 2H), 8.10 (s, 1H), 8.90-8.92 (m, 1H) | |
| 1-147 | | 1.44 (t, 3H), 4.47 (q, 2H), 8.06-8.07 (m, 1H), 8.23 (s, 1H), 8.90 (m, 1H) | |
| 1-148 | | 3.92-3.96 (m, 2H), 4.61-4.64 (m, 2H), 7.00 (br s, 1H), 7.30-7.32 (m, 1H), 7.43 (s, 1H) | |

TABLE 27-continued

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-149 | | 7.52 (2H, m), 7.72 (4H, s) | m/z = 427 (M + H) |
| 1-150 | | 2.83 (2H, m), 3.69 (2H, m), 7.30 (2H, m), 8.06 (1H, br) | m/z = 379 (M + H) |

TABLE 28

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-151 | | 5.10 (4H, d), 6.00 (2H, t), 7.31 (2H, m) | m/z = 407 (M + H) |
| 1-152 | | 4.97 (4H, d), 6.11 (2H, t), 7.32 (2H, m) | m/z = 407 (M + H) |
| 1-153 | | 7.25 (m, 2H), 7.36-7.40 (m, 2H), 7.57-7.59 (m, 2H), 7.72 (br s, 1H) | m/z = 267 (M − H) |

TABLE 28-continued

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-154 | | 7.16-7.27 (m, 5H), 7.97 (br s, 1H), 8.38 (t, J = 7.8 Hz, 1H) | m/z = 251 (M − H) |
| 1-155 | | 7.24 (m, 2H), 7.43-7.49 (m, 2H), 7.72 (br s, 1H), 7.88 (d, J = 2.1 Hz, 1H) | m/z = 301 (M − H) |
| 1-156 | | 1.33 (s, 9H), 7.25 (m, 2H), 7.41-7.44 (m, 2H), 7.52-7.54 (m, 2H), 7.69 (br s, 1H) | m/z = 291 (M + H) |
| 1-157 | | 1.31 (s, 9H), 7.17-7.23 (m, 4H), 7.89 (br s, 1H), 8.24 (t, J = 8.4 Hz, 1H) | m/z = 309 (M + H) |
| 1-158 | | 1.29 (d, J = 6.6 Hz, 6H), 4.23-4.32 (m, 1H), 5.88 (br s, 1H), 7.13 (s, 2H) | m/z = 201 (M + H) |
| 1-159 | | 4.08-4.12 (m, 2H), 5.24-5.32 (m, 2H), 5.87-5.97 (m, 1H), 6.16 (br s, 1H), 7.16 (s, 2H) | m/z = 199 (M + H) |

TABLE 28-continued
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-160 | 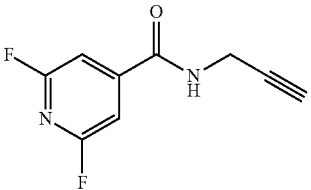 | 2.34 (t, J = 2.6 Hz, 1H), 4.26-4.28 (m, 2H), 6.29 (br s, 1H), 7.17 (s, 2H) | m/z = 197 (M + H) |
TABLE 29
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-161 | 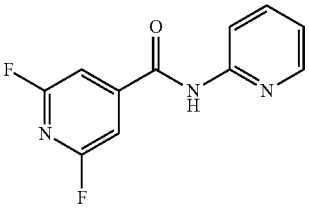 [SMILES: O=C(Nc1ccccn1)c1cc(F)nc(F)c1] | 7.14-7.18 (m, 1H), 7.31 (m, 2H), 7.79-7.83 (m, 1H), 8.31-8.34 (m, 2H), 8.54 (br s, 1H) | m/z = 236 (M + H) |
| 1-162 | 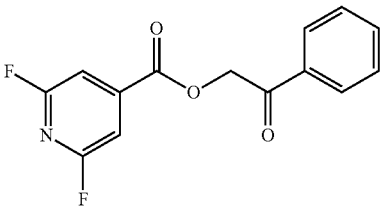 [SMILES: O=C(COC(=O)c1cc(F)nc(F)c1)c1ccccc1] | 5.64 (s, 2H), 7.50 (m, 2H), 7.52-7.56 (m, 2H), 7.64-7.69 (m, 1H), 7.94-7.97 (m, 2H) | m/z = 278 (M + H) |
| 1-163 | 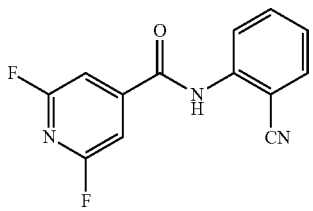 [SMILES: N#Cc1ccccc1NC(=O)c1cc(F)nc(F)c1] | 7.31-7.35 (m, 3H), 7.68-7.73 (m, 2H), 8.25 (br s, 1H), 8.50 (d, J = 8.4 Hz, 1H) | m/z = 258 (M + H) |
| 1-164 | 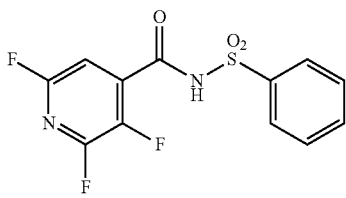 [SMILES: O=C(NS(=O)(=O)c1ccccc1)c1cc(F)nc(F)c1F] | 7.13-7.14 (m, 1H), 7.53-7.56 (m, 2H), 7.66-7.68 (m, 1H), 7.87-7.89 (m, 2H), 9.33 (br s, 1H) | |
| 1-165 | 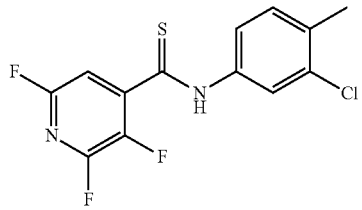 [SMILES: Cc1ccc(NC(=S)c2cc(F)nc(F)c2F)cc1Cl] | 2.41 (s, 3H), 7.31-7.36 (m, 2H), 7.50-7.52 (m, 1H), 7.83-7.84 (m, 1H), 9.04 (br s, 1H) | m/z = 315.01 (M − H) |

TABLE 29-continued
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-166 | 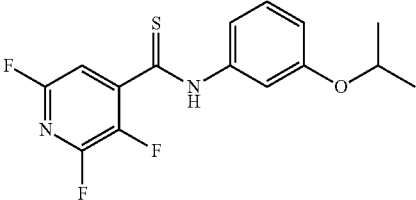 [SMILES: CC(C)Oc1cccc(NC(=S)c2cc(F)nc(F)c2F)c1] | 1.37 (d, J = 6.1 Hz, 6H), 4.55-4.60 (m, 1H), 6.87-6.89 (m, 1H), 7.13-7.17 (m, 1H), 7.32-7.36 (m, 2H), 7.57-7.58 (m, 1H), 9.06 (br s, 1H) | m/z = 325.07 (M − H) |
| 1-167 | 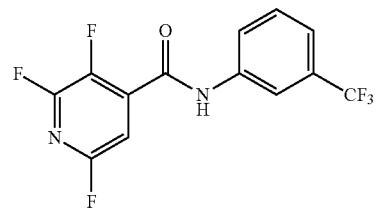 [SMILES: O=C(Nc1cccc(C(F)(F)F)c1)c1cc(F)nc(F)c1F] | 7.50 (m, 3H), 7.82-7.84 (m, 1H), 7.96 (s, 1H), 8.31-8.33 (m, 1H) | |
| 1-168 | 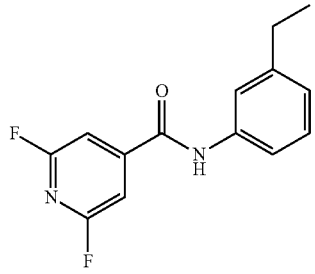 [SMILES: CCc1cccc(NC(=O)c2cc(F)nc(F)c2)c1] | 1.26 (3H, t), 2.68 (2H, q), 7.06-7.08 (1H, m), 7.25-7.34 (3H, m), 7.42-7.46 (2H, m), 7.70 (1H, br s) | m/z = 263 (M + H) |
| 1-169 | 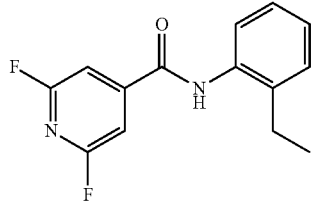 [SMILES: CCc1ccccc1NC(=O)c1cc(F)nc(F)c1] | 1.29 (3H, t), 2.67 (2H, q), 7.22-7.31 (5H, m), 7.83 (1H, br s), 7.83-7.84 (1H, m) | m/z = 263 (M + H) |
| 1-170 | 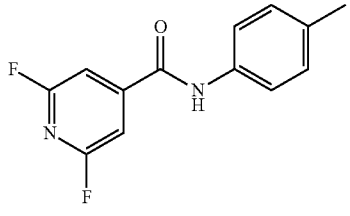 [SMILES: Cc1ccc(NC(=O)c2cc(F)nc(F)c2)cc1] | 2.36 (3H, s), 7.20-7.26 (4H, m), 7.48-7.52 (2H, m), 7.68 (1H, br s) | m/z = 247 (M − H) |
TABLE 30
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-171 | 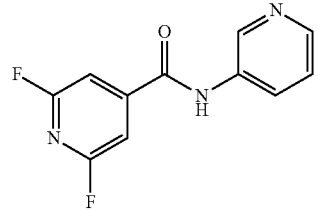 [SMILES: O=C(Nc1cccnc1)c1cc(F)nc(F)c1] | 7.26-7.28 (2H, m), 7.37-7.40 (1H, m), 7.91 (1H, br s), 8.24-8.26 (1H, m), 8.47-8.48 (1H, m), 8.70-8.71 (1H, m) | m/z = 234 (M − H) |

TABLE 30-continued
| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 1-172 | 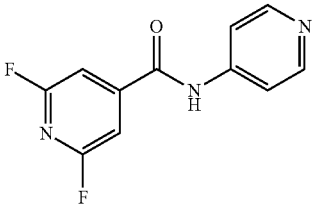 [SMILES: O=C(Nc1ccncc1)c1cc(F)nc(F)c1] | 7.27 (2H, m), 7.59-7.61 (2H, m), 7.97 (1H, brs), 8.61-8.62 (2H, m) | m/z = 234 (M – H) |
| 1-173 | 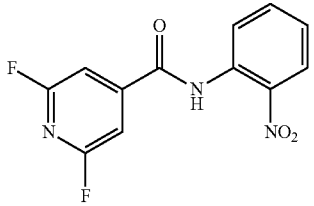 | 7.32-7.36 (3H, m), 7.76-7.80 (1H, m), 8.32-8.35 (1H, m), 8.91-8.94 (1H, m), 11.43 (1H, br s) | m/z = 278 (M – H) |
| 1-174 | 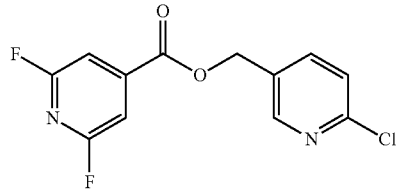 [SMILES: O=C(OCc1ccc(Cl)nc1)c1cc(F)nc(F)c1] | 5.40 (2H, s), 7.26-7.41 (4H, m), 7.74-7.77 (1H, m), 8.50 (1H, m) | m/z = 285 (M + H) |
| 1-175 | 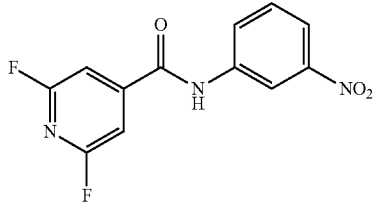 [SMILES: O=C(Nc1cccc([N+](=O)[O-])c1)c1cc(F)nc(F)c1] | 7.65 (2H, m), 7.71-7.76 (1H, m), 8.07-8.10 (1H, m), 8.24-8.27 (1H, m), 8.83-8.85 (1H, m), 10.25 (1H, brs) | m/z = 278 (M – H) |
| 1-176 | 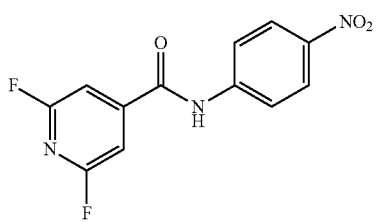 [SMILES: O=C(Nc1ccc([N+](=O)[O-])cc1)c1cc(F)nc(F)c1] | 7.64 (2H, s), 8.10-8.14 (2H, m), 8.31-8.35 (2H, m), 10.33 (1H, br s) | m/z = 278 (M – H) |
| 1-177 | 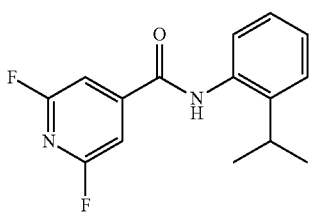 | 1.29 (6H, d, J = 6.85 Hz), 3.01-3.08 (1H, m), 7.26-7.32 (4H, m), 7.36-7.38 (1H, m), 7.68-7.70 (2H, m) | m/z = 277 (M + H) |

TABLE 30-continued
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-178 | 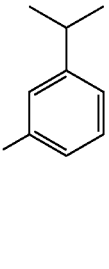 | 1.27 (6H, d, J = 6.85 Hz), 2.90-2.97 (1H, m), 7.09-7.11 (1H, d), 7.25-7.35 (3H, m), 7.45-7.46 (2H, m), 7.74 (1H, br s) | m/z = 277 (M + H) |
| 1-179 | 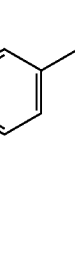 | 1.26 (6H, d, J = 6.85 Hz), 2.89-2.96 (1H, m), 7.24-7.27 (4H, m), 7.51-7.53 (2H, m), 7.74 (1H, br s) | m/z = 277 (M + H) |
| 1-180 |  | 0.93 (3H, t, J = 7.34 Hz), 1.31-1.40 (2H, m), 1.56-1.64 (2H, m), 2.59-2.64 (2H, m), 7.20-7.26 (4H, m), 7.50 (2H, d, J = 8.31 Hz), 7.74 (1H, br s) | m/z = 291 (M + H) |
TABLE 31
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-181 | 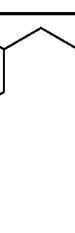 | 0.87-0.90 (3H, m), 1.26-1.37 (6H, m), 1.56-1.64 (2H, m), 2.59-2.63 (2H, m), 7.20-7.26 (4H, m), 7.49-7.51 (2H, m), 7.73 (1H, br s) | m/z = 319 (M + H) |
| 1-182 | 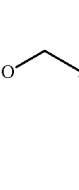 | 2.58 (1H, t), 4.98 (2H, d), 7.42-7.43 (2H, m) | m/z = 197 (M+) |
| 1-183 | 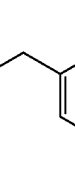 | 5.40 (2H, s), 7.38-7.44 (7H, m) | m/z = 249 (M+) |

TABLE 31-continued
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-184 | 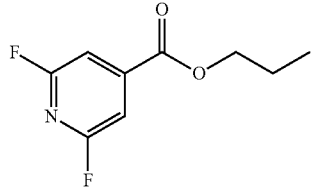 | 1.04 (3H, t), 1.77-1.86 (2H, m), 4.33-4.36 (2H, m), 7.38-7.39 (2H, m) | m/z = 201 (M +) |
| 1-185 | 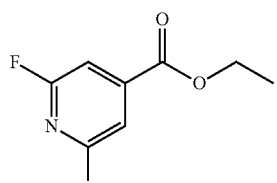 | 1.42 (3H, t), 4.44 (2H, q), 7.39 (2H, t) | m/z = 187 (M+) |
| 1-186 | 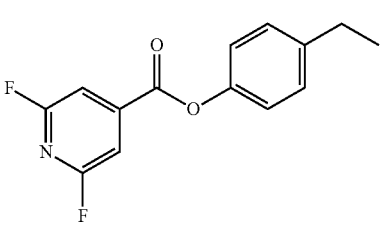 | 1.27 (3H, t), 2.69 (2H, q), 7.10-7.14 (2H, m), 7.26-7.29 (2H, m), 7.55 (2H, t) | m/z = 263 (M+) |
| 1-187 | 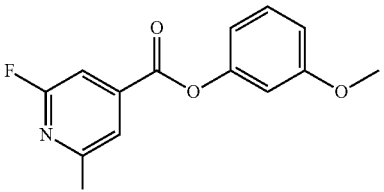 | 3.83 (3H, s), 6.76-6.89 (3H, m), 7.34-7.38 (1H, m), 7.55 (2H, t) | m/z = 265 (M+) |
| 1-188 | 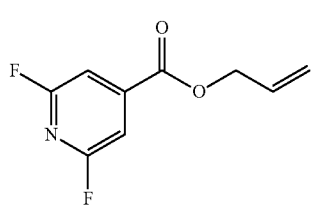 | 4.86-4.88 (2H, m), 5.35-5.47 (2H, m), 5.97-6.07 (1H, m), 7.41 (2H, t) | m/z = 199 (M+) |
| 1-189 | 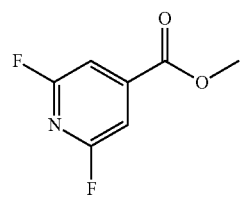 | 3.99 (3H, s), 7.39 (2H, t) | m/z = 173 (M+) |
| 1-190 | 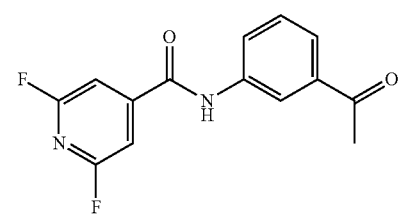 [SMILES: CC(=O)c1cccc(NC(=O)c2cc(F)nc(F)c2)c1] | 2.51 (s, 3H), 7.08-7.14 (m, 1H), 7.26 (s, 1H), 7.32 (s, 2H), 7.59 (s, 1H), 7.74 (br. S., 1H) | m/z = 277 (M + H) |

TABLE 32

| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-191 | 2,6-difluoro-N-(3-(trifluoromethyl)phenyl)isonicotinamide | 7.26-7.27 (s, 1H), 7.50-7.55 (m, 2H), 7.83-7.85 (d, 1H), 7.90 (s, 1H), 7.92 (s, 1H) | m/z = 303 (M + H) |
| 1-192 | 2,6-difluoro-N-(3-(methylthio)phenyl)isonicotinamide | 6.59-6.60 (m, 3H), 11.47-11.49 (m, 3H), 11.79 (m, 1H), 11.95 (m, 1H), 12.33 (m, 1H) | m/z = 281 (M + H) |
| 1-193 | 2,6-difluoro-N-(3-hydroxyphenyl)isonicotinamide | 6.65-6.73 (m, 1H), 7.05-7.12 (d, 1H), 7.20 (s, 2H), 7.31 (s, 1H) 7.36 (s, 2H), 8.88 (br. S., 1H), 9.52 (br. S, 1H) | m/z = 251 (M + H) |
| 1-194 | N-(benzo[d]thiazol-2-yl)-2,6-difluoroisonicotinamide | | m/z = 292 (M + H) |
| 1-195 | N,N'-(1,3-phenylene)bis(2,6-difluoroisonicotinamide) | 7.38-7.40 (t, 1H), 7.47 (s, 4H), 7.50 (d, 1H), 7.52 (d, 1H), 8.26-8.27 (t, 1H) | m/z = 391 (M + H) |
| 1-196 | N-(3-aminophenyl)-2,6-difluoroisonicotinamide | 6.54-6.57 (m, 1H), 6.94-6.96 (m, 1H), 7.06-7.10 (t, 1H), 7.15-7.16 (t, 1H), 7.44 (s, 2H) | m/z = 258 (M + H) |

TABLE 32-continued
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-197 | 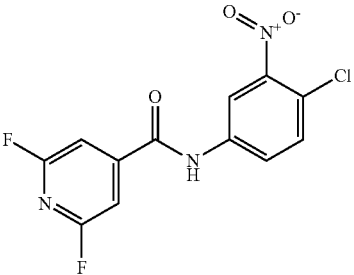 | 7.50 (s, 2H), 7.65-7.67 (d, 1H), 7.93-7.96 (dd, 1H), 8.47-8.48 (d, 1H) | m/z = 312 (M − H) |
| 1-198 | 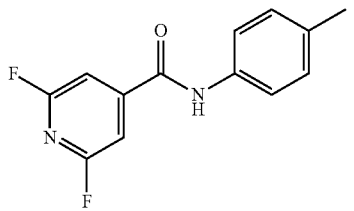 [SMILES: Cc1ccc(NC(=O)c2cc(F)nc(F)c2)cc1] | 2.39 (3H, s), 7.08-7.11 (2H, m), 7.24-7.26 (2H, m), 7.55 (2H, t) | m/z = 250 (M + H) |
| 1-199 | 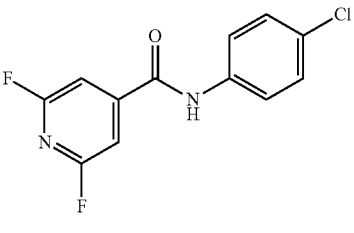 [SMILES: O=C(Nc1ccc(Cl)cc1)c1cc(F)nc(F)c1] | 7.16-7.20 (2H, m), 7.41-7.45 (2H, m), 7.54 (2H, t) | m/z = 270 (M + H) |
| 1-200 | 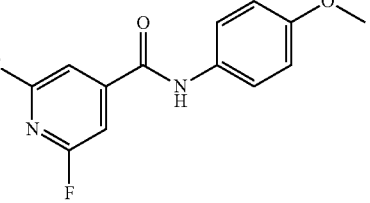 | 3.84 (3H, s), 6.94-6.98 (2H, m), 7.13-7.16 (2H, m), 7.54 (2H, t) | m/z = 265 (M+) |
TABLE 33
| Example | Formula | ¹H-NMR (measured at 400 MHz, 500 MHz, or 600 MHz) δ ppm | ESI MS (m/z) or IR (KBr) cm⁻¹ |
|---|---|---|---|
| 1-201 | 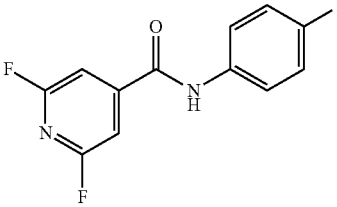 | 7.12-7.22 (4H, m), 7.54 (2H, t) | m/z = 253 (M+) |
| 1-202 | 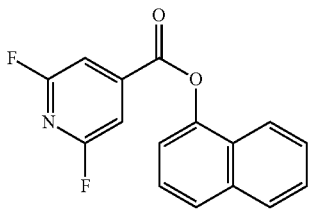 [SMILES: O=C(Oc1cccc2ccccc12)c1cc(F)nc(F)c1] | 7.38-7.40 (1H, m), 7.52-7.59 (3H, m), 7.68 (2H, m), 7.82-7.95 (3H, m) | m/z = 285 (M+) |

TABLE 33-continued
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-203 | 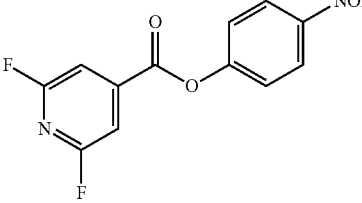 | 6.89-6.93 (1H, m), 7.48-7.57 (3H, m), 8.18-8.20 (1H, m), 8.35-8.39 (1H, m) | m/z = 280 (M+) |
| 1-204 | 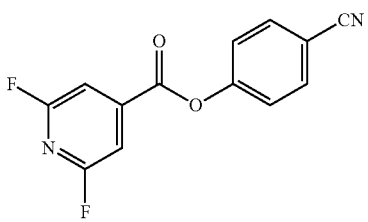 [SMILES: N#Cc1ccc(OC(=O)c2cc(F)nc(F)c2)cc1] | 7.38-7.41 (2H, m), 7.54-7.57 (2H, m), 7.77-7.81 (2H, m) | m/z = 260 (M+) |
| 1-205 | 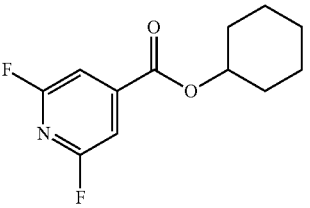 [SMILES: O=C(OC1CCCCC1)c1cc(F)nc(F)c1] | 1.37-1.64 (6H, m), 1.78-1.81 (2H, m), 1.94-1.99 (2H, m), 5.03-5.09 (1H, m), 7.38 (2H, m) | m/z = 241 (M+) |
| 1-206 | 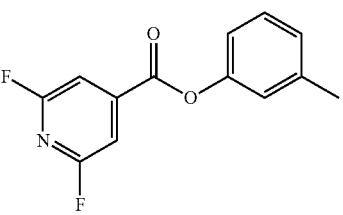 [SMILES: Cc1cccc(OC(=O)c2cc(F)nc(F)c2)c1] | 2.41 (3H, s), 7.00-7.08 (2H, m), 7.13-7.15 (1H, m), 7.32-7.36 (1H, m), 7.55 (2H, t) | m/z = 249 (M+) |
| 1-207 | 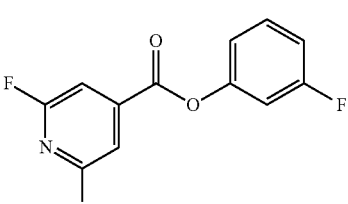 | 6.99-7.09 (3H, m), 7.40-7.46 (1H, m), 7.54 (2H, t) | m/z = 253 (M+) |
| 1-208 | 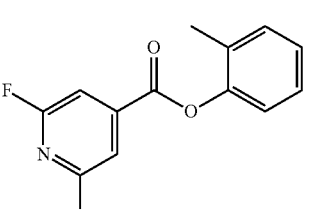 | 2.23 (3H, s), 7.12-7.14 (1H, m), 7.22-7.32 (3H, m), 7.57 (2H, t) | m/z = 249 (M+) |
| 1-209 | 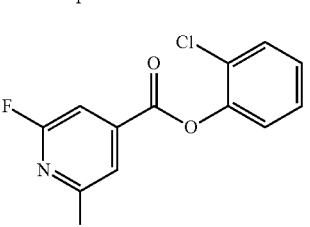 | 7.28-7.7.40 (3H, m), 7.51-7.54 (1H, m), 7.59 (2H, t) | m/z = 269 (M+) |

TABLE 33-continued

| Example | Formula | ¹H-NMR (measured at 400 MHz, 500 MHz, or 600 MHz) δ ppm | ESI MS (m/z) or IR (KBr) cm⁻¹ |
|---------|---------|---------------------------------------------------------|-------------------------------|
| 1-210 | | 3.83 (3H, s), 6.99-7.05 (2H, m), 7.14-7.16 (1H, m), 7.27-7.32 (1H, m), 7.56 (2H, m) | m/z = 265 (M+) |

TABLE 34

| Example | Formula | ¹H-NMR (measured at 400 MHz, 500 MHz, or 600 MHz) δ ppm | ESI MS (m/z) or IR (KBr) cm⁻¹ |
|---------|---------|---------------------------------------------------------|-------------------------------|
| 1-211 | | 7.20-7.35 (4H, m), 7.57 (2H, m) | m/z = 253 (M+) |
| 1-212 | | 7.13-7.16 (1H, m), 7.26-7.42 (3H, m), 7.54 (2H, t) | m/z = 269 (M+) |
| 1-213 | | 0.89-0.93 (3H, m), 1.26-1.47 (6H, m), 1.74-1.81 (2H, m), 4.37 (2H, t), 7.38 (2H, s) | m/z = 243 (M+) |
| 1-214 | | 0.88 (3H, t), 1.26-1.46 (18H, m), 1.74-1.81 (2H, m), 4.37 (2H, t), 7.38 (2H, m) | m/z = 327 (M+) |
| 1-215 | | 3.09 (2H, t), 4.59 (2H, t), 7.25-7.34 (6H, m), 7.36 (2H, m), | m/z = 244 (M − F) |

TABLE 34-continued

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 1-216 | (2,6-difluoropyridine-4-carboxylic acid cinnamyl ester) | 5.02-5.04 (2H, m), 6.33-6.41 (1H, m), 6.77 (1H, d), 7.27-7.44 (7H, m) | m/z = 275 (M+) |
| 1-217 | (2,6-difluoropyridine-4-carboxylic acid 4-isopropoxyphenyl ester) | 1.29-1.36 (6H, m), 4.51-4.57 (1H, m), 6.91-6.95 (2H, m), 7.09-7.13 (2H, m), 7.54 (2H, t) | m/z = 293 (M+) |
| 1-218 | (2,6-difluoropyridine-4-carboxylic acid phenyl ester) | 7.21-7.24 (2H, m), 7.31-7.36 (1H, m), 7.44-7.49 (2H, m), 7.56 (2H, m) | m/z = 234 (M − H) |

The compounds of Examples 2-1 to 2-5, represented by formula (3'), are shown in Table 35.

(3')

TABLE 35

| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 2-1 | (2,3,6-trifluoropyridin-4-yl)(piperidin-1-yl)methanone | 1.70 (6H, m), 3.26 (2H, m), 3.73 (2H, m), 6.82 (1H, m) | m/z = 245 (M + H) |
| 2-2 | (2,3,6-trifluoropyridin-4-yl)(1-methyl-1H-pyrrol-2-yl)methanone | 4.07 (3H, s), 6.21 (1H, dd), 6.65 (1H, dd), 6.91 (1H, m), 7.04 (1H, m) | IR 1638, 1630, 1467, 1155, 1023, 803, 7.53 |

TABLE 35-continued
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 2-3 | 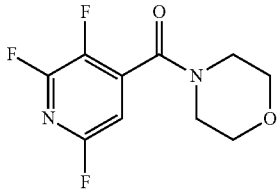 [SMILES: O=C(c1cc(F)nc(F)c1F)N1CCOCC1] | 3.35 (2H, m), 3.70 (2H, m), 3.81 (4H, m), 6.86 (1H, m) | m/z = 247 (M + H) |
| 2-4 | 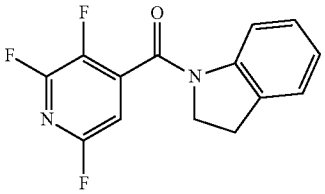 [SMILES: O=C(c1cc(F)nc(F)c1F)N1CCc2ccccc21] | 3.22 (t, J = 8.3 Hz, 2H), 3.94 (t, J = 8.3 Hz, 2H), 6.91-6.93 (m, 1H), 7.16-7.18 (m, 1H), 7.25-7.30 (m, 2H), 8.25 (d, J = 8.2 Hz, 1H) | |
| 2-5 | 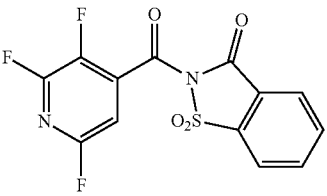 [SMILES: O=C1c2ccccc2S(=O)(=O)N1C(=O)c1cc(F)nc(F)c1F] | 7.84-7.95 (m, 4H), 8.05-8.07 (m, 1H) | |
The compounds of Examples 3-1 and 3-2, represented by formula (4'), are shown in Table 36.
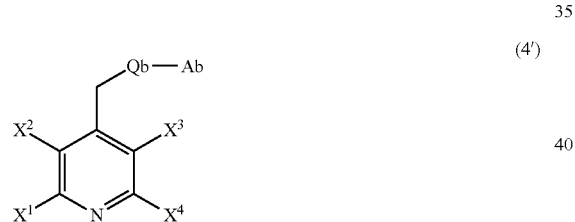
(4')
TABLE 36
| Example | Formula | $^1$H-NMR (measured at 400 MHz, 500 MHz, or 600 MHz) δ ppm | ESI MS (m/z) or IR (KBr) cm$^{-1}$ |
|---|---|---|---|
| 3-1 | 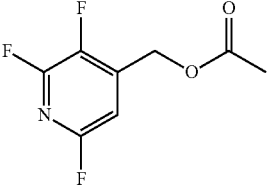 | 2.23 (3H, s), 5.24 (2H, s), 6.85 (1H, m) | |
| 3-2 | 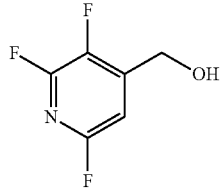 [SMILES: OCc1cc(F)nc(F)c1F] | 4.89 (2H, s), 7.05 (1H, m) | IR 1641, 1480, 1455, 1430, 1364, 1268, 1206, 1154, 1088, 1023, 972, 878, 805 |

The compounds of Examples 4-1 to 4-4, represented by formula (5'), are shown in Table 37.

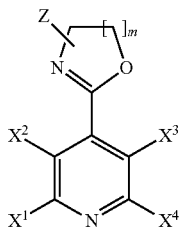

(5')

chambers. To the rice cultivated to the second leaf stage, the conidia suspension of *Pyricularia oryzae* prepared such that the content thereof became $1.5 \times 10^5$ conidia spores/mL to $5 \times 10^5$ conidia spores/mL was inoculated by conducting spraying, and then left still for 24 hours in a moist chamber (in which the temperature was 25° C. and the humidity was 100%). Then, the rice was continued to be cultivated in the plant cultivation chambers, and the number of lesions at the second leaf was counted. The control value was calculated based on the counted number of the lesions in accordance with the below-mentioned mathematical formula.

Control value=((the number of lesions at untreated plants −the number of lesions at treated plants)/ the number of lesions at untreated plants)×100

TABLE 37

| Example | Formula | $^1$H-NMR (measured at 400 MHz, 500 MHz, or 600 MHz) δ ppm | ESI MS (m/z) or IR (KBr) cm$^{-1}$ |
| --- | --- | --- | --- |
| 4-1 | | 1.29 (3H, s), 3.35 (1H, m), 3.74 (1H, m), 4.07 (1H, m), 7.42 (1H, m) | m/z = 217 (M + H) |
| 4-2 | | 4.12 (2H, t), 4.53 (2H, t), 7.41 (1H, m) | IR 1665, 1636, 1472, 1436, 1274, 1030, 996 |
| 4-3 | | 2.02 (2H, m), 3.65 (2H, m), 4.38 (2H, m), 7.24 (1H, m) | IR 1654, 1635, 1472, 1431, 1374, 1248, 1133, 1078, 1027, 957, 761 |
| 4-4 | | 4.13 (2H, t), 4.50 (2H, t), 7.33 (2H, s) | m/z = 185 (M + H) |

Example 9

<Activity Against Rice Blast Disease>

The acetone solution of each compound of each example was prepared such that the content thereof became 0.1 mg/mL, and then diluted to 10-fold with water to be subjected to conduct test. 0.25 mL of the diluted solution per 1 mL of the soil was made to be absorbed in the soil. Rice seeds (cultivar: Jikkoku) subjected to forcing to germination were seeded in the soil to be cultivated in plant cultivation The control values of the compounds of the below-mentioned examples were 80 or more, and control effects against the rice blast disease were confirmed.

1-1, 1-2, 1-3, 1-4, 1-5, 1-7, 1-9, 1-12, 1-14, 1-15, 1-16, 1-17, 1-18, 1-19, 1-20, 1-21, 1-22, 1-24, 1-25, 1-26, 1-27, 1-28, 1-29, 1-30, 1-32, 1-33, 1-35, 1-36, 1-37, 1-39, 1-40, 1-44, 1-46, 1-47, 1-48, 1-50, 1-51, 1-52, 1-54, 1-55, 1-56, 1-57, 1-58, 1-59, 1-61, 1-63, 1-64, 1-65, 1-66, 1-67, 1-68, 1-70, 1-71, 1-73, 1-74, 1-78, 1-79, 1-80, 1-81, 1-84, 1-85, 1-86, 1-87, 1-88, 1-91, 1-92, 1-93, 1-96, 1-98, 1-99, 1-100, 1-102, 1-103, 1-104, 1-105, 1-107, 1-108, 1-109, 1-110, 1-111, 1-112, 1-114, 1-115, 1-117, 1-118, 1-119, 1-120, 1-122, 1-123, 1-124, 1-125, 1-127, 1-130, 1-132, 1-133, 1-134, 1-135, 1-137, 1-138, 1-139, 1-140, 1-141, 1-143, 1-145, 1-146, 1-147, 1-151, 1-152, 1-153, 1-155, 1-159, 1-168, 1-169, 1-170, 1-173, 1-174, 1-175, 1-176, 1-178, 1-179, 1-180, 1-181, 1-182, 1-183, 1-184, 1-185, 1-186, 1-187, 1-188, 1-189, 1-190, 1-191, 1-192, 1-193, 1-194, 1-196, 1-197, 1-198, 1-199, 1-200, 1-201, 1-202, 1-203, 1-204, 1-205, 1-206, 1-207, 1-208, 1-209, 1-210, 1-211, 1-213, 1-214, 1-218, 2-2, 2-4, 2-5, 3-1, 4-2, 4-3, 4-4

Example 10

<Activity Against Rice Blast Disease>

The acetone solution of each compound of each example was prepared at an approximate concentration, and then diluted to 10-fold with water, followed by adding 1/1000-fold by volume of NEOESTERIN to the diluted solution to be subjected to conducting test. Each of the compounds was sprayed onto rice cultivated in pots to the second leaf stage or the third leaf stage, and then, one day after conducting spraying, the conidia suspension of *Pyricularia oryzae* prepared such that the content thereof became $1.5 \times 10^5$ conidia spores/mL to $5 \times 10^5$ conidia spores/mL was inoculated by conducting spraying, followed by leaving the rice still for 24 hours in a moist chamber (in which the temperature was 25° C. and the humidity was 100%). Then, the rice was cultivated in plant cultivation chambers, and the number of lesions at the second leaf was counted. The control value was calculated based on the counted number of the lesions in accordance with the below-mentioned mathematical formula.

Control value=((the number of lesions at untreated plants −the number of lesions at treated plants)/ the number of lesions at untreated plants)×100

The control values of the compounds of the below-mentioned examples were 80 or more at the concentration of 25 ppm, and control effects against the rice blast disease were confirmed.

1-19, 1-30, 1-38, 1-41, 1-44, 1-59, 1-134, 1-135, 1-139, 1-168, 1-172, 1-174

The control values of the compounds of the below-mentioned examples were 80 or more at the concentration of 200 ppm, and control effects against the rice blast disease were confirmed.

1-3, 1-18, 1-32, 1-33, 1-86, 1-93, 1-98, 1-102, 1-103, 1-105, 1-129, 1-131, 1-132, 1-133, 1-134, 1-135, 1-137, 1-138, 1-139, 1-168, 1-169, 1-170, 1-172, 1-173, 1-174, 1-175, 1-176, 1-177, 1-178, 1-179, 1-180, 1-183, 1-187, 1-190, 1-191, 1-193, 1-200, 1-202, 1-204, 1-210, 4-4

Example 11

<Activity Against Rice Bacterial Leaf Blight>

The acetone solution of each compound of each example was prepared such that the content thereof became 2 mg/mL, and then diluted to 10-fold with water, followed by adding 1/1000-fold by volume of NEOESTERIN to the diluted solution to be subjected to conducting test. Each of the compounds was sprayed onto rice cultivated in pots to the tillering stage, and then, three days after conducting spraying, *Xanthomonas oryzae* pv.*oryzae* was inoculated by leaving a scratch using needle tweezers. The rice was left still overnight in a moist chamber (in which the temperature was 21° C. and the humidity was 100%), and then cultivated in a greenhouse to measure the length of lesions (lesion length), 11 days after the inoculation. The control value was calculated based on an average of the measured lesion length in accordance with the below-mentioned mathematical formula.

Control value=((the lesion length at untreated plant −the lesion length at treated plant)/the lesion length at untreated plant)×100

The control values of the below-mentioned compounds were 50 or more at the concentration of 200 ppm, and control effects against the rice bacterial leaf blight were confirmed.

1-134, 1-135, 1-136, 1-161

Example 12

<Activity Against Barley Powdery Mildew>

The acetone solution of each compound of each example was prepared such that the content thereof became 2 mg/mL, and then diluted to 10-fold with water, followed by adding 1/1000-fold by volume of NEOESTERIN to the diluted solution to be subjected to conducting test. Each of the compounds was sprayed onto two-row barley cultivated in small bats (30 cm×20 cm) for approximately one month after seeding, and then, 7 days after conducting spraying, the two-row barley was left in a greenhouse under conditions in which natural infection of *Erysiphe graminis* was allowed, followed by cultivating the two-row barley for approximately 1 month under the conditions in which continuous infection thereof was allowed. The number of lesions at the flag leaf on the main stem was counted, and the control value was calculated based on the counted number of lesions in accordance with the below-mentioned mathematical formula.

Control value=((the number of lesions at untreated plants −the number of lesions at treated plants)/ the number of lesions at untreated plants)×100

The control values of the below-mentioned compounds were 50 or more at the concentration of 200 ppm, and control effects against the barley powdery mildew were confirmed.

1-41, 1-134, 1-135

Example 13

<Activity Against Wheat Powdery Mildew>

Wettable powders of example compounds 1-134 and 1-135 were prepared in accordance with the below-mentioned Preparation Example 1, respectively, followed by diluting the wettable powders to 1000-fold with water to prepare spraying liquids. The prepared spraying liquids were sprayed onto wheat twice at the blooming stage and 10 days prior to the blooming stage at a liquid volume of 1 L/m², respectively. The lesions on the flag leaf were examined in accordance with the below-mentioned indexes approximately 4 weeks after the second spraying application. The severity was calculated based on the indexes, and the control value was calculated from the obtained severity in accordance with the below-mentioned mathematical formula.

Indexes (0 to 5)

0: No lesions were observed.

1: 1 to 3 lesions were observed.

2: 4 to 10 lesions were observed.

3: 11 to 20 lesions were observed.

4: 21 or more lesions were observed, and the area of lesions was less than half of the leaf surface.

5: 21 or more lesions were observed, and the area of lesions was half or more of the leaf surface.

Control value=((the severity at untreated plants −the severity at treated plants)/the severity at untreated plants)×100

The control values of the example compounds 1-134 and 1-135 were 50 or more, and control effects were confirmed.

Example 14

<Activity Against Wheat Brown Rust>

Wettable powders of the example compound 1-135 were prepared in accordance with the below-mentioned Preparation Example 1, followed by diluting the wettable powders to 1000-fold with water to prepare spraying liquids. The prepared spraying liquid was sprayed onto wheat twice at the blooming stage and 10 days prior to the blooming stage at a liquid volume of 1 L/m². The lesions on the flag leaf were examined in accordance with the below-mentioned indexes approximately 4 weeks after the second spraying application. The severity was calculated based on the indexes, and the control value was calculated from the obtained severity in accordance with the below-mentioned mathematical formula.

Indexes (0 to 5)
0: No lesions were observed.
1: 1 to 3 lesions were observed.
2: 4 to 10 lesions were observed.
3: 11 to 20 lesions were observed.
4: 21 or more lesions were observed, and the area of lesions was less than half of the leaf surface.
5: 21 or more lesions were confirmed, and the area of lesions was half or more of the leaf surface.

Control value=((the severity at untreated plants −the severity at treated plants)/the severity at untreated plants)×100

The control value of the example compound 1-135 was 50 or more, and control effects against the wheat brown rust were confirmed.

Example 15

<Activity Against Cucumber Downy Mildew>

The acetone solution of each example compound was prepared such that the content thereof became 0.4 mg/mL, and then diluted to 10-fold with water to be subjected to conducting test. 5 mL of the diluted solution was made to be absorbed in the soil per pot at the root of cucumber (cultivar: Suyo) cultivated to the first-leaf stage in the pot. 7 days after the treatment, the spore suspension of *Pseudoperonospora cubensis* prepared such that the content thereof became $5 \times 10^4$ spores/mL was inoculated to the cucumber by conducting spraying, followed by leaving the cucumber still for 24 hours in a moist chamber (in which the temperature was 25° C. and the humidity was 100%). Then, the cucumber was cultivated in a greenhouse, and, 7 days after the inoculation, the lesions at the second leaf were examined in accordance with the below-mentioned indexes. The severity was calculated based on the indexes, and the control value was calculated from the obtained severity in accordance with the below-mentioned mathematical formula.

Indexes (0 to 5)
0: No lesions were observed.
1: The area of lesions was less than 5% of the leaf surface.
2: The area of lesions was 5% or more but less than 25% of the leaf surface.
3: The area of lesions was 25% or more but less than 50% of the leaf surface.
4: The area of lesions was 50% or more but less than 80% of the leaf surface.
5: The area of lesions was 80% or more of the leaf surface.

Control value=((the severity at untreated plants −the severity at treated plants)/the severity at untreated plants)×100

The control values of the below-mentioned compounds were 70 or more, and control effects against the cucumber downy mildew were confirmed.

1-117, 1-134, 1-135, 1-143, 1-218, 4-2

Example 16

<Activity Against Cucumber Downy Mildew>

The acetone solution of each example compound was prepared such that the content thereof became 1 mg/mL, and then diluted to 10-fold with water to be subjected to conducting test. 1 mL of the diluted solution per pot was sprayed onto cucumber (cultivar: Suyo) cultivated to the first-leaf stage in pots. 7 days after the spraying application, the spore suspension of *Pseudoperonospora cubensis* prepared such that the content thereof became $5 \times 10^4$ spores/mL was inoculated to the cucumber by conducting spraying, followed by leaving the cucumber still for 24 hours in a moist chamber (in which the temperature was 25° C. and the humidity was 100%). Then, the cucumber was cultivated in a greenhouse, and, 7 days after the inoculation, the area ratio of lesions at the second leaf was examined in accordance with the below-mentioned indexes. The severity was calculated based on the indexes, and the control value was calculated from the obtained severity in accordance with the below-mentioned mathematical formula.

Indexes (0 to 5)
0: No lesions were observed.
1: The area of lesions was less than 5% of the leaf surface.
2: The area of lesions was 5% or more but less than 25% of the leaf surface.
3: The area of lesions was 25% or more but less than 50% of the leaf surface.
4: The area of lesions was 50% or more but less than 80% of the leaf surface.
5: The area of lesions was 80% or more of the leaf surface.

Control value=((the severity at untreated plans −the severity at treated plants)/the severity at untreated plants)×100

The control values of the below-mentioned compounds were 70 or more, and control effects against the cucumber downy mildew were confirmed.

1-143, 1-218

Example 17

<Activity Against Cucumber Bacterial Spot Disease>

Wettable powders of the example compound 1-134 were prepared in accordance with the below-mentioned Preparation Example 1. The wettable powders were diluted to 6666-fold with water, and then 20 mL of the diluted solution per pot was applied to cucumber (cultivar: Natsusuzumi) cultivated to the third leaf stage in pots by making the diluted solution to be absorbed in the soil, and then the cucumber was subjected to settled planting. 28 days after the settled planting, the number of lesions formed at the 11$^{th}$ true leaves to the 20$^{th}$ true leaves were counted. The control value was calculated from the obtained number of lesions in accordance with the below-mentioned mathematical formula.

Control value=((the number of lesions at untreated plants −the number of lesions at treated plants)/ the number of lesions at untreated plants)×100

The control value of the example compound 1-134 was 60 or more, and control effects thereof were confirmed.

Example 18

<Barrier to Growth of Rice>

The acetone solutions of each example compound and compounds described in the prior art documents shown in the below-mentioned Table 38 (hereinafter, referred to as compounds of Comparative Examples 1 to 5, respectively) were prepared such that the content thereof became 0.2 mg/mL, and then diluted to 10-fold with water to be subjected to conducting test. 0.25 mL of the diluted solution per 1 mL of the soil was made to be absorbed in the soil. Then, rice seeds (cultivar: Jikkoku) subjected to forcing to germination were seeded in the soil to be cultivated in plant cultivation chambers. The plant length of the rice grown to the first leaf stage was measured, and the ratio of the plant length, relative to the untreated plant length set as 100, (hereinafter, referred to as "the ratio of plant length relative to untreated plant length") was calculated. The presence or absence of the barrier to growth was determined from the calculated ratio.

The ratios of plant length relative to untreated plant length of the below-mentioned example compounds were 80 or more, and it was confirmed that phytotoxicity caused thereby was reduced in comparison with the compounds of Comparative Examples 1 to 5. The results indicated that the damage caused by the below-mentioned example compounds was reduced in comparison with the compounds of formula (1) in which $X^1$, $X^2$, $X^3$ or $X_4$ contains a chlorine atom.

1-1, 1-2, 1-3, 1-4, 1-5, 1-6, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-116, 1-117, 1-118, 1-120, 1-121, 1-122, 1-123, 1-124, 1-125, 1-126, 1-127, 1-128, 1-130, 1-131, 1-132, 1-133, 1-134, 1-135, 1-136, 1-137, 1-138, 1-139, 1-141, 1-142, 1-143, 1-148, 1-149, 1-150, 1-151, 1-152, 1-155, 1-156, 1-158, 1-160, 1-161, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 2-1, 2-2, 2-3, 2-4, 2-5, 3-1, 3-2, 4-1, 4-2, 4-3, 4-4, 4-5

TABLE 38

| Patent Document | Compound Number | Formula | Ratio of plant length relative to untreated plant length |
|---|---|---|---|
| Comparative Example 1 — Japanese Unexamined Patent Application, First Publication No. Sho 63-93766 | 4.2 | (structure: 2,6-dichloropyridine-4-carboxylate, $O^- N(C_2H_5)_3H^+$) | 49 |
| Comparative Example 2 — Japanese Unexamined Patent Application, First Publication No. Sho 63-93766 | 1.29 | (structure: 2,6-dichloropyridine-4-carboxylic acid propargyl ester, $OCH_2C\equiv CH$) | 52 |
| Comparative Example 3 — Japanese Unexamined Patent Application, First Publication No. Hei 9-165374 | 1 | (structure: 2,6-dichloro-N-(2-phenylethyl)pyridine-4-carboxamide) | 45 |

TABLE 38-continued

| | Patent Document | Compound Number | Formula | Ratio of plant length relative to untreated plant length |
|---|---|---|---|---|
| Comparative Example 4 | Japanese Unexamined Patent Application, First Publication No. Hei 10-95772 | 1 | | 64 |
| Comparative Example 5 | International Patent Application, Publication No. 2005-68430 | I-1 | | 66 |

Preparation Example 1

10 parts by mass of each example compound, 2 parts by mass of lauryl sulfate, 2 parts by mass of polyoxyethylene alkyl ether, 3 parts by mass of lignin sulfonate, 4 parts by mass of white carbon, and 79 parts by mass of clay were mixed and pulverized to obtain each wettable powder.

INDUSTRIAL APPLICABILITY

According to the present invention, a plant disease control agent and a novel compound that can reduce plant damage, and a method for controlling plant disease are provided. The plant disease control agent and the novel compound according to the present invention have excellent resistance-inducing activity and are useful to control plant diseases.

The invention claimed is:

1. A plant disease control agent comprising a compound of formula (1) as an active ingredient,

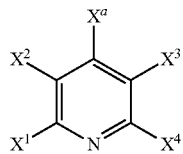
(1)

wherein:

$X^1$ and $X^4$ are fluorine atoms;

$X^2$ and $X^3$ are independently a hydrogen atom or a fluorine atom; and $X^a$ is formula (2), (3) or (5),

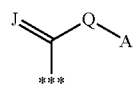
(2)

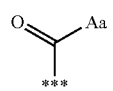
(3)

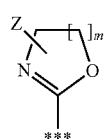
(5)

wherein the asterisk character "***" indicates the binding site to the carbon atom in the pyridine ring in the formula (1), if $X^4$ is formula (2):

J is an oxygen atom;

A is selected from the group consisting of:

a phenylcarbonyl group which may be substituted with one to four groups selected from the group consisting of groups belonging to Group D, a benzyl group, a phenyl group, and a phenoxy group, a phenyl group which may be substituted with one to five groups selected from the group consisting of groups belonging to Group D, a phenoxy group, and a benzyl group, a 5, 6, 7, 8-tetrahydronaphthyl group, and a group of formula (2A):

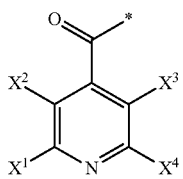

wherein $X^1$, $X^2$, $X^3$ and $X^4$ are as defined in formula (1);
\*\*\* indicates the binding site to Q; and
when A is formula (2A), Q is selected from the group consisting of:
  a divalent group of formula: —NH—$(CH_2)_n$—NH—,
  a divalent group of formula:—O—$CH_2$—CH=CH—$CH_2$—O—,
  a 1,3-phenylenediamino group, and
  a 1,4-phenylenediamino group,
  n is an integer of 2 to 8;
when A is not formula (2A), Q is selected from the group consisting of:
  an oxygen atom,
  a sulfur atom,
  a divalent group of formula:—NH—, and
  a divalent group of formula:—N($CH_3$)—;
if $X^a$ is formula (3):
  Aa is selected from the group consisting of:
    a piperidin-1-yl group,
    a morpholin-4-yl group,
    an indolin-1-yl group, and
    a benzoisothiazol-3 (2H)-one-1,1-dioxide-2-yl group,
if $X^a$ is formula (5):
  m is an integer of 1 to 3, and
  Z is selected from the group consisting of:
    a hydrogen atom,
    a halogen atom, and
    a methyl group,
and
Group D consists of:
  halogen atoms,
  a hydroxyl group,
  an amino group,
  a methylthio group,
  C1-4 alkyl groups which may be substituted with one to three halogen atoms,
  C1-4 alkyloxy groups which may be substituted with one to three halogen atoms,
  C1-4 alkylcarbonyl groups,
  a methoxycarbonyl group,
  an ethoxycarbonyl group,
  a benzylaminocarbonyl group;
  an acetoxy group; and
  a cyano group,
with a proviso that 2-(2,3,5,6-tetrafluoro-4-pyridinecarboxamide)-4-chloro-5-aminophenol and N-(3-chloro-4-fluorophenyl)-2,6-difluoroisonicotinamide are excluded.

2. The plant disease control agent according to claim 1, wherein, in formula (1), $X^2$ or $X^3$ is a hydrogen atom.

3. The plant disease control agent according to claim 1, wherein, in formula (1), $X^2$ and $X^3$ are hydrogen atoms.

4. The plant disease control agent according to claim 1, wherein $X^a$ in formula (1) is formula (2), and Q in formula (2) is a divalent group of formula:—NH—.

5. The plant disease control agent according to claim 1, wherein $X^a$ in formula (1) is formula (2), and Q in formula (2) is an oxygen atom.

6. The plant disease control agent according to claim 1, wherein $X^a$ in formula (1) is a group of formula (2), and A in formula (2) is selected from the group consisting of:
  a phenylcarbonyl group which may be substituted with one to four groups selected from the group consisting of groups belonging to Group D, a benzyl group, a phenyl group, and a phenoxy group; and
  a phenyl group which may be substituted with one to five groups selected from the group consisting of the groups belonging to Group D, a phenoxy group and a benzyl group.

7. A compound of formula (1):

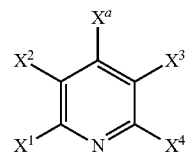

wherein:
  $X^1$ and $X^4$ are fluorine atoms;
  $X^2$ and $X^3$ are independently a hydrogen atom or a fluorine atom; and
  $X^a$ is formula (2), (3) or (5),

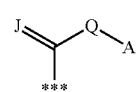

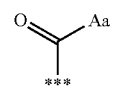

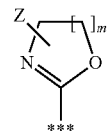

wherein the asterisk character "\*\*\*" indicates the binding site to the carbon atom in the pyridine ring in the formula (1),
if $X^a$ is formula (2):
  J is an oxygen atom;
  A is selected from the group consisting of:
  a phenylcarbonyl group which may be substituted with one to four groups selected from the group consisting of groups belonging to Group D, a benzyl group, a phenyl group, and a phenoxy group,
  a phenyl group which may be substituted with one to five groups selected from the group consisting of groups belonging to Group D, a phenoxy group, and a benzyl group,
  a 5, 6, 7, 8-tetrahydronaphthyl group, and a group of formula (2A):

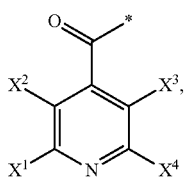

wherein $X^1$, $X^2$, $X^3$ and $X^4$ are as defined in formula (1);
indicates the binding site to Q; and
when A is formula (2A), Q is selected from the group consisting of:
a divalent group of formula: —NH—$(CH_2)_n$—NH—,
a divalent group of formula: —O—$CH_2$—CH=CH—$CH_2$—O—,
a 1,3-phenylenediamino group, and
a 1,4-phenylenediamino group,
n is an integer of 2 to 8; and
when A is not formula (2A), Q is selected from the group consisting of:
an oxygen atom,
a sulfur atom,
a divalent group of formula: —NH—, and
a divalent group of formula: —N($CH_3$)—;
if $X^a$ is formula (3):
Aa is selected from the group consisting of:
a piperidin-1-yl group,
a morpholin-4-yl group, an indolin-1-yl group, and
a benzoisothiazol-3 (2H)-one-1,1-dioxide-2-yl group;
if $X^a$ is formula (5):
m is an integer of 1 to 3,
Z is selected from the group consisting of:
a hydrogen atom,
a halogen atom, and
a methyl group;
Group D consists of:
halogen atoms,
a hydroxyl group,
an amino group,
a methylthio group,
C1-4 alkyl groups which may be substituted with one to three halogen atoms,
C1-4 alkyloxy groups which may be substituted with one to three halogen atoms,
C1-4 alkylcarbonyl groups,
a methoxycarbonyl group,
an ethoxycarbonyl group,
a benzylaminocarbonyl group,
an acetoxy group, and
a cyano group
with the provisos, that if $X^a$ is formula (2), J is an oxygen atom, and Q is —NH—, then A is not 3-chloro-4-fluorophenyl, and
2-(2,3,5,6-tetrafluoro-4-pyridinecarboxamide)-4-chloro-5-aminophenol is excluded.

8. The compound according to claim 7, wherein, in formula (1), $X^2$ or $X^3$ is a hydrogen atom.

9. The compound according to claim 7, wherein, in formula (1), $X^2$ and $X^3$ are hydrogen atoms.

10. The compound according to claim 7, wherein $X^a$ in formula (1) is formula (2), and Q in formula (2) is a divalent group of formula: —NH—.

11. The compound according to claim 7, wherein $X^a$ in formula (1) is formula (2), and Q in formula (2) is an oxygen atom.

12. The compound according to claim 7, wherein $X^a$ in formula (1) is formula (2), and A in formula (2) is selected from the group consisting of:
a phenylcarbonyl group which may be substituted with one to four groups selected from the group consisting of groups belonging to Group D, a benzyl group, a phenyl group, and a phenoxy group; and
a phenyl group which may be substituted with one to five groups selected from the group consisting of groups belonging to Group D, a phenoxy group and a benzyl group.

13. A method for controlling plant disease, comprising: applying a plant disease control agent to a plant body or a seed, or applying the plant disease control agent to a cultivation bed,
wherein the plant disease control agent comprises a compound of formula (1) as an active ingredient,

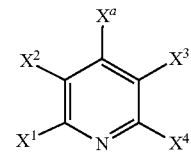

wherein:
$X^1$ and $X^4$ are fluorine atoms;
$X^2$ and $X^3$ are independently a hydrogen atom or a fluorine atom; and
$X^a$ is formula (2), (3) or (5),

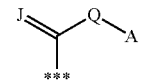

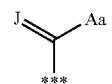

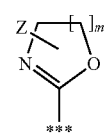

wherein the asterisk character "***" indicates the binding site to the carbon atom in the pyridine ring in the formula (1),
if $X^a$ is formula (2):
J is an oxygen atom;
A is selected from the group consisting of:
a phenylcarbonyl group which may be substituted with one to four groups selected from the group consisting of groups belonging to Group D, a benzyl group, a phenyl group, and a phenoxy group, a phenyl group which may be substituted with one to five groups selected from the group consisting of groups belonging to Group D, a phenoxy group; and a benzyl group,
a 5, 6, 7, 8-tetrahydronaphthyl group, and
a group of formula (2A):

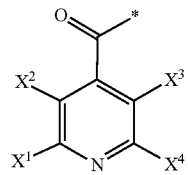

(2A)

wherein $X^1$, $X^2$, $X^3$ and $X^4$ are as defined in formula (1);
indicates the binding site to Q; and
when A is formula (2A), Q is selected from the group consisting of:
a divalent group of formula: —NH—$(CH_2)_n$—NH—;
a divalent group of formula: —O—$CH_2$—CH═CH—$CH_2$—O—,
a 1,3-phenylenediamino group, and
a 1,4-phenylenediamino group,
n is an integer of 2 to 8;
when A is not formula (2A), Q is selected from the group consisting of:
an oxygen atom,
a sulfur atom,
a divalent group of formula: —NH—, and
a divalent group of formula: —N($CH_3$)—;
if $X^4$ is formula (3):
Aa is selected from the group consisting of:
a piperidin-1-yl group;
a morpholin-4-yl group,
an indolin-1-yl group, and
a benzoisothiazol-3 (2H)-one-1,1-dioxide-2-yl group;
if $X^a$ is formula (5):
m is an integer of 1 to 3, and
Z is selected from the group consisting of:
a hydrogen atom,
a halogen atom, and
a methyl group;
Group D consists of:
halogen atoms,
a hydroxyl group,
an amino group,
a methylthio group,
C1-4 alkyl groups which may be substituted with one to three halogen atoms,
C1-4 alkyloxy groups which may be substituted with one to three halogen atoms,
C1-4 alkylcarbonyl groups,
a methoxycarbonyl group,
an ethoxycarbonyl group,
a benzylaminocarbonyl group,
an acetoxy group,
a nitro group, and
a cyano group.

14. A method for controlling plant disease, comprising: applying a compound of formula (1) to a plant body or a seed, or applying the compound to a cultivation bed,

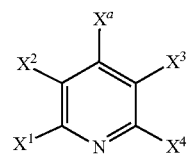

(1)

wherein:
$X^1$ and $X^4$ are fluorine atoms;
$X^2$ and $X^3$ are independently a hydrogen atom or a fluorine atom; and
$X^a$ is formula (2), (3) or (5),

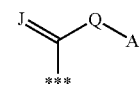

(2)

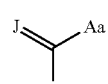

(3)

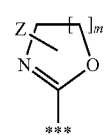

(5)

wherein the asterisk character "***" indicates the binding site to the carbon atom in the pyridine ring in the formula (1),
if $X^4$ is formula (2):
J is an oxygen atom;
A is selected from the group consisting of:
a phenylcarbonyl group which may be substituted with one to four groups selected from the group consisting of groups belonging to Group D, a benzyl group, a phenyl group, and a phenoxy group,
a phenyl group which may be substituted with one to five groups selected from the group consisting of groups belonging to Group D, a phenoxy group, and a benzyl group,
a 5, 6, 7, 8-tetrahydronaphthyl group, and
a group of formula (2A);

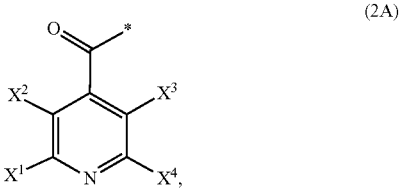

(2A)

wherein $X^1$, $X^2$, $X^3$ and $X^4$ are as defined in formula (1);
indicates the binding site to Q; and
when A is formula (2A), Q is selected from the group consisting of:
a divalent group of formula: —NH—$(CH_2)_n$—NH—,
a divalent group of formula: —O—$CH_2$—CH═CH—$CH_2$—O—, a 1,3-phenylenediamino group, and
a 1,4-phenylenediamino group,
n is an integer of 2 to 8; and
when A is not formula (2A), Q is selected from the group consisting of:
an oxygen atom,
a sulfur atom,
a divalent group of formula:—NH—, and
a divalent group of formula:—N(CH$_3$)—;
if X$^a$ is formula (3):
Aa is selected from the group consisting of:
sa piperidin-1-yl group,
a morpholin-4-yl group, an indolin-1-yl group, and a benzoisothiazol-3 (2H)-one-1,1-dioxide-2-yl group;
if X$^a$ is formula (5):
m is an integer of 1 to 3,
Z is selected from the group consisting of:
a hydrogen atom,
a halogen atom, and
a methyl group;
Group D consists of:
halogen atoms,
a hydroxyl group,
an amino group,
a methylthio group,
C1-4 alkyl groups which may be substituted with one to three halogen atoms,
C1-4 alkyloxy groups which may be substituted with one to three halogen atoms,
C1-4 alkylcarbonyl groups,
a methoxycarbonyl group,
an ethoxycarbonyl group,
a benzylaminocarbonyl group,
an acetoxy group,
a nitro group, and
a cyano group,
with the provisos that if X$^a$ is formula (2), J is an oxygen atom, and Q is —NH—, then A is not 3-chloro-4-fluorophenyl.

15. The plant disease control agent according to claim 1, wherein X$^a$ is formula (2), and A is a phenyl group which may be substituted with one to five groups selected from the group consisting of groups belonging to Group D, a phenoxy group, and a benzyl group.

16. The compound according to claim 7, wherein X$^a$ is formula (2), and A is a phenyl group which may be substituted with one to five groups selected from the group consisting of groups belonging Group D, a phenoxy group, and a benzyl group.

17. The plant disease control agent according to claim 1, wherein X$^a$ is formula (2).

18. The compound according to claim 7, wherein X$^a$ is formula (2).

19. The method according to claim 13, wherein X$^a$ is formula (2).

20. The method according to claim 14 wherein X$^a$ is formula (2).

* * * * *